United States Patent [19]
Jin et al.

[11] Patent Number: 5,668,159
[45] Date of Patent: Sep. 16, 1997

[54] 1,3,4-THIADIAZOLES AND 1,3,4-OXADIAZOLES AS IIB/IIIA ANTAGONISTS

[75] Inventors: Fuqiang Jin, Greenville; Pasquale Nicholas Confalone, Wilmington, both of Del.

[73] Assignee: The DuPont Merck Pharmaceutical Company, Wilmington, Del.

[21] Appl. No.: 643,438

[22] Filed: May 8, 1996

[51] Int. Cl.$^6$ .......... A01K 31/41; C07D 285/12; C07D 271/10

[52] U.S. Cl. .......... 514/363; 514/326; 514/364; 546/209; 548/136; 548/143; 548/144

[58] Field of Search .......... 548/136, 143, 548/144; 546/209; 514/363, 364, 370

[56] References Cited

U.S. PATENT DOCUMENTS 5,482,966  1/1996  Bird .......... 514/456

Primary Examiner—Robert Gerstl

[57] ABSTRACT

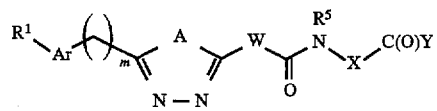

This invention relates to improved isoxazoline compounds including, but not limited to 1,3,4-thiadiazoles and 1,3,4-oxadiazoles of the formula which are useful as antagonists of the platelet glycoprotein IIb/IIIa fibrinogen receptor complex, to pharmaceutical compositions containing such compounds, and to methods of using these compounds, alone or in combination with other therapeutic agents, for the inhibition of platelet aggregation, as thrombolytics, and/or for the treatment of thromboembolic disorders.

12 Claims, No Drawings

1,3,4-THIADIAZOLES AND 1,3,4-OXADIAZOLES AS IIB/IIIA ANTAGONISTS

FIELD OF THE INVENTION

The present invention relates generally to 1,3,4-thiadiazoles and 1,3,4-Oxadiazoles which are useful as antagonists of the platelet glycoprotein IIb/IIIa fibrinogen receptor complex, to pharmaceutical compositions containing such compounds, processes for preparing such compounds, and to methods of using these compounds for the inhibition of platelet aggregation, as thrombolytics, and/or for the treatment of thromboembolic disorders.

BACKGROUND OF THE INVENTION

Hemostasis is the normal physiological process in which bleeding from an injured blood vessel is arrested. It is a dynamic and complex process in which platelets play a key role. Within seconds of vessel injury, resting platelets become activated and are bound to the exposed matrix of the injured area by a phenomenon called platelet adhesion. Activated platelets also bind to each other in a process called platelet aggregation to form a platelet plug. The platelet plug can stop bleeding quickly, but it must be reinforced by fibrin for long-term effectiveness, until the vessel injury can be permanently repaired.

Thrombosis may be regarded as the pathological condition wherein improper activity of the hemostatic mechanism results in intravascular thrombus formation. Activation of platelets and the resulting platelet aggregation and platelet factor secretion has been associated with a variety of pathophysiological conditions including cardiovascular and cerebrovascular thromboembolic disorders, for example, the thromboembolic disorders associated with unstable angina, myocardial infarction, transient ischemic attack, stroke, atherosclerosis and diabetes. The contribution of platelets to these disease processes stems from their ability to form aggregates, or platelet thrombi, especially in the arterial wall following injury.

Platelets are activated by a wide variety of agonists resulting in platelet shape change, secretion of granular contents and aggregation. Aggregation of platelets serves to further focus clot formation by concentrating activated clotting factors at the site of injury. Several endogenous agonists including adenosine diphosphate (ADP), serotonin, arachidonic acid, thrombin, and collagen, have been identified. Because of the involvement of several endogenous agonists in activating platelet function and aggregation, an inhibitor which acts against all agonists would represent a more efficacious antiplatelet agent than currently available antiplatelet drugs, which are agonist-specific.

Current antiplatelet drugs are effective against only one type of agonist; these include aspirin, which acts against arachidonic acid; ticlopidine, which acts against ADP; thromboxane $A_2$ synthetase inhibitors or receptor antagonists, which act against thromboxane $A_2$; and hirudin, which acts against thrombin.

Recently, a common pathway for all known agonists has been identified, namely platelet glycoprotein IIb/IIIa complex (GPIIb/IIIa), which is the membrane protein mediating platelet aggregation. A recent review of GPIIb/IIIa is provided by Phillips et al. *Cell* (1991) 65: 359–362. The development of a GPIIb/IIIa antagonist represents a promising new approach for antiplatelet therapy.

GPIIb/IIIa does not bind soluble proteins on unstimulated platelets, but GPIIb/IIIa in activated platelets is known to bind four soluble adhesive proteins, namely fibrinogen, von Willebrand factor, fibronectin, and vitronectin. The binding of fibrinogen and von Willebrand factor to GPIIb/IIIa causes platelets to aggregate. The binding of fibrinogen is mediated in part by the Arg-Gly-Asp (RGD) recognition sequence which is common to the adhesive proteins that bind GPIIb/IIIa.

Several RGD-peptidomimetic compounds have been reported which block fibrinogen binding and prevent the formation of platelet thrombi.

European Patent Application Publication Number 478363 relates to compounds having the general formula:

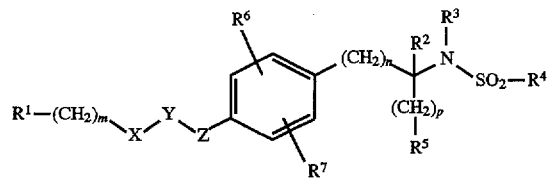

European Patent Application Publication Number 478328 relates to compounds having the general formula:

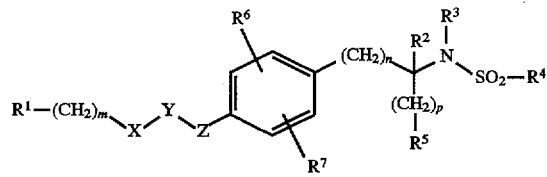

European Patent Application Publication Number 525629 (corresponds to Canadian Patent Application Publication Number 2,074,685) discloses compounds having the general formula:

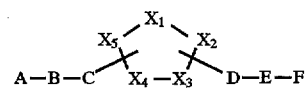

PCT Patent Application 9307867 relates to compounds having the general formula:

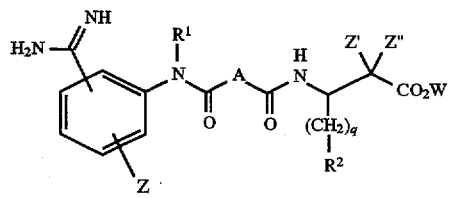

European Patent Application Publication Number 4512831 relates to compounds having the general formula:

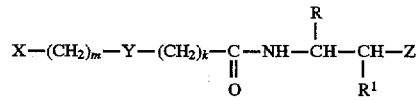

Copending commonly assigned U.S. patent application Ser. No. 08/337,920 (filed Nov. 10, 1994, Wityak et al.; published as WO95/13155, Jun. 1, 1995) discloses compounds having the general formula:

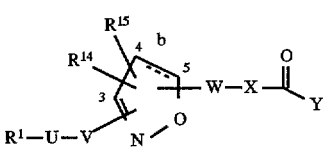

which are useful as IIb/IIIA antagonists.

Copending commonly assigned U.S. patent application Ser. No. 08/455,768) (filed May 31, 1995, Voss et al.) discloses compounds having the general formula:

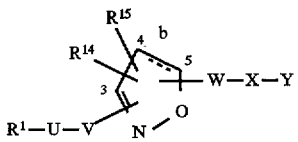

which are useful as $\alpha_v\beta_3$ antagonists.

None of the above references teaches or suggests the compounds of the present invention which are described in detail below.

SUMMARY OF THE INVENTION

One aspect of this invention provides novel compounds of Formula I (described below) which are useful as antagonists of the platelet glycoprotein IIb/IIIa complex. The compounds of the present invention inhibit the binding of fibrinogen to platelet glycoprotein IIb/IIIa complex and inhibit the aggregation of platelets. The present invention also includes pharmaceutical compositions containing such compounds of Formula I, and methods of using such compounds for the inhibition of platelet aggregation, as thrombolytics, and/or for the treatment of thromboembolic disorders.

The present invention also includes methods of treating cardiovascular disease, thrombosis or harmful platelet aggregation, reocclusion following thrombolysis, reperfusion injury, or restenosis by administering a compound of Formula I alone or in combination with one or more additional therapeutic agents selected from: anti-coagulants such as warfarin or heparin; anti-platelet agents such as aspirin, piroxicam or ticlopidine; thrombin inhibitors such as boro-arginine derivatives, hirudin or argatroban; or thrombolytic agents such as tissue plasminogen activator, anistreplase, urokinase or streptokinase; or combinations thereof.

Also included in the present invention are pharmaceutical kits comprising one or more containers containing pharmaceutical dosage units comprising a compound of Formula I, for the treatment of cell adhesion related disorders, including but not limited to thromboembolic disorders.

DETAILED DESCRIPTION OF THE INVENTION

This invention relates to novel compounds of the Formula I:

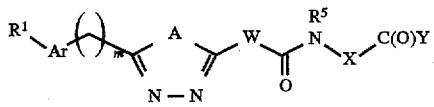

and their enantiomeric, diastereomeric, pharmaceutically acceptable salt or prodrug forms thereof wherein:

$R^1$ is selected from $R^2HN$—, $R^2HN(R^2N$=$)C$—, $R^2HN(CH_2)_qZ$—, $R^2HN(R^2N$=$)C(CH_2)_qZ$—, $R^2HN$ ($R^2N$=$)CN(R^2)$—, $R^2HNC(O)$—, $R^2(R^5O)N(R^2N$=$)$ C—, or $R^2HN(R^5ON$=$)C$—;

alternatively, $R^1$ is H when Ar is -(piperidinyl)-;

q is 1–3;

Z is selected from a bond (i.e. is absent), O, S, or S(=O), $S(=O)_2$;

$R^2$ is selected from H, aryl($C_1$–$C_{10}$ alkoxy) carbonyl, or $C_1$–$C_{10}$ alkoxycarbonyl, $C_1$–$C_4$ alkyl, $C_3$–$C_6$ alkenyl;

$R^5$ is selected from H or $C_1$–$C_{10}$ alkyl substituted with 0–1 $R^{4b}$;

$R^{4b}$ is selected from $C_1$–$C_6$ alkyl, $C_2$–$C_6$ alkenyl, $C_2$–$C_6$ alkynyl, $C_3$–$C_7$ cycloalkyl, $C_7$–$C_{14}$ bicycloalkyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, $C_1$–$C_6$ alkylcarbonyl, $C_6$–$C_{10}$ aryl, —N($R^{12}$)$R^{13}$, halo, $CF_3$, CN, $C_1$–$C_6$ alkoxycarbonyl, carboxy, piperidinyl, morpholinyl or pyridinyl;

Ar is selected from:
-(piperidinyl)- substituted with 0–2 $R^{6a}$,
-(phenyl)- substituted with 0–2 $R^{6a}$, or
-(pyridyl)- substituted with 0–2 $R^{6a}$;

$R^{6a}$ is selected from $C_1$–$C_4$ alkyl, $C_1$–$C_4$ alkoxy, halo, $CF_3$, $NO_2$, or $NR^{12}R^{13}$;

A is selected from O or S;

W is selected from —(CH$_2$)$_n$— or —S(CH$_2$)$_{n-1}$—;

X is selected from —C(CH$_2$—Ph)H—, —CH$_2$—, —CH$_2$C(NHR$^{12}$)H— or —C(CH$_2$NHR$^{12}$)H—;

Y is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, $C_{10}$ to $C_{14}$ (5-aryl-1,3-dioxa-cyclopenten-2-one-yl)methyloxy, ($R^2$)HN—($C_1$–$C_{10}$ alkoxy)—;

m is 0–2;

n is 1–4; and $R^{12}$ and $R^{13}$ are each independently selected from H; $C_1$–$C_{10}$ alkyl; $C_1$–$C_{10}$ alkoxycarbonyl; $C_1$–$C_{10}$ alkylcarbonyl; $C_1$–$C_{10}$ alkylsulfonyl; aryl, aryl($C_1$–$C_{10}$ alkyl)sulfonyl, and arylsulfonyl wherein said aryls and heteroaryls are substituted with 0–3 substituents selected from the group consisting of: $C_1$–$C_4$ alkyl, $C_1$–$C_4$ alkoxy, halo, $CF_3$, and $NO_2$; and heteroaryl ($C_1$–$C_4$ alkyl)sulfonyl, heteroarylcarbonyl, heteroarylsulfonyl, and heteroarylalkylcarbonyl wherein said heteroaryls are substituted with 0–3 substituents selected from the group consisting of: $C_1$–$C_4$ alkyl, $C_1$–$C_4$ alkoxy, halo, $CF_3$, and $NO_2$;

provided that m and n are chosen such that the number of atoms connecting $R^1$ and Y is in the range of 10–18.

Preferred compounds of the present invention are compounds of the formula I wherein:

$R^1$ is selected from $R^2NHC(=NR^2)$— or $R^2NHC(=NR^2)NH$—;

$R^2$ is selected from H, $C_1$–$C_{10}$ alkoxycarbonyl, or $C_1$–$C_4$ alkyl;

$R^5$ is selected from H or $C_1$–$C_4$ alkyl

Ar is selected from -(phenyl)- substituted with 0–2 $R^{6a}$, or -(piperidinyl)- substituted with 0–2 $R^{6a}$;

$R^{6a}$ is selected from $C_1$–$C_4$ alkyl, $C_1$–$C_4$ alkoxy, halo, $CF_3$, $NO_2$, or $NR^{12}R^{13}$;

A is selected from O or S;

W is selected from —$(CH_2)_n$— or —$S(CH_2)_{n-1}$—;

X is selected from —$CH_2C(NHR^{12})H$— or —$C(CH_2NHR^{12})H$—;

Y is selected from:
hydroxy;
$C_1$ to $C_{10}$ alkoxy;
methylcarbonyloxymethoxy-;
ethylcarbonyloxymethoxy-;
t-butylcarbonyloxymethoxy-;
cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl)methoxy-;
(1,3-dioxa-5-phenyl-cyclopenten-2-on-4-yl)methoxy-;
1-(2-(2-methoxypropyl)carbonyloxy)ethoxy-;

m is 1 or 2;
n is 1 or 2;

$R^2$ is selected from H; $C_1$–$C_6$ alkyl; $C_1$–$C_4$ alkoxycarbonyl; $C_1$–$C_6$ alkylcarbonyl; $C_1$–$C_6$ alkylsulfonyl; aryl, aryl($C_1$–$C_4$ alkyl)sulfonyl, and arylsulfonyl wherein said aryls are substituted with 0–3 substituents selected from the group consisting of: $C_1$–$C_4$ alkyl, $C_1$–$C_4$ alkoxy, halo, $CF_3$, and $NO_2$; and heteroaryl($C_1$–$C_4$ alkyl)sulfonyl, heteroarylsulfonyl, heteroarylcarbonyl or heteroarylmethylcarbonyl wherein said heteroaryls are substituted with 0–3 substituents selected from the group consisting of: $C_1$–$C_4$ alkyl, $C_1$–$C_4$ alkoxy, halo, $CF_3$, and $NO_2$; and $R^{13}$ is H.

The most preferred compounds of the present invention are:

Methyl $N^3$-[2-{2-(4-amidinophenyl)-1,3,4-thiadiazol-5-yl}-acetyl]-$N^2$-(n-butyloxycarbonyl)-2,3-(S)-diaminopropionate TFA salt $N^3$-[2-{2-(4-amidinophenyl)-1,3,4-thiadiazol-5-yl}-acetyl]-$N^2$-(n-butyloxycarbonyl)-2,3-(S)-diaminopropionic acid HCl salt Methyl $N^3$-[2-{2-(4-amidinophenyl)-1,3,4-thiadiazol-5-yl}-acetyl]-$N^2$-(3-methylphenylsulfonyl)-2,3-(S)-diaminopropionate TFA salt $N^3$-[2-{2-(4-amidinophenyl)-1,3,4-thiadiazol -5-yl)-acetyl]-$N^2$-(3-methylphenylsulfonyl)-2,3-(S)-diaminopropionic acid HCl salt Methyl $N^3$-[2-{2-(4-N-methylamidinophenyl)-1,3,4-thiadiazol-5-yl}-acetyl]-$N^2$-(3-methylphenylsulfonyl)-2,3-(S)-diaminopropionate TFA salt $N^3$-[2-{2-(4-N-methylamidinophenyl)-1,3,4-thiadiazol-5-yl}-acetyl]-$N^2$-(3-methylphenylsulfonyl)-2,3-(S)-diaminopropionic acid HCl salt Methyl $N^3$-[2-{2-(4-N-n-butylamidinophenyl)-1,3,4-thiadiazol-5-yl}-acetyl]-$N^2$-(3-methylphenylsulfonyl)-2,3-(S)-diaminopropionate TFA salt $N^3$-[2-{2-(4-N-n-butylamidinophenyl)-1,3,4-thiadiazol-5-yl}-acetyl]-$N^2$-(3-methylphenylsulfonyl)-2,3-(S)-diaminopropionic acid HCl salt Methyl $N^3$-[2-{2-(4-amidinophenyl)-1,3,4-thiadiazol-5-yl}-acetyl]-$N^2$-(2-methylphenylsulfonyl)-2,3-(S)-diaminopropionate TFA salt $N^3$-[2-{2-(4-amidinophenyl)-1,3,4-thiadiazol-5-yl}-acetyl]-$N^2$-(2-methylphenylsulfonyl)-2,3-(S)-diaminopropionic acid HCl salt Methyl $N^3$-[2-{2-(4-amidinophenyl)-1,3,4-thiadiazol-5-yl}-acetyl]-$N^2$-(3,5-dimethylisoxazol-4-ylsulfonyl)-2,3-(S)-diaminopropionate TFA salt $N^3$-[2-{2-(4-amidinophenyl)-1,3,4-thiadiazol-5-yl}-acetyl]-$N^2$-(3,5-dimethylisoxazol-4-ylsulfonyl)-2,3-(S)-diaminopropionic acid HCl salt Methyl $N^3$-[2-{2-(4-piperidinyl)-1,3,4-thiadiazol-5-yl}-acetyl]-$N^2$-(3-methylphenylsulfonyl)-2,3-(S)-diaminopropionate TFA salt Methyl $N^3$-[4-{2-(4-piperidinyl)-1,3,4-thiadiazol-5-yl}-butyryl]-$N^2$-(3-methylphenylsulfonyl)-2,3-(S)-diaminopropionate TFA salt $N^3$-[4-{2-(4-piperidinyl)-1,3,4-thiadiazol-5-yl}-butyryl]-$N^2$-(3-methylphenylsulfonyl)-2,3-(S)-diaminopropionic acid TFA salt Methyl $N^3$-[2-{2-(4-N,N'-di(trifluoroethyl)amidinophenyl)-1,3,4-thiadiazol-5-yl}-acetyl]-$N^2$-(3-methylphenylsulfonyl)-2,3-(S)-diaminopropionate Methyl $N^3$-[2-{2-(4-guanidinophenyl)-1,3,4-thiadiazol-5-yl}-acetyl]-$N^2$-(3-methylphenylsulfonyl)-2,3-(S)-diaminopropionate TFA salt $N^3$-[2-{2-(4-guanidinophenyl)-1,3,4-thiadiazol-5-yl}-acetyl]-$N^2$-(3-methylphenylsulfonyl)-2,3-(S)-diaminopropionic acid TFA salt Methyl $N^3$-[2-{2-(4-N-hydroxyamidinophenyl)-1,3,4-thiadiazol-5-yl}-acetyl]-$N^2$-(3-methylphenylsulfonyl)-2,3-(S)-diaminopropionate TFA salt Methyl $N^3$-[2-{2-(4-amidophenyl)-1,3,4-thiadiazol-5-yl}-acetyl]-$N^2$-(3-methylphenylsulfonyl)-2,3-(S)-diaminopropionate $N^3$-[2-{2-(4-Amidophenyl)-1,3,4-thiadiazol-5-yl}-acetyl]-$N^2$-(3-methylphenylsulfonyl)-2,3-(S)-diaminopropionic acid Methyl $N^3$-[2-{2-(4-amidinophenyl)-1,3,4-thiadiazol-5-ylthio}acetyl]-$N^2$-(n-butoxycarbonyl)-2,3-(S)-diaminopropionate HCl salt $N^3$-[2-{2-(4-Amidinophenyl)-1,3,4-thiadiazol-5-ylthio}acetyl]-$N^2$-(n-butoxycarbonyl)-2,3-(S)-diaminopropionic acid HCl salt Methyl $N^3$-[2-{2-(4-aminophenyl)-1,3,4-oxadiazol-5-ylthio}acetyl]-$N^2$-(n-butoxycarbonyl)-2,3-(S)-diaminopropionate TFA salt Methyl $N^3$-[2-{2-(4-guanidinophenyl)-1,3,4-oxadiazol-5-ylthio}acetyl]-$N^2$-(n-butoxycarbonyl)-2,3-(S)-diaminopropionate TFA salt Methyl $N^3$-[2-{2-(4-amidinophenyl)-1,3,4-oxadiazol-5-ylthio}-acetyl]-$N^2$-(n -butyloxycarbonyl)-2,3-(S)-diaminopropionate HCl salt Methyl $N^3$-[2-{2-(4-aminophenyl)-1,3,4-oxadiazol-5-yl}-acetyl]-$N^2$-(n-butyloxycarbonyl)-2,3-(S)-diaminopropionate Methyl $N^3$-[2-{2-(4-amidinophenyl)-1,3,4-oxadiazol-5-yl}acetyl]-$N^2$-(n-butyloxycarbonyl)-2,3-(S)-diaminopropionate TFA salt Methyl $N^3$-[2-{2-(4-guanidinophenyl)-1,3,4-oxadiazol-5-yl}-acetyl]-$N^2$-(n-butyloxycarbonyl)-2,3-(S)-diaminopropionate TFA salt Methyl N-[2-{2-(4-aminophenyl)-1,3,4-oxadiazol-5-ylthio}-acetyl]glycine Methyl N-[2-{2-(4-guanidinophenyl)-1,3,4-oxadiazol-5-ylthio}-acetyl]glycine TFA salt Methyl N-[2-{2-(4-guanidinophenyl)-1,3,4-oxadiazol-5-ylthio}-acetyl]-(S)-phenylalanine TFA salt Ethyl N-[2-{2-(4-amidinophenyl)-1,3,4-oxadiazol-5-ylthio}-acetyl]-(S)-phenylalanine HCl salt Methyl $N^2$-[2-{2-(4-aminophenyl)-1,3,4-oxadiazol-5-ylthio}-acetyl]-N3-(n-butyloxycarbonyl)-2,3-(S)-diaminopropionate TFA salt Methyl $N^2$-[2-{2-(4-N,N'-bis-tert-butoxycarbonylguanidinophenyl)-1,3,4-oxadiazol-5-ylthio}-acetyl]-$N^3$-(n-butyloxycarbonyl)-2,3-(S)-diaminopropionate Methyl $N^2$-[2-{2-(4-amidinophenyl)-1,3,4-thiodiazol-5-ylthio}-acetyl]-$N^3$-(n-butyloxycarbonyl)-2,3-(S)-diaminopropionate HCl salt The compounds of Formula I of the present invention are useful for the treatment (including prevention) of thromboembolic disorders. The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or such disorders associated with diabetes, comprising administering to a mammal in need of such treatment a therapeutically effective amount of a compound of Formula I described above.

The compounds of the present invention are useful for inhibiting the binding of fibrinogen to blood platelets, inhibiting aggregation of blood platelets, treating thrombus formation or embolus formation, or preventing thrombus or embolus formation in a mammal. The compounds of the invention may be used as a medicament for blocking fibrinogen from acting at its receptor site in a mammal.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption, and where the aggregated platelets may form thrombi and thromboemboli. The compounds of the present invention may be administered to these surgical patients to prevent the formation of thrombi and thromboemboli.

Extracorporeal circulation is routinely used during cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the extracorporeal circuit. Platelets released from artificial surfaces show impaired homeostatic function. The compounds of the invention may be administered to prevent such ex vivo adhesion.

The compounds of the present invention may be used for other ex vivo applications to prevent cellular adhesion in biological samples.

Other applications of these compounds include prevention of platelet thrombosis, thromboembolism, and reocclusion during and after thrombolytic therapy and prevention of platelet thrombosis, thromboembolism and reocclusion after angioplasty of coronary and other arteries and after coronary artery bypass procedures. The compounds of the present invention may also be used to prevent myocardial infarction. The compounds of the present invention are useful as thrombolytics for the treatment of thromboembolic disorders.

The compounds of the present invention can also be administered in combination with one or more additional therapeutic agents select from: anti-coagulant or coagulation inhibitory agents, such as heparin or warfarin; anti-platelet or platelet inhibitory agents, such as aspirin, piroxicam, or ticlopidine; thrombin inhibitors such as boropeptides, hirudin or argatroban; or thrombolytic or fibrinolytic agents, such as plasminogen activators, anistreplase, urokinase, or streptokinase.

The compounds of Formula I of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic disorders.

By "therapeutically effective amount" it is meant an amount of a compound of Formula I that when administered alone or in combination with an additional therapeutic agent to a cell or mammal is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term anti-coagulant agents (or coagulation inhibitory agents), as used herein, denotes agents that inhibit blood coagulation. Such agents include warfarin (available as Coumadin™) and heparin.

The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam. Piroxicam is commercially available from Pfizer Inc. (New York, N.Y.), as Feldane™. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof.

The phrase thrombin inhibitors (or anti-thrombin agents), as used herein, denotes inhibitors of the serine protease thrombin and other inhibitors of thrombin synthesis such as Factor XA. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boroarginine derivatives and boropeptides, hirudin and argatroban, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471 651 A2, the disclosures of which are hereby incorporated herein by reference, in their entirety.

The phrase thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. Anistreplase is commercially available as Eminase™. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

GPIIb/IIIa is known to be overexpressed in metastatic tumor cells. The compounds or combination products of the present invention may also be useful for the treatment, including prevention, of metastatic cancer.

The compounds of the present invention are also useful as standard or reference compounds, for example as a quality standard or control, in tests or assays involving the binding of fibrinogen to platelet GPIIb/IIIa. Such compounds may be provided in a commercial kit, for example, for use in pharmaceutical research involving GPIIb/IIIa. The compounds of the present invention may also be used in diagnostic assays involving platelet GPIIb/IIIa.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^1$, $R^2$, $R^{4b}$, $R^{6a}$, $R^{12}$, and $R^{13}$, n, etc.) occurs more than one time in any constituent or in any formula, its definition on each occurrence is independent of its definition at every other occurrence.

When a bond to a substituent is shown to cross the bond connecting two atoms in a ring, then such substituent may be bonded to any atom on the ring. When a bond joining a substituent to another group is not specifically shown or the atom in such other group to which the bond joins is not specifically shown, then such substituent may form a bond with any atom on such other group.

When a substituent is listed without indicating the atom via which such substituent is bonded to the rest of the compound of Formula I, then such substituent may be bonded via any atom in such substituent. For example, when the substituent is piperidinyl, piperidinyl, or morpholinyl, unless specified otherwise, said piperidinyl, piperidinyl, morpholinyl group may be bonded to the rest of the compound of Formula I via any atom in such piperidinyl, piperidinyl, morpholinyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_1$–$C_{10}$" denotes alkyl having 1 to 10 carbon atoms); "alkoxy" represents an alkyl group of indicated number of carbon atoms attached through an oxygen bridge; "cycloalkyl" is intended to include saturated ring groups, including mono-, bi-, or poly-cyclic ring systems, such as cyclopropyl, cyclobutyl, cyclopentyl, cyclohexyl, cycloheptyl, cyclooctyl, and adamantyl; and "bicycloalkyl" is intended to include saturated bicyclic ring groups such as [3.3.0]bicyclooctane, [4.3.0]bicyclononane, [4.4.0] bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "alkylene", "alkenylene", "phenylene", and the like, refer to alkyl, alkenyl, and phenyl groups, respectively, which are connected by two bonds to the rest of the structure of Formula I. Such "alkylene", "alkenylene", "phenylene", and the like, may alternatively and equivalently be denoted herein as "-(alkyl)-", "-(alkenyl)-" and "-(phenyl)-", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl optionally substituted with 0–3 groups independently selected from methyl, methoxy, amino, hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl; the term "arylalkyl" represents an aryl group attached through an alkyl bridge.

As used herein, the term "heteroaryl" refers to aromatic heterocyclic groups. Such heteroaryl groups are preferably 5–6 membered monocylic groups or 8–10 membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyridazinyl, benzofuranyl, benzothienyl, benzimidazolyl, quinolinyl, or isoquinolinyl.

As used herein, the term "chiral amine" refers to any amine containing compound that also contains a chiral center. Such compounds include, by way of example and without limitation, either enantiomer of cinchonidine, ephedrine, 2-phenylglycinol, 2-amino-3-methoxy-1-propanol, quinidine and pseudoephedrine.

As used herein, "pharmaceutically acceptable salts" refer to derivatives of the disclosed compounds wherein the parent compound of Formula I is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula I, and the like. Examples the prodrug forms of the compounds of the present invention include the following esters:

methyl; ethyl; isopropyl; methylcarbonyloxymethyl-; ethylcarbonyloxymethyl-; t-butylcarbonyloxymethyl-; cyclohexylcarbonyloxymethyl-; 1-(methylcarbonyloxy)ethyl-; 1-(ethylcarbonyloxy)ethyl-; 1-(t-butylcarbonyloxy)ethyl-; 1-(cyclohexylcarbonyloxy)ethyl-; i-propyloxycarbonyloxymethyl-; cyclohexylcarbonyloxymethyl-; t-butyloxycarbonyloxymethyl-; 1-(i-propyloxycarbonyloxy)ethyl-; 1-(cyclohexyloxycarbonyloxy)ethyl-; 1-(t-butyloxycarbonyloxy)ethyl-; dimethylaminoethyl-; diethylaminoethyl-; (5-methyl-1,3-dioxacyclopenten-2-on-4-yl)methyl-; (5-(t-butyl)-1,3-dioxacyclopenten-2-on-4-yl)methyl-; (1,3-dioxa-5-phenyl-cyclopenten-2-on-4-yl)methyl-; 1-(2-(2-methoxypropyl)-carbonyloxy)ethyl-.

The pharmaceutically acceptable salts of the compounds of Formula I include the conventional non-toxic salts or the quaternary ammonium salts of the compounds of Formula I formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The following abbreviations are used herein:

| | |
|---|---|
| Boc | tert-butyloxycarbonyl |
| Boc$_2$O | di-tert-butyl dicarbonate |
| Cbz | benzyloxycarbonyl |
| DEC | 1-(3-dimethylaminopropyl)-3-ethylcarbodiimide hydrochloride |
| DIEA | diisopropylethylamine |
| DMAP | 4-dimethylaminopyridine |
| DMF | N,N-dimethylformamide |
| EtOAc | ethyl acetate |
| EtOH | ethyl alcohol |
| pyr | pyridine |
| TBTU | 2-(1H-Benzotriazol-1-yl)-1,1,3,3-tetramethyluronium tetrafluoroborate |
| TFA | trifluoroacetic acid |
| THF | tetrahydrofuran |

The central synthetic portion of the current invention is the construction of the four heterocycle cores, 1,3,4-thiadiazole, 1,3,4-oxadiazole, 1,3,4-oxadiazol-2-yl-sulfide and 1,3,4-thiadiazol-2-yl-sulfide, which are presented in the compounds claimed in this invention. Generally, a compound useful as fibrinogen receptor antaganist is made from an intermediate acid with one of the four heterocycle core structures mentioned above.

Scheme I represents a general synthetic sequence to the thiadiazole(1-5) which is a key intermediate acid for the syntheses of the compounds of this invention. An appropriately substituted ester(1-1) is treated with hydrazine monohydrate to afford the hydrazide(1-2) which is then converted to the N,N'-diacylhydrazine(1-3) on reaction with an acid chloride in aqueous THF using NaHCO3 as base. The N,N'-diacylhydrazine thus obtained can be readily cyclized to give the 1,3,4-thiadizole(1-4) using Lawessen reagent (M. P. Cava, et al, *Tetrahedron* 1985, 41, 5061). This cyclization could also be effected by using reagents such as P2S5 as reported by Stolle, et al (*J Prakt. Chem* 1904, 69, 145). The hydrolysis of the ester(1-4) using LiOH in aqueous THF affords the 1,3,4-thiadiazole(1-5).

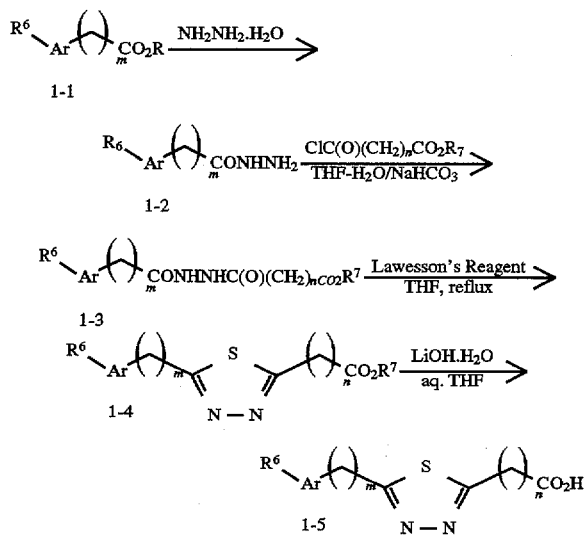

Cyclodehydration of the N,N'-diacylhydrazine(1-3) using POCl3 according to the method of Klingsberg (*J. Am. Chem. Soc.* 1958, 80, 5788) followed by a LiOH hydrolysis (Scheme II) readily gives the 1,3,4-oxadiazole(2-3), which is another key intermediate acid for the syntheses of the compounds claimed in this invention. Other dehydrating agents including chlorosulfonic acid (Ger. Pat. 825111 [C.A.1955,49,630]), sulfuryl chloride, (Ger. Pat. 825111 [C.A.1955,49,630]), phosphorus pentoxide (Stolle, et al, J. Prakt. Chem. 1904, 69, 382), p-toluenesulfonic acid (Ger. Pat. 825111[C.A.1955,49,630]) may be used to bring about this cyclodehydration.

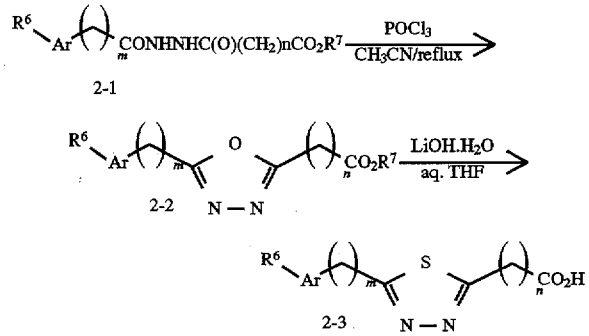

The 1,3,4-oxadiazol-2-yl-sulfide(3-2) may be obtained directly from the hydrazide(3-1) adopting the method of Confalone, et al (J. Am. Chem. Soc. 1983, 105, 902) (Scheme III). The hydrazide(3-1) is first treated with ethanolic potassium hydroxide, then with carbon disulfide and finally with an appropriately substituted halide (or other electrophiles) upon heating to afford the key intermediate acid 1,3,4-oxadiazol-2-yl-sulfide(3-2).

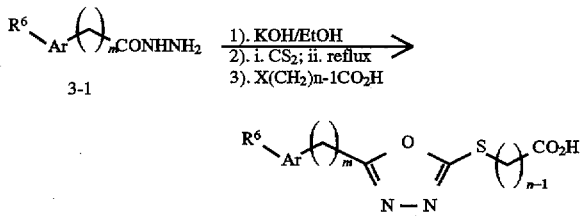

Scheme IV depicts a general synthetic sequence to the 1,3,4-thiadiazol-2-yl-sulfide(4-5) which is also an key intermediate acid for the preparation of the compounds of this instant invention. An appropriately substituted acid chloride (4-1) is treated with benzyldithiocarhydrazide in pyridine to yield the acyldithiocarbazate(4-2), which cyclizes under conditions of refluxing benzene in the presence of p-toluenesulfonic acid according to the method of Fujii et al (J. Pharm. Soc. Japan 1954, 74, 1056) and Young et al (J. Am. Chem. Soc. 1955, 77, 400). The concentrated sulfuric acid can also be used to bring about this cyclization. Oxidation of the sulfide(4-3) using common oxidants such as potassium permanganate give the corresponding sulfone (4-4), which is converted to the desired 1,3,4-thiadiazol-2-yl-sulfide(4-5) on treatment with an appropriately substituted thiol in the presence of a suitable base such as triethylamine.

Scheme IV

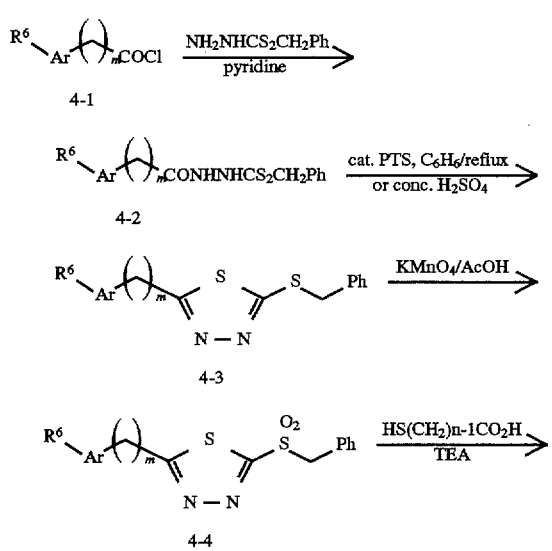

Compounds of the instant invention can be prepared from the above four acids 1-5, 2-3, 3-2, 4-5 via a coupling with an appropriately substituted α- or β- amino ester using standard coupling reagents, such as DCC/HOBt, followed by suitable substitute modifications, among which are the nitrile-to-amidine and amine-to-guanidine transformations. Examples are given below to show these synthetic protocols.

In Scheme V, the nitrile acid(5-1), which is prepared according to the synthetic sequence presented in Scheme I, is coupled with the amino ester(5-2) using TBTU as coupling reagent to afford the nitrile amide(5-3). The nitrile amide is then converted to the amidine via the imidate under standard conditions followed by ester hydrolysis(LiOH in aq. THF or 4N HCl). Compounds claimed in this invention can be readily prepared by combining the synthetic protocols depicted in Scheme I–V.

Scheme V

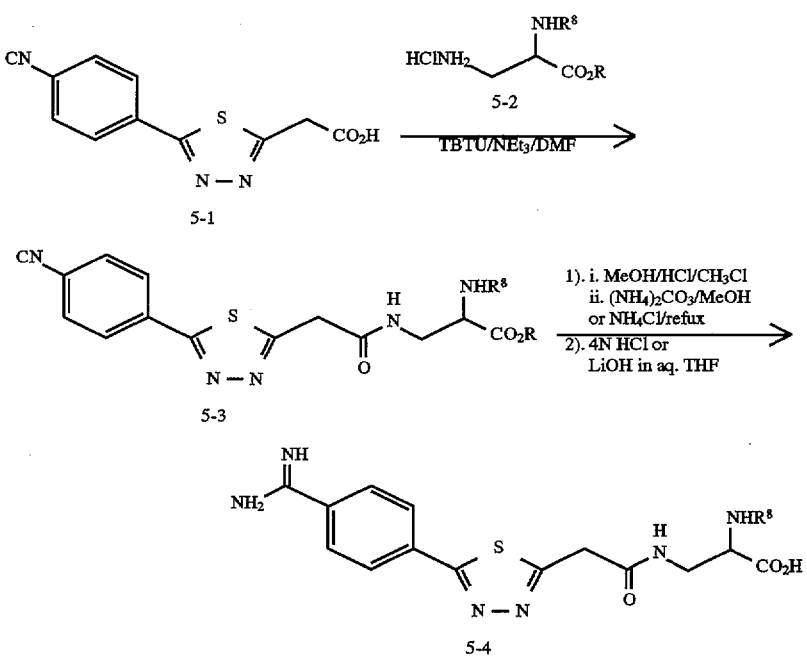

-continued
Scheme IV

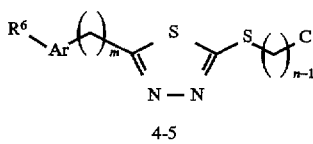

Compounds of Formula I wherein R1 is R2HN(R2N=) CN(R2)— are prepared as illustrated in Scheme VI. The nitrile acid(6-1) obtained according to the synthetic route depicted in Scheme II is coupled with an appropriately substituted amino ester(6-2) using the conditions described in Scheme V to provide the nitrile amide(6-3), which is converted to the amine amide(6-4) by catalytic hydrogenation. The transformation of the amine(6-4) to the guanidine (6-5) is brought about by using the method described by Kim, et al (Tetrahedron Lett. 1993, 48, 7677).

Scheme VI

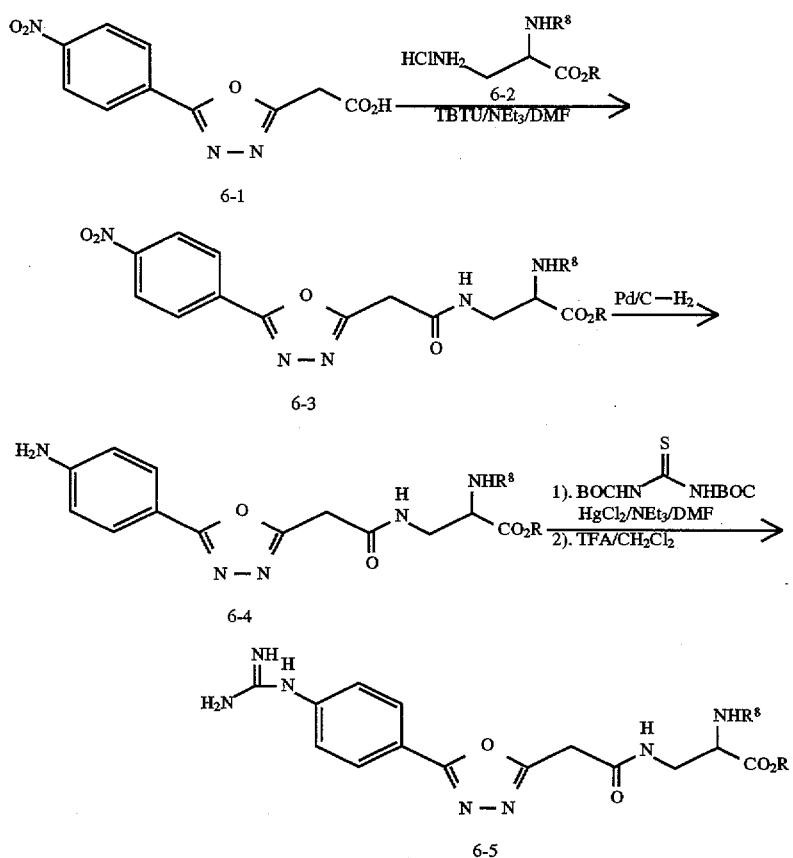

The conversion of a nitro compound to an amine as shown in Scheme VI provides a synthesis to the compounds of formula I wherein R1 is R2HN— or R2HN(CH2)qZ—. These compounds may also be prepared by deprotection of the protected amines as illustrated in Scheme VII.

with an appropriate alcohol under acidic conditions (J. Med. Chem. 1991, 34, 851) or with hydrogen peroxide under basic conditions (J. Am. Chem. Soc. 1958. 80, 2257).

Compounds of Formula I Wherein R1 is R2(R5O)N (R2N=)C— or R2HN(R5N=)C— may be prepared by

Scheme VII

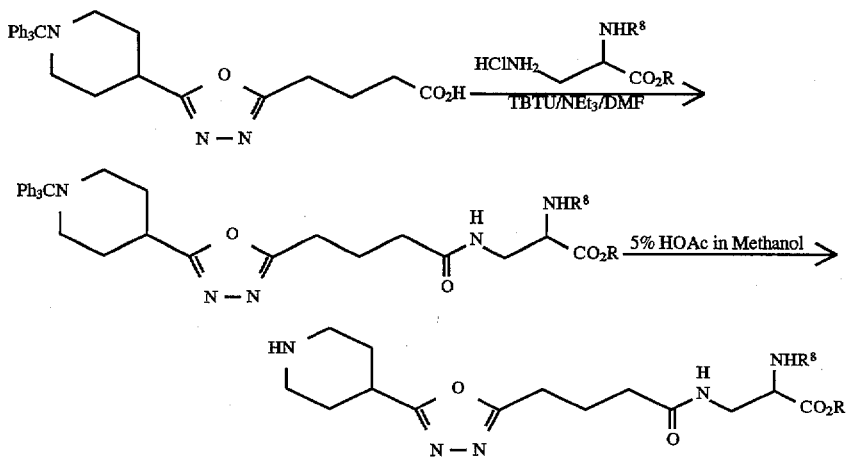

Compounds of formula I wherein R1 is R2HNC(O)— may be prepared by reaction of the corresponding nitrile reaction of the corresponding nitrile with an appropriately substituted hydroxyamine.

A further example is given in Scheme VIII to show an alternative synthetic sequence to the compounds of this invention. The hydrazide(8-1), after treated with methanolic potassium hydroxide and carbon disulfide, is captured directly with an amide halide(8-2) to give the nitrile amide (8-3), which is converted to the amidine(8-4) under the normal conditions as mentioned above.

Part C. Methyl 2-[2-(4-cyanophenyl)-1,3,4-thiadiazol-5-yl]acetate

A mixture of N-(4-cyanobenzoyl)-N'-(2-methoxycarbonylacetyl)hydrazine(1 g, 3.8 mmol) and Lawesson's reagent(780 mg, 1.9 mmol) in anhydrous THF (15 ml) was gently refluxed for 1 hr. The solution was then evaporated to dryness and the residue washed with ethyl

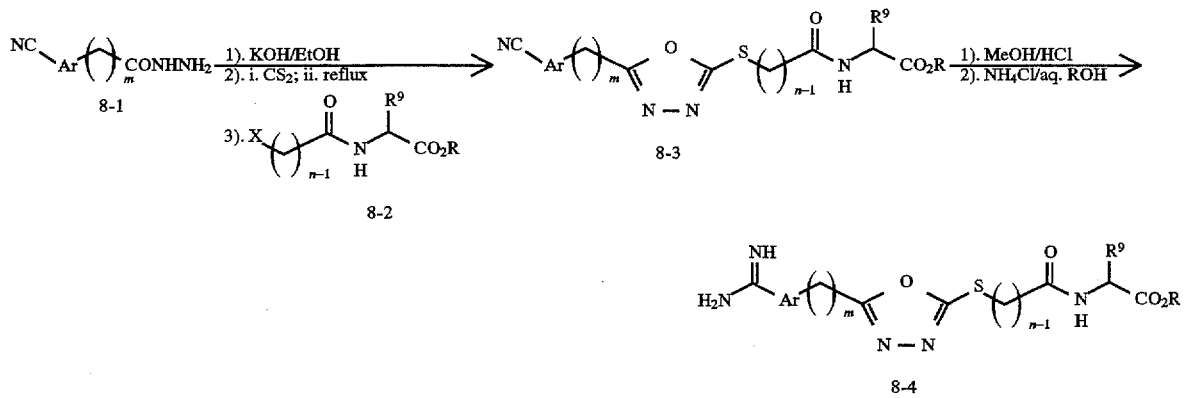

Scheme VIII

The appropriately substituted α- or β- amino acids may be purchased commercially or synthesized conventionally. The synthesis of N²-substituted diaminopropionic acid derivatives can be carried out via Hoffman rearrangement of a wide variety of asparagine derivatives as described in Synthesis, 266–267, (1981).

The compounds of this invention and their preparation can be further understood by the following procedures and examples, which exemplify but do not constitute a limit of their invention.

EXAMPLE 1

Methyl N³-[2-{2-(4-amidinophenyl)-1,3,4-thiadiazol-5-yl}-acetyl]-N²-(n-butyloxycarbonyl)-2,3-(S)-diaminopropionate TFA salt Part A. 4-Cyanobenzoylhydrazine A mixture of methyl 4-cyanobenzoate(10.8 g, 67 mmol) and hydrazine monohydrate(18.6 g, 371 mmol) in absolute ethanol(70 ml) was heated to reflux for 3 hrs and then was allowed to cool down to rt. The solid portion was collected by filtration and washed with cold ethanol(20 ml) and then dried to give the product(8.7 g, 81% yield). M.P.: 201° C. ¹H NMR(300 MHz, CDCl₃) δ4.14(s, 2H), 7.40(s, 1H), 7.76(d, J=8, 2H), 7.88(d, J=8, 2H); MS(NH₃-CI) Calc. for (M+1)⁺: 162. Found: 162.

Part B. N-(4-cyanobenzyl)-N'-(2-methoxycarbonylacetyl)hydrazine

To a suspension of 4-cyanobenzoylhydrazine(500 mg, 3.1 mmol) in aqueous THF(10 ml, 1:1 v/v) containing sodium bicarbonate(290 mg, 3.4 mmol), cooled with ice-water, was added methyl malonyl chloride(470 mg, 3.4 mmol) dropwise. After addition, the ice-water bath was removed and the mixture was stirred at rt for 2 hrs. The THF was evaporated under reduced pressure and the product as a solid powder was then collected by filtration and dried. (650 mg, 80% yield). ¹H NMR(300 MHz, CDCl₃) δ3.45(s, 2H), 3.80(s, 3H), 7.78(d, J=8, 2H), 7.95(d, J=8, 2H), 9.5(d, J=6, 1H), 10.2(d, J=6, 1H); MS(NH₃-CI) Calc. for (M+1)⁺: 262. Found: 262.

acetate. Crystallization of the solid thus obtained afforded the product(680 mg, 73% yield). ¹H NMR(300 MHz, CDCl₃) δ3.83(s, 3H), 4.26(s, 2H), 7.70(d, J=8, 2H), 8.10(d, J=8, 2H); MS(NH₃-CI) Calc. for (M+1)⁺: 260. Found: 260.

Part D. 2-[2-(4-cyanophenyl)-1,3,4-thiadiazol-5-yl]acetic acid

Methyl 2-[2-(4-cyanophenyl)-1,3,4-thiadiazol-5-yl]acetate(1 g, 3.7 mmol) was suspended in a mixture solvent of methanol, THF and water(30 ml, 1:1:1 v/v/v) containing lithium hydroxide monohydrate(170 mg, 4.0 mmol). The resulting mixture was stirred at rt for 2 hrs and then evaporated to dryness. The residue was washed with water (10 ml) and then dried(810 mg, 85% yield). ¹H NMR(300 MHz, DMSO-d₆) δ4.38(s, 2H), 8.0(d, J=8, 2H), 8.20(d, J=8, 2H); MS(NH₄-DCI) Calc. for (M+1)⁺: 256. Found: 256.

Part E. Methyl N²-Cbz-L-2,3-diaminopropionate HCl salt.

N²-Cbz-L-2,3-diaminopropionic acid (10 mmol, 2.39 g) was dissolved in 20 mL methanol and 20 mL 4N HCl in dioxane and the solution was stirred for 4 hours and then concentrated to give a solid. The solid was washed with ether several times to give 2.50 g (87%) product. NMR (DMSO-d₆): δ8.38(b, 3H); 7.96(d, 1H); 7.38(m, 5H); 5.05(s, 2H); 4.44(m, 1H); 3.66(s, 3H); 3.14(m, 2H).

Part F: Methyl N²-Cbz-N³-Boc-L-2,3-diaminopropionate.

To a solution of methyl N²−Cbz-(S)-2,3-diaminopropionate HCl salt (16.3 mmol, 4.7 g) and di-tert-butyl dicarbonate (16.3 mmol, 3.56 g) in 30 mL chloroform cooled in an ice bath was added triethylamine (34 mmol, 4.7 mL) and the solution was stirred in the ice bath for 1 hour and at room temperature for 3 hours and concentrated. The residue was taken up in ethyl acetate and the solution was washed with dilute citric acid, brine, NaHCO₃ and brine, dried (MgSO₄), and concentrated. Crystallization from ether/petroleum ether gave 5.2 g (92%) product. NMR (DMSO-d₆): δ7.60(d, 1H); 7.35(m, 5H); 6.88(t, 1H); 5.02(s, 2H); 4.14(m, 1H); 3.60(s, 3H); 3.28(m, 2H); 1.37(s, 9H).

Part G: Methyl N³-Boc-(S)-2,3-diaminopropionate Formic acid salt.

A mixture of methyl N²-Cbz-N³-Boc-(S)-2,3-diaminopropionate. (14 mmo, 5.0 g), formic acid (42 mmol, 1.6 mL) and 10% Pd/C (500 mg) in 40 mL methanol was stirred at room temperature for 1 hour and filtered through a celite. The filtrate was concentrated and the residue was triturated with ether-petroleum ether to give 3.7 g (100%) solid product. NMR (DMSO-$d_6$): $\delta$8.20(s, 1H); 6.90(t, 1H); 5.36(b, 3H); 3.61 9s, 3H); 3.51(t, 1H); 3.18(t, 2H); 1.38(s, 9H).

Part H: Methyl $N^2$-n-butyloxycarbonyl-$N^3$-Boc-(S)-2,3-diaminopropionate.

To a mixture of methyl $N^3$-Boc-(S)-2,3-diaminopropionate HCO$_2$H salt (14 mmol, 3.7 g) and NaHCO$_3$ (40 mmol, 3.4 g) in 10 mL water and 10 mL THF cooled in an ice bath was added slowly butyl chloroformate (16 mmol, 2 mL) over 15 min. After stirring for 1 hour, ethyl acetate was added and the solution was washed with dilute citric acid, brine, NaHCO$_3$ and brine, dried (MgSO$_4$), and concentrated to give 4.4 g (100%) oily product. NMR (DMSO-$d_6$): $\delta$7.37(d, 1H); 6.84(t, 1H); 4.10(m, 1H); 3.96(t, 2H); 3.60(s, 3H); 3.26(m, 2H); 1.52(m, 2H); 1.38(s, 9H); 1.36(m, 2H); 0.88(t, 3H).

Part I: Methyl $N^2$-n-butyloxycarbonyl-(S)-2,3-diaminopropionate TFA salt.

Methyl $N^2$-n-butyloxycarbonyl-$N^3$-Boc-(S)-2,3-diaminopropionate (13.9 mmol, 4.4 g) was dissolved in 25 mL methylene chloride and 35 mL TFA and after 1 hour, the solution was concentrated to give an oily product. Yield 4.8 g (100%). NMR (DMSO-$d_6$): $\delta$8.02(b, 3H); 7.68 (d, 2H); 4.38(m, 1H); 3.99(t, 2H); 3.68(s, 3H); 3.22(m, 1H); 3.06(m, 1H); 1.55(m, 2H); 1.34(m, 2H); 0.89(t, 3H).

Part J: Methyl $N^3$-[2-{2-(4-cyanophenyl)-1,3,4-thiadiazol-5-yl}acetyl]-$N^2$-(n-butyloxycarbonyl)-2,3-(S)-diaminopropionate To a mixture of 2-{2-(4-cyanophenyl)-1,3,4-thiadiazol-5-yl}acetic acid(650 mg, 2.65 mmol), methyl $N^2$-butyloxycarbonyl-(S)-2,3-diaminopropionate TFA salt (970 mg, 2.9 mmol) and triethylamine(1.07 g, 10.6 mmol) in DMF(15 ml), cooled with ice-water, was added TBTU(940 mg, 2.9 mmol). After stirring for 3 hrs, the reaction mixture was diluted with ethyl acetate and washed with dilute citric acid, dilute NaHCO$_3$ and brine successively, then dried. Concentration followed by chromatography with ethyl acetate as the eluent gave the product as an amorphous solid(860 mg, 73% yield). $^1$H NMR(300 MHz, CDCl$_3$) $\delta$0.91(t, J=6, 3H), 1.30(m, 2H), 1.60(m, 2H), 3.70(m, 2H), 3.81(s, 3H), 4.04(t, J=6, 2H), 4.18(s, 2H), 4.50(m, 1H), 5.70(s, 1H), 7.06(s, 1H), 7.80(d,J=8, 2H), 8.10(d, J=8, 2H); MS(ESI) Calc. for (M+1)$^+$: 446. Found: 446.

Part K. Methyl $N^3$-[2-{2-(4-formamidinophenyl)-1,3,4-thiadiazol-5-yl}-acetyl]-$N^2$-(butyloxycarbonyl)-2,3-(S)-diaminopropionate TFA salt Dry HCl gas was bubled through a solution of Methyl $N^3$-[2-{2-(4-cyanophenyl)-1,3,4-thiadiazol-5-yl}acetyl]-$N^2$-(butyloxycarbonyl)-2,3-(S)-diaminopropionate(380 mg 0.85 mmol) in dry CHCl$_3$ containing anhydrous methanol (41 mg, 1.3 mmol), cooled with salt ice-water bath, at 0° C. for 5 hrs. The resulting solution was then kept at 0° C. for 6 hrs and at 15° C. for 12 hrs. The flammable portion was removed and the residue was dissolved in anhydrous methanol(7 ml) followed by addition of ammonium bicarbonate(240 mg, 2.1 mmol). After stirring at rt for 5 hrs, the mixture was concentrated and purified by flush chromatography over silica gel using a mixture of methylene chloride and methanol to give a white amorphous solid(220 mg, 56% yield). Further purification by reversed phase HPLC using water and 0.1% TFA in acetonitrile as eluent gave the TFA salt. $^1$H NMR(300 MHz, DMSO-$d_6$) $\delta$0.88(t, J=6, 3H), 1.30(m, 2H), 1.50(m, 2H), 3.40(m, 2H), 3.60(s, 3H), 3.94(t, J=6, 2H), 4.01(m, 1H), 4.20(s, 2H), 7.56(s, broad, 1H), 7.98(d,J=8, 2H), 8.2(d, J=8, 2H), 8.70(m, 1H), 9.42(s, 1H), 9.58(s, 2H); MS(ESI) Calc. for (M+1)$^+$: 463. Found: 463.

EXAMPLE 2

$N^3$-[2-{2-(4-amidinophenyl)-1,3,4-thiadiazol-5-yl}-acetyl]-$N^2$-(n-butyloxycarbonyl)-2,3-(S)-diaminopropionic acid HCl salt A solution of methyl $N^3$-[2-{2-(4-amidinophenyl)-1,3,4-thiadiazol-5-yl}-acetyl]$N^2$-(n-butyloxycarbonyl)-2,3-(S)-diaminopropionate(110 mg, 0.24 mmol) in 4N HCl(6 ml) was stirred at rt for 48 hrs. Evaporation under reduced pressure and purification by reversed phase HPLC gave the acid salt(98 mg, 85% yield). $^1$H NMR(300 MHz, DMSO-$d_6$) $\delta$0.88(t, J=6, 3H), 1.30(m, 2H), 1.50(m, 2H), 3.40(m, 2H), 3.94(t, J=6, 2H), .01(m, 1H), 4.20(s, 2H), 7.56(s, broad, 1H), 7.98(d,J=8, 2H), 8.2(d, J=8, 2H), 8.70(m, 1H), 9.42(s, 1H), 9.58(s, 2H); MS(ESI) Calc. for (M+1)$^+$: 449. Found: 449.

EXAMPLE 25

Methyl $N^3$-[2-{2-(4-amidinophenyl)-1,3,4-thiadiazol-5-yl}-acetyl]-$N^2$-(3-methylphenylsulfonyl)-2,3-(S)-diaminopropionate TFA salt Part A. Methyl $N^2$-3-methylphenylsulfonyl-$N^3$-Boc-(S)-2,3-diaminopropionate.

To a mixture of methyl $N^3$-BOC-(S)-2,3-diaminopropionate HCO$_2$H salt (3.8 g, 14.7 mmol) and diisoproppylethylamine (3.3 g, 32.3 mmol) in CH$_2$Cl$_2$(60 ml), cooled with ice-water, was added 3-methylsulfonyl chloride (3.1 g, 16.2 mmol). After stirring at rt for 24 hrs, the resulting reaction mixture was diluted with ethyl acetate(150 ml), washed with dilute citric acid, saturated NaHCO$_3$ and brine, and then dried. Concentration afforded the product as a foam(5.1 g, 95% yield). $^1$H NMR(300 MHz, CDCl$_3$) $\delta$1.58(s, 9H), 2.30(s, 3H), 2.72(m, 1H), 2.98(m, 1H), 4.10 (m, 1H), 5.80(s, 1H), 7.40(d, J=5, 2H), 7.50(m, 1H), 7.56(s, 1H), 8.40(d, J=6, 1H); MS(NH$_3$-CI) Calc. for (M+1)$^+$: 373. Found: 373.

Part B. Methyl $N^2$-3-methylphenylsulfonyl-(S)-2,3-diaminopropionate HCl salt

Methyl $N^2$-3-methylphenylsulfonyl-$N^3$-Boc-(S)-2,3-diaminopropionate(4.5 g, 12.1 mmol) was dissolved in dioxane(8 ml) and then 4N HCl in dioxane(8 ml) was added. The resulting solution was stirred at rt for 5 hrs and then evaporated to give a foam(3.7 g, 100% yield). $^1$H NMR(300 MHz, DMSO-$d_6$) $\delta$2.40(s, 3H), 2.86(m, 1H), 3.10(m, 1H), 3.40(s, 3H), 4.28(m, 1H), 7.48(d,J=5 2H), 7.60(m, 1H), 7.62(s, 1H) 8.39(s, broad, 2H), 8.62(d, J=6, 1H); MS(ESI) Calc. for (M+1)$^+$: 273. Found: 273(free base).

Part C. Methyl $N^3$-[2-{2-(4-cyanophenyl)-1,3,4-thiadiazol-5-yl}acetyl]-$N^2$-(3-methylphenylsulfonyl)-2,3-(s)-diaminopropionate To a mixture of 2-{2-(4-cyanophenyl)-1,3,4-thiadiazol-5-yl}acetic acid(1.13 g, 4.61 mmol), methyl $N^2$-3-methylphenylsulfonyl-(S)-2,3-diaminopropionate HCl salt (1.42 g, 4.61 mmol) and triethylamine(1.87 g, 18.4 mmol) in DMF(15 ml), cooled with ice-water, was added TBTU(1.48 mg, 4.61 mmol). After stirring for 3 hrs, the reaction mixture was diluted with ethyl acetate and washed with dilute citric acid, dilute NaHCO$_3$ and brine successively, then dried. Concentration followed by chromatography with ethyl acetate as the eluent gave the product as an amorphous solid(1.5 g, 65% yield). $^1$H NMR(300 MHz, CDCl$_3$) $\delta$2.40 (s, 3H), 3.58(m, 1H), 3.60(s, 3H), 3.78(m, 1H), 4.10(m, 1H), 4.20(s, 2H), 5.80(s, broad, 1H), 7.10(s, broad, 1H), 7.40(d, J=5, 2H), 7.60(m, 1H), 7.64(s, 1H), 7.80(d, J=8, 2H), 8.10(d, J=8, 2H); MS(NH$_3$-CI) Calc. for (M+1)$^+$: 500. Found: 500.
Part D. Methyl N$^3$-[2-{2-(4-amidinophenyl)-1,3,4-thiadiazol-5-yl}-acetyl]-N$^2$-(3-methylphenylsulfonyl)-2,3-(S)-diaminopropionate TFA salt Dry HCl gas was bubled through a solution of methyl N$^3$-[2-{2-(4-cyanophenyl)-1,3,4-thiadiazol-5-yl}acetyl]-N$^2$-(3-methylphenylsulfonyl)-2,3-(S)-diaminopropionate (510 mg, 1.02 mmol) in dry CHCl$_3$ containing anhydrous methanol(40 mg, 1.2 mmol), cooled with salt an ice-water bath, at 0° C. for 5 hrs. The resulting solution was then kept at 0° C. for 6 hrs and at 15° C. for 12 hrs. The flammable portion was removed and the residue was dissolved in anhydrous methanol(8 ml) followed by addition of ammonium bicarbonate(200 mg, 2.0 mmol). After stirring at rt for 4 hrs, the mixture was concentrated and purified by flush chromatography over silica gel using a mixture of methylene chloride and methanol to give a white amorphous solid(480 mg, 91% yield). Further purification by reversed phase HPLC using water and 0.1% TFA in acetonitrile as eluent gave the TFA salt. $^1$H NMR(300 MHz, DMSO-d$_6$) δ2.34(s, 3H), 3.23(m, 1H), 3.38(s, 3H), 3.40(m, 1H), 3.90–4.10(m, 3H), 7.40(m, 2H), 7.58(m, 2H), 8.00(d, J=8, 2H), 8.20(d, J=8, 2H), 8.46(d, J=8, 1H), 8.82(t, J=6, 1H), 9.56(s, 1H), 9.62(s, 2H); MS(ESI) Calc. for (M+1)$^+$: 517. Found: 517.

EXAMPLE 26

N$^3$-[2-{2-(4-amidinophenyl)-1,3,4-thiadiazol-5-yl}-acetyl]-N$^2$-(3-methylphenylsulfonyl)-2,3-(S)-diaminopropionic acid HCl salt A solution of methyl N$^3$-[2-{2-(4-amidinophenyl)-1,3,4-thiadiazol-5-yl}-acetyl]-N$^2$-(3-methylphenylsulfonyl)-2,3-(S)-diaminopropionate(100 mg, 0.19 mmol) in 6N HCl(4 ml) was stirred at rt for 20 hrs. Evaporation under reduced pressure and purification by reversed phase HPLC gave the acid salt(90 mg, 87% yield). $^1$H NMR(300 MHz, DMSO-d$_6$) δ2.30(s, 3H), 3.10(m, 1H), 3.34(m, 1H), 3.94–4.10(m, 3H), 7.38(m, 2H), 7.56(m, 2H), 8.00(d, J=8, 2H), 8.18(d, J=8, 2H), 8.40(d, J=8, 1H), 8.80(t, J=6, 1H), 9.50(s, 1H), 9.62(s, 2H); MS(ESI) Calc. for (M+1)$^+$: 503. Found: 503(free base).

EXAMPLE 44

Methyl N$^3$-[2-{2-(4-N-methylamidinophenyl)-1,3,4-thiadiazol-5-yl}-acetyl]-N$^2$-(3-methylphenylsulfonyl)-2,3-(S)-diaminopropionate TFA salt Dry HCl gas was bubled through a solution of methyl N$^3$-[2-{2-(4-cyanophenyl)-1,3,4-thiadiazol-5-yl}acetyl]-N$^2$-(3-methylphenylsulfonyl)-2,3-(S)-diaminopropionate (400 mg, 0.80 mmol) in dry CHCl$_3$ containing anhydrous methanol(79 mg, 2.4 mmol), cooled with a salt ice-water bath, at 0° C. for 5 hrs. The resulting solution was then kept at 0° C. for 6 hrs and at 15° C. for 12 hrs. The flammable portion was removed and the residue was dissolved in anhydrous methanol(7 ml) followed by addition of 2N methylamine in methanol(0.8 ml, 1.6 mmol). After stirring at rt for 2 hrs, the mixture was concentrated and purified by flush chromatography over silica gel using a mixture of methylene chloride and methanol to give a yellow amorphous solid(325 mg, 77% yield). Further purification by reversed phase HPLC using water and 0.1% TFA in acetonitrile as eluent gave the TFA salt. $^1$H NMR(300 MHz, DMSO-d$_6$) δ1.90(s, 3H), 2.36(s, 3H), 3.20(m, 1H), 3.38(s, 3H), 3.42(m, 1H), 3.90–4.10(m, 3H), 7.40(m, 2H), 7.58(m, 2H), 7.90(d, J=8, 2H), 8.20(d, J=8, 2H), 8.40(d, J=8, 1H), 8.70(t, J=4, 1H); MS(ESI) Calc. for (M+1)$^+$: 531. Found: 531.

EXAMPLE 63

N$^3$-[2-{2-(4-N-methylamidinophenyl)-1,3,4-thiadiazol-5-yl}-acetyl]-N$^2$-(3-methylphenylsulfonyl)-2,3-(S)-diaminopropionic acid HCl salt A solution of methyl N$^3$-[2-{2-(4-N-methylamidinophenyl)-1,3,4-thiadiazol-5-yl}-acetyl]-N$^2$-(3-methylphenylsulfonyl)-2,3-(S)-diaminopropionate(100 mg, 0.19 mmol) in 4N HCl(3 ml) was stirred at rt for 50 hrs. Evaporation under reduced pressure and purification by reversed phase HPLC gave the acid salt(71 mg, 68% yield). $^1$H NMR(300 MHz, DMSO-d$_6$) δ2.00(s, 3H), 2.40(s, 3H), 3.26(m, 1H), 3.40(m, 1H), 3.90–4.10(m, 3H), 7.38(m, 2H), 7.60(m, 2H), 8.00(d, J=8, 2H), 8.30(d, J=8, 2H), 8.40(d, J=6, 1H), 8.80(t, J=4, 1H); MS(ESI) Calc. for (M+1)$^+$: 517. Found: 517(free base).

EXAMPLE 64

Methyl N$^3$-[2-{2-(4-N-n-butylamidinophenyl)-1,3,4-thiadiazol-5-yl}-acetyl]-N$^2$-(3-methylphenylsulfonyl)-2,3-(S)-diaminopropionate TFA salt This compound was prepared analogously to Example 44. $^1$H NMR(300 MHz, DMSO-d$_6$) δ0.96(t, J=6, 3H), 1.40 (m, 4H), 1.60(t, J=6, 2H), 2.34(s, 3H), 3.36(m, 1H), 3.38(s, 3H), 3.40(m, 1H), 3.98(m, 1H), 4.02(d, J=16, 1H), 4.10(d, J=16, 1H), 7.40(m, 2H), 7.56(m, 2H), 7.90(d, J=8, 2H), 8.10(d, J=16, 2H), 8.60(d, J=6, 1H), 8.76(t, J=5, 1H); MS(ESI) Calc. for (M+1)$^+$: 573. Found: 573.

EXAMPLE 65

N$^3$-[2-{2-(4-N-n-butylamidinophenyl)-1,3,4-thiadiazol-5-yl}-acetyl]-N$^2$-(3-methylphenylsulfonyl)-2,3-(S)-diaminopropionic acid HCl salt A solution of methyl N$^3$-[2-{2-(4-N-butylamidinophenyl)-1,3,4-thiadiazol-5-yl}-acetyl]-N$^2$-(3-methylphenylsulfonyl)-2,3-(S)-diaminopropionate(300 mg, 0.52 mmol) in 4N HCl(9 ml) was stirred at rt for 45 hrs. Evaporation under reduced pressure and purification by reversed phase HPLC gave the acid salt(246 mg, 79% yield). MS(ESI) Calc. for (M+1)$^+$: 559. Found: 559.

EXAMPLE 88

Methyl N$^3$-[2-{2-(4-amidinophenyl)-1,3,4-thiadiazol-5-yl}-acetyl]-N -(2-methylphenylsulfonyl)-2,3-(S)-diaminopropionate TFA salt
Part A. Methyl N$^2$-2-methylphenylsulfonyl-N$^3$-Boc-(S)-2,3-diaminopropionate.

To a mixture of methyl N$^3$-Boc-(S)-2,3-diaminopropionate HCO$_2$H salt (2.58 g, 10 mmol) and diisoproppylethylamine(2.2 g, 22 mmol) in CH$_2$Cl$_2$(50 ml), cooled with ice-water, was added 2-methylsulfonyl chloride (2.1 g, 11 mmol). After stirring at rt for 24 hrs, the resulting reaction mixture was diluted with ethyl acetate(120 ml), washed with dilute citric acid, saturated NaHCO$_3$ and brine, and then dried. Concentration afforded the product as a foam(3.3 g, 90% yield). $^1$H NMR(300 MHz, CDCl$_3$) δ1.42 (s, 9H), 2.68(s, 3H), 3.48(m, 2H), 3.58(s, 3H), 3.92(m, 1H), 4.94(s, broad, 1H), 5.79(d, J=5, 2H), 7.30(m, 2H), 7.45(t J=7, 1H), 7.94(d, J=7, 1H); MS(NH$_3$-CI) Calc. for (M+1)$^+$: 373. Found: 373.
Part B. Methyl N$^3$-2-methylsulfonyl-(S)-2,3-diaminopropionate HCl salt Methyl N$^2$-2-methylphenylsulfonyl-N$^3$-Boc-(S)-2,3-diaminopropionate(3.5 g, 9.4 mmol) was dissolved in dioxane(8 ml) and then 4N HCl in dioxane(8 ml) was added. The resulting solution was stirred at rt for 5 hrs and then evaporated to give a foam(2.9 g, 100% yield). MS(ESI) Calc. for (M+1)$^+$: 273. Found: 273(free base).

Part C. Methyl N$^3$-[2-{2-(4-cyanophenyl)-1,3,4-thiadiazol-5-yl}acetyl]-N$^2$-(2-methylphenylsulfonyl)-2,3-(s)-diaminopropionate To a mixture of 2-{2-(4-cyanophenyl)-1,3,4-thiadiazol-5-yl}acetic acid(1.13 g, 4.61 mmol), methyl N$^2$-2-methylphenylsulfonyl-(S)-2,3-diaminopropionate HCl salt (1.42 g, 4.6 mmol) and triethylamine(1.87 g, 18.4 mmol) in DMF(15 ml), cooled with ice-water, was added TBTU(1.48 mg, 4.61 mmol). After stirring for 3 hrs, the reaction mixture was diluted with ethyl acetate and washed with dilute citric acid, dilute NaHCO$_3$ and brine successively, then dried. Concentration followed by chromatography with ethyl acetate as the eluent gave the product as an amorphous solid(1.6 g, 70% yield). $^1$H NMR(300 MHz, CDCl$_3$) δ2.64 (s, 3H), 3.58(m, 1H), 3.60(s, 3H), 3.76(m, 1H), 4.00(m, 1H), 4.20(s, 2H), 5.80(s, broad, 1H), 7.00(s, broad, 1H), 7.32(m, 2H), 7.44(t,J=6, 1H), 7.79(d, J=8, 2H), 7.90(d, J=6, 1H), 8.10(d, J=8, 2H); MS(NH$_3$-CI) Calc. for (M+1)$^+$: 500. Found: 500.

Part D. Methyl N$^3$-[2-{2-(4-amidinophenyl)-1,3,4-thiadiazol-5-yl}-acetyl]-N$^2$-(2-methylphenylsulfonyl)-2,3-(s)-diaminopropionate TFA salt An analogous procedure to that of Part K in Example 1 was applied to prepare this compound. $^1$H NMR(300 MHz, CDCl$_3$) δ2.80(s, 3H), 3.28(m, 1H), 3.34(s, 3H), 3.44(m, 1H), 3.96(m, 1H), 4.00(d, J=16, 1H), 4.10(d, J=16, 1H), 7.30(m, 2H), 7.44(t, J=7, 1H), 7.78(d, J=7, 1H), 8.00(d, J=8, 2H), 8.20(d, J=8, 2H), 8.50(d, J=6, 1H), 8.78(t, J=5, 1H), 9.46(s broad, 2H), 9.60(s, broad, 1H); MS(ESI) Calc. for (M+1)$^+$: 517. Found: 517.

EXAMPLE 89

N$^3$-[2-{2-(4-amidinophenyl)-1,3,4-thiadiazol-5-yl}-acetyl]-N$^2$-(2-methylphenylsulfonyl)-2,3-(S)-diaminopropionate acid HCl salt This compound was prepared analogously to Example 2. MS(ESI) Calc. for (M+1)+: 503. Found: 503.

EXAMPLE 96

Methyl N$^3$-[2-{2-(4-amidinophenyl)-1,3,4-thiadiazol-5-yl}-acetyl]-N$^2$-(3,5-dimethylisoxazol-4-ylsulfonyl)-2,3-(S)-diaminopropionate TFA salt Part A. Methyl N$^2$-(3,5-dimethylisoxazol-4-ylsulfonyl)-N$^3$-Boc-(S)-2,3-diaminopropionate.

This material was synthesized analogously to the product of Part A in Example 25 from methyl N$_3$-Boc-(S)-2,3-diaminopropionate HCO$_2$H salt and 3,5-dimethylisoxazol-4-ylsulfonyl chloride. $^1$H NMR (300 MHz, CDCl$_3$) δ1.44(S, 9H), 2.40(s, 3H), 2.62(s, 3H), 3.48(m, 2H), 3.50(s, 3H), 3.98(m, 1H), 4.94(s, broad, 1H), 5.98(d, J=8, 1H); MS(NH$_3$-CI) Calc. for (M+1)$^+$: 378. Found: 378.

Part B. Methyl N$^2$-(3,5-dimethylisoxazol-4-ylsulfonyl)-(S)-2,3-diaminopropionate HCl salt This material was prepared analogously to the product of Part B in Example 25 from methyl N$^2$-(3,5-dimethylisoxazol- 4-ylsulfonyl)-N$^3$-Boc-(S)-2,3-diaminopropionate. MS(ESI) Calc. for (M+1)+: 278. Found: 278(free base).

Part C. Methyl N$^3$-[2-{2-(4-cyanophenyl)-1,3,4-thiadiazol-5-yl}acetyl]-N$^2$-(3,5-dimethylisoxazol-4-ylsulfonyl)-2,3-(S)-diaminopropionate This material was prepared analogously to the product of Part J in Example 1 from 2-[2-(4-cyanophenyl)-1,3,4-thiadiazol-5-yl]acetic acid and methyl N$^2$-(3,5-dimethylisoxazol-4-ylsulfonyl)-(S)-2,3-diaminopropionate HCl salt. $^1$H NMR(300 MHz, CDCl$_3$) δ2.40(s, 3H), 2.60(s 3H), 3.60(m, 1H), 3.65(s, 3H), 3.80(m, 1H), 4.10(m, 1H), 4.22(s, 2H), 6.28(d, J=8, 1H), 7.44(t, J=5, 1H), 7.80(d, J=8, 2H), 8.10(d, J=8, 2H); MS(NH$_3$-CI) Calc. for (M+1)$^+$: 505. Found: 505.

Part D. Methyl N$^3$-[2-{2-(4-amidinophenyl)-1,3,4-thiadiazol-5-yl}-acetyl]-N$^2$-(3,5-dimethylisoxazol-4-ylsulfonyl)-2,3-(S)-diaminopropionate TFA salt An analogous procedure to that of Part K in Example 1 was applied to prepare this compound. $^1$H NMR(300 MHz, DMSO-d$_6$) δ2.34(s, 3H), 2.56(s, 3H), 3.30(m, 1H), 3.42(m, 1H). 3.48(s, 3H), 4.0(m, 1H), 4.10(d, J=16, 1H), 4.16(d, J=16, 1H), 8.00(d J=8, 2H), 8.20(d, J=8, 2H), 8.76(t, J=5, 1H); MS(ESI) Calc. for (M+1)$^+$: 522. Found: 522.

EXAMPLE 97

N$^3$-[2-{2-(4-amidinophenyl)-1,3,4-thiadiazol-5-yl}-acetyl]-N$^2$-(3,5-dimethylisoxazol-4-ylsulfonyl)-2,3-(S)-diaminopropionic acid HCl salt This compound was prepared analogously to Example 2. MS(ESI) Calc. for (M+1)$^+$: 508. Found: 508.

EXAMPLE 104

Methyl N$^3$-[2-{2-(4-piperidinyl)-1,3,4-thiadiazol-5-yl}acetyl]-N$^2$-(3-methylphenylsulfonyl)-2,3-(S)-diaminopropionate TFA salt Part A. Ethyl 4-(N-triphenylmethyl)piperidinecarboxylate A mixture of ethyl 4-piperidinecarboxylate(10 g, 63.6 mmol), triphenylmethyl chloride(17.7 g, 63.6 mmol) and triethylamine(7.0 g, 69.7 mmol) in methylene chloride(150 ml) was stirred for 16 hrs at rt, and washed with dilute citric acid, saturated NaHCO$_3$ and brine, and then dried. Concentration gave a powder(24 g, 95% yield). $^1$H NMR(300 MHz, CDCl$_3$) δ1.22(t, J=6, 3H), 1.40(m, 2H), 1.70–2.20(m, 5H), 3.10(m, 1H), 4.10(q, J=6, 2H), 7.24(m, 15H); MS(NH$_3$-DCI) Calc. for (M+1)$^+$: 400. Found: 400.

Part B. 4-(N-triphenylmethyl)piperidinecarbonylhydrazine

Ethyl 4-(N-triphenylmethyl)piperidinecarboxylate(10 g, 25.1 mmol) was dissolved in hydrazine monohydrate(20 ml) and the resulting mixture was heated to reflux for 2 hrs. The excess hydrazine was removed under reduced pressure and the oily residue was pure enough for next reaction. MS(NH$_3$-CI) Calc. for (M+1)$^+$: 386. Found: 386.

Part C. N-{4-(N-triphenylmethyl)piperdinecarbonyl}-N'-2-methoxycarbonylacetyl)hydrazine This material was prepared analogously to the product of Part B in Example 1. $^1$H NMR(300 MHz, CDCl$_3$) δ1.40(m, 2H), 1.80(m, 2H), 2.10(m, 3H), 3.20(m, 2H), 3.40(s, 2H), 3.80(s, 3H), 7.20(m, 15H); MS(NH$_3$-CI) Calc. for (M+1)$^+$: 486. Found: 486.

Part D. Methyl 2-{2-(4-N-triphenylmethylpiperidinyl)-1.3.4-thiadiazol-5-yl}acetate This material was prepared analogously to the product of Part C of Example 1. $^1$H NMR(300 MHz, CDCl$_3$) δ1.58(m, 2H), 2.10(m, 4H), 2.96(m, 1H), 3.24(m, 2H), 3.80(s, 3H), 4.20(s, 2H), 7.40(m, 15H); MS(NH$_3$-CI) Calc. for (M+1)$^+$: 484. Found: 484.

Part E. 2-{2-(4-N-triphenylmethylpiperidinyl)-1,3,4-thiadiazol-5-yl}acetic acid

This material was prepared analogously to the product of part D in Example 1. $^1$H NMR(300 MHz, DMSO-d$_6$) δ1.58(m, 2H), 2.10(m, 4H), 2.96(m, 1H), 3.24(m, 2H), 4.20(s, 2H), 7.20–7.60(m, 15H); MS(NH$_3$-CI) Calc. for (M+1)$^+$: 470. Found: 470.

Part F. Methyl $N^3$-[2-{2-(4-N-triphenylmethylpiperidinyl)-1,3,4-thiadiazol-5-yl}acetyl]-$N^2$-(3-methylphenylsulfonyl)-2,3-(S)-diaminopropionate This material was prepared analogously to the product of part J in Example 1 from 2-{2-(4-N-triphenylmethylpiperidinyl)-1,3,4-thiadiazol-5-yl}acetic acid and methyl $N^2$-3-methylphenylsulfonyl-(S)-2,3-diaminopropionate HCl salt. $^1$H NMR(300 MHz, CDCl$_3$) δ1.52(m, 2H), 2.14(m, 4H), 2.40(s, 3H), 2.98(m, 1H), 3.24 (m, 2H), 3.58(m, 1H), 3.50(s, 3H), 3.68(m, 1H), 4.02(s, 2H), 4.10(m, 1H), 5.88(s, broad, 1H), 7.10–7.70(m, 19H); MS(NH$_3$-DCI) Calc. for (M+NH$_4$)$^+$: 741. Found: 741.

Part G. Methyl $N^3$-[2-{2-(4-piperidinyl)-1,3,4-thiadiazol-5-yl}-acetyl]-$N^2$-(3-methylphenylsulfonyl)-2,3-(S)-diaminopropionate TFA salt Methyl $N^3$-[2-{2-(4-N-triphenylmethylpiperidinyl)-1,3,4-thiadiazol-5-yl}-acetyl]-$N^2$-(3-methylphenylsulfonyl)-2,3-(S)-diaminopropionate(240 mg, 0.33 mmol) was dissolved in 10% acetic acid in methanol (20 ml) and resulting solution was heated to reflux for 30 mins. After evaporation, the residue was taken up in methanol (5 ml) and TFA(0.2 ml) and purified by reversed phase HPLC to give an oil(178 mg, 90% yield). $^1$H NMR(300 MHz, DMSO-d$_6$) δ1.84(m, 2H), 2.14(m, 4H), 2.36(s, 3H), 2.98(m, 1H), 3.24(m, 2H), 3.58(m, 1H), 3.50(s, 3H), 3.68(m, 1H), 4.02(s, 2H), 4.10(m, 1H), 5.88(s, broad, 1H), 7.24(m, 2H), 7.39(m, 1H), 7.41(s, 1H); MS(ESI) Calc. for (M+1)$^+$: 482. Found: 482.

EXAMPLE 133

Methyl $N^3$-[4-{2-(4-piperidinyl)-1,3,4-thiadiazol-5-yl}-butyryl]-$N^2$-(3-methylphenylsulfonyl)-2,3-(S)-diaminopropionate TFA salt Part A. N-{4-(N-triphenylmethyl)piperdinecarbonyl}-N'-4-methoxycarbonylbutyryl)hydrazine This material was prepared analogously to the product of Part B in Example 1 from 4-N-triphenylmethylpiperidinecarbonylhydrazine and 4-methoxycarbonylbutyryl chloride. $^1$H NMR(300 MHz, CDCl$_3$) δ1.40(m, 2H), 1.70=2.08(m, 5H), 2.30–2.48(m, 4H), 3.20(m, 2H), 3.66(s, 3H), 3.74(m, 1H), 7.10–7.50(m, 15H), 8.60(t, J=4, 1H), 8.86(t, J=4, 1H); MS(NH$_3$-DCI) Calc. for (M+NH$_4$)$^+$: 531. Found: 531.

Part B. Methyl 4-{2-(4-N-triphenylmethylpiperidinyl)-1,3,4-thiadiazol-5-yl}butyrate This material was prepared analogously to the product of Part C of Example 1. $^1$H NMR(300 MHz, CDCl$_3$) δ1.50(m, 2H), 2.10(m, 6H), 2.44(t, J=7, 2H), 2.94(m, 1H), 3.16(t, J=6, 2H), 3.24(m, 2H), 3.70(s, 3H), 7.10–7.50(m, 15H); MS(NH$_3$-CI) Calc. for (M+1)$^+$: 512. Found: 512.

Part C. 4-{2-(4-N-triphenylmethylpiperidinyl)-1,3,4-thiadiazol-5-yl}butyric acid This material was prepared analogously to the product of Part D in Example 1. $^1$H NMR(300 MHz, DMSO-d$_6$) δ1.44(m, 2H), 2.00(m, 6H), 2.34(t, J=6, 2H), 2.96(m, 1H), 3.08(t, J=6, 2H), 3.38(s, 2H), 7.10–7.50(m, 15H), 12.20(m, 1H); MS(NH$_3$-DCI) Calc. for (M+NH$_4$)$^+$: 498. Found: 498.

Part D. Methyl $N^3$-[4-{2-(4-N-triphenylmethylpiperidinyl)-1,3,4-thiadiazol-5-yl}-butyryl]-$N^2$-(3-methylphenylsulfonyl)-2,3-(S)-diaminopropionate This material was prepared analogously to the product of Part J in Example 1 from 4-{2-(4-N-triphenylmethylpiperidinyl)-1,3,4-thiadiazol-5-yl}butyric acid and methyl $N^2$-3-methylphenylsulfonyl-(S)-2,3-diaminopropionate HCl salt. $^1$H NMR(300 MHz, CDCl$_3$) δ1.52(m, 2H), 2.10(m, 6H), 2.24(t, J=6, 2H), 2.40(s, 3H), 2.98(m, 1H), 3.16(t, J=6, 2H), 3.24(m, 2H), 3.58(s, 3H), 3.62(m, 2H), 4.02(m, 1H), 6.06(d, J=8, 1H), 6.38(t, J=6, 1H), 7.10–7.70(m, 19H); MS(NH$_3$-DCI) Calc. for (M+1)$^+$: 752. Found: 752.

Part E. Methyl $N^3$-[4-{2-(4-piperidinyl)-1,3,4-thiadiazol-5-yl}butyryl]-$N^2$-(3-methylphenylsulfonyl)-2,3-(S)-diaminopropionate TFA salt This similar procedure as in Part G of Example 133 was adopted to prepare this compound. $^1$H NMR(300 MHz, DMSO-d$_6$) δ1.80(m, 2H), 2.14(m, 6H), 2.28(t, J=6, 2H), 2.38(s, 3H), 2.98(m, 1H), 3.16(t, J=6, 2H), 3.24(m, 2H), 3.58(s, 3H), 3.62(m, 2H), 4.02(m, 1H), 6.06(d, J=8, 1H), 6.38(t, J=6, 1H), 7.18(m, 2H), 7.30(m, 1H), 7.32(s, 1H); MS(ESI) Calc. for (M+1)$^+$: 510. Found: 510.

EXAMPLE 134

$N^3$-[4-{2-(4-piperidinyl)-1,3,4-thiadiazol-5-yl}-butyryl]-$N^2$-(3-methylphenylsulfonyl)-2,3-(S)-diaminopropionic acid TFA salt Methyl $N^3$-[4-{2-(4-piperidinyl)-1,3,4-thiadiazol-5-yl}butyryl]-$N^2$-(3-methylphenylsulfonyl)-2,3-(S)-diaminopropionate TFA salt(300 mg, 0.47 mmol) was dissolved in aqueous THF(15 ml) containing methanol(5 ml) and lithium hydroxide monohydrate(42 mg, 1 mmol). After stirring at rt for 12 hrs, the mixture was evaporated to dryness and the residue was taken up in methanol(5 ml) containing TFA(0.2 ml) and purified by reversed phase HPLC to afford an oil(250 mg, 86%). MS(ESI) Calc. for (M+1)$^+$: 496. Found: 496.

EXAMPLE 144

Methyl $N^3$-[2-{2-(4-N,N'-di(trifluoroethyl)amidinophenyl)-1,3,4-thiadiazol - 5-yl}-acetyl]-$N^2$-(3-methylphenylsulfonyl)-2,3-(S)-diaminopropionate Dry HCl gas was bubled through a solution of Methyl $N^3$-[2-{2-(4-cyanophenyl)-1,3,4-thiadiazol-5-yl}acetyl]-$N^2$-(3-methylphenylsulfonyl)-2,3-(S)-diaminopropionate (400 mg, 0.80 mmol) in dry CHCl$_3$ containing anhydrous methanol (38 mg, 1.2 mmol), cooled with salt ice-water bath, at 0 C. for 5 hrs. The resulting solution was then kept at 0 C. for 6 hrs and at 15 C. for 12 hrs. The flammable portion was removed and the residue was dissolved in anhydrous methanol(7 ml) followed by addition of trifluoroethylamine(200 mg, 2 mmol). After stirring at rt for 4 hrs, the mixture was concentrated and purified by flush chromatography over silica gel using a mixture of methylene chloride and methanol to give a white amorphous solid(305 mg, 56% yield). Further purification by reversed phase HPLC using a mixture of water and 0.1% TFA in acetonitrile gave the TFA salt. $^1$H NMR(300 MHz, DMSO-d$_6$) δ2.36(S, 3H), 3.24(m, 1H), 3.40(s, 3H), 3.44(m, 1H), 3.90–4.10(m, 7H), 7.20(m, 2H), 7.26(d, J=8, 2H), 7.34(m, 1H), 7.36(s, 1H), 7.42(d, J=8, 2H), 7.70(d, J=6, 1H), 8.20(m, 1H), 8.70(m, 1H); MS(ESI) Calc. for (M+1)$^+$: 681. Found: 681.

EXAMPLE 145

Methyl $N^3$-[2-{2-(4-guanidinophenyl)-1,3,4-thiadiazol-5-yl}-acetyl]-$N^2$-(3-methylphenylsulfonyl)-2,3-(S)-diaminopropionate TFA salt Part A. 4-Nitrobenzoylhydrazine This material was prepared analogously to 4-cyanobenzoylhydrazine from 4-nitrobenzene and hydrazine monohydrate. $^1$H NMR(300 MHz, CDCl$_3$) δ4.16(s, 2H), 7.40(s, broad, 1H), 7.94(d, J=8, 2H), 8.34(d,J=8, 2H); MS(NH$_3$-CI) Calc. for (M+1)$^+$: 182. Found: 182.

Part B. N-(4-nitrobenzoyl)-N'-(2-methoxycarbonylacetyl)hydrazine

This material was prepared analogously to the product of Part B in Example 1. $^1$H NMR(300 MHz, DMSO-d$_6$)

δ3.40(s, 2H), 3.70(s, 3H), 8.10(d, J=8, 2H), 8.40(d, J=8, 2H), 10.40(s, 1H), 10.90(s, 1H); MS(NH$_3$-CI) Calc. for (M+1)$^+$: 282. Found: 282.

Part C. Methyl 2-{2-(4-nitrophenyl)-1,3,4-thiadiazol-5-yl}acetate

This compound was prepared analogously to the product of Part C in Example 1. $^1$H NMR(300 MHz, CDCl$_3$) δ3.84(s, 3H), 4.30(s, 2H), 8.20(d, J=8, 2H), 8.40(d, J=8, 2H); MS(NH$_3$-CI) Calc. for (M+1)$^+$: 280. Found: 280.

Part D. 2-{2-(4-nitrophenyl)-1,3,4-thiadiazol-5-yl}acetic acid

This acid was prepared analogously to the product of Part D in Example 1. $^1$H NMR(300 MHz, DMSO-d$_6$) δ4.40(s, 2H), 8.30(d, J=8, 2H), 8.40(d, J=8, 2H), 13.20(s, 1H); MS(NH$_3$-CI) Calc. for (M+1)$^+$: 266. Found: 266.

Part E. Methyl N$^3$-[2-{2-(4-nitrophenyl)-1,3,4-thiadiazol-5-yl}acetyl]-N$^2$-(3-methylphenylsufonyl)-2,3-(S)-diaminopropionate This compound was prepared analogously to the product of Part J in Example 1. $^1$H NMR(300 MHz, CDCl$_3$) δ2.40(s, 3H), 3.58(s, 3H), 3.60(m, 1H), 3.80(m, 1H), 4.10(m, 1H), 4.22(s, 2H), 5.92(d, J=6, 1H), 7.26(s, broad, 1H), 7.38(d, J=5, 2H), 7.62(m, 2H), 8.16(d, J=8, 2H), 7.38(d, J=8, 2H); MS(NH$_3$-CI) Calc. for (M+1)$^+$: 520. Found: 520.

Part F. Methyl N$^3$-[2-{2-(4-aminophenyl)-1,3,4-thiadiazol-5-yl}acetyl]-N$^2$-(3-methylphenylsufonyl)-2,3-(S)-diaminopropionate The nitro compound obtained in Part D(200 mg, 0.4 mmol) dissolved in ethyl acetate containing 10% Pd/C(20 mg) was hydrogenated in a shaking bottle overnight under a hydrogen pressure of 50 psi. Filtration through Celite and concentration gave an oil(190 mg, 100% yield). 1H NMR (300 MHz, CDCl$_3$) δ2.40(s, 3H), 3.58(s, 3H), 3.60(m, 2H), 4.02(s, 2H), 4.10(m, 1H), 5.90(d, J=8, 1H), 6.70(d, J=8, 2H), 7.36(m, 3H), 7.62(m, 2H), 8.78(d, J=8, 2H); MS(NH$_3$-CI) Calc. for (M+1)$^+$: 590. Found: 590.

Part G. N,N'-Bis-tert-butoxycarbonylthiourea

This material was prepared according to the method of Iwanowicz, et al (Synthetic Commun. 1993, 23, 1443).

Part H. Methyl N$^3$-[2-{2-(4-N,N'-bis-tert-butoxycarbonylguanidinophenyl)-1,3,4-thiadiazol-5-yl}acetyl]-N$^2$-(3-methylphenylsulfonyl)-2,3-(S)-diaminopropionate A mixture of N,N'-bis-tert-butoxycarbonylthiourea(130 mg, 0.26 mmol), HgCl$_2$(110 mg, 0.4 mmol) and prydine(62 mg, 0.80 mmol) in dry DMF(2 ml), cooled with ice-water, was stirred for 15 mins followed by addition of Methyl N$^3$-[2-{2-(4-amminophenyl)-1,3,4-thiadiazol-5-yl}acetyl]-N$^2$-(3-methylphenylsulfonyl)-2,3-(S)-diaminopropionate (130 mg, 0.26 mmol). Stirring was continued for 24 hrs. After filtration through Celite, the filtrate was diluted with ethyl acetate and washed with brine, and then dried. The residue obtained after concentration was chromatographed over silica gel to give an amorphous solid(150 mg, 78% yield). $^1$H NMR(300 MHz, CDCl$_3$) δ1.54(s, 9H), 1.58(s, 9H), 2.40(s, 3H), 3.58(S, 3H), 3.42(m, 2H), 4.08(s, 2H), 4.10(m, 1H), 5.80(s, broad, 1H), 7.20(s, broad, 1H), 7.40(d, J=7, 2H), 7.64(m, 2H), 7.78(d, J=8, 2H), 7.90(d, J=8, 2H), 10.60(s, 1H), 11.65(s, 1H); MS(NH$_3$-CI) Calc. for (M+1)$^+$: 732. Found:732.

Part I. Methyl N$^3$-[2-{2-(4-guanidinophenyl)-1,3,4-thiadiazol-5-yl}-acetyl]-N$^2$-(3-methylphenylsulfonyl)-2,3-(S)-diaminopropionate TFA salt A solution of Methyl N$^3$-[2-{2-(4-N,N'-bis-tert-butoxycarbonylguanidinophenyl)-1,3,4-thiadiazol-5-yl}acetyl]-N$^2$-(3-methylphenylsufonyl)-2,3-(S)-diaminopropionate (100 mg, 0.14 mmol) in methylene chloride(3 ml) containing TFA(1 ml) was stirred at rt for 2 hrs. After evaporation, the residue was taken un in methanol(4 ml) and purified by HPLC to afford an oily product(75 mg, 85% yield). MS(ESI) Calc. for (M+1)$^+$: 532. Found: 532(free base).

EXAMPLE 146

N$^3$-[2-{2-(4-guanidinophenyl)-1,3,4-thiadiazol-5-yl}-acetyl]-N$^2$-(3-methylphenylsulfonyl)-2,3-(S)-diaminopropionic acid TFA salt This material was prepared analogously to Example 144. MS(ESI) Calc. for (M+1)$^+$: 518. Found: 518.

EXAMPLE 157

Methyl N$^3$-[2-{2-(4-N-hydroxyamidinophenyl)-1,3,4-thiadiazol-5-yl}-acetyl]-N$^2$-(3-methylphenylsulfonyl)-2,3-(S)-diaminopropionate TFA salt A mixture of methyl N$^3$-[2-{2-(4-cyanophenyl)-1,3,4-thiadiazol-5-yl}acetyl]-N$^2$-(3-methylphenylsulfonyl)-2,3-(s)-diaminopropionate(500 mg, 1 mmol), hydroxyamine hydrogen chloride (83 mg, 1.2 mmol) and triethylamine(120 mg, 1.2 mmol) in methanol(10 ml) was stirred at rt for 24 hrs. The solid was collected by filtration(430 mg, 80% yield). Further purification by reversed phase HPLC gave the TFA salt. $^1$H NMR(300 MHz, CDCl$_3$) δ2.40(s, 3H), 3.58(s, 3H), 3.62(m, 2H), 4.10(m, 3H), 4.94(1, 1H), 5.82(s, broad, 1H), 7.10(s, broad, 1H), 7.40(d, J=6, 2H), 7.64(m, 2H), 7.74(d, J=8, 2H), 7.96(d, J=8, 2H); MS(NH$_3$-CI) Calc. for (M+1)$^+$: 533. Found: 533.

EXAMPLE 170

Methyl N$^3$-[2-{2-(4-amidophenyl)-1,3,4-thiadiazol-5-yl}-acetyl]-N$^2$-(3-methylphenylsulfonyl)-2,3-(S)-diaminopropionate To a mixture of methyl N$^3$-[2-{2-(4-cyanophenyl)-1,3,4-thiadiazol-5-yl}acetyl]-N$^2$-(3-methylphenylsulfonyl)-2,3-(S)-diaminopropionate(200 mg, 0.4 mmol) and potassium bicarbonate(220 mg, 1.6 mmol) in DMSO(4 ml), cooled with ice-water, was added hydrogen peroxide(30%, 1 ml). After stirring at rt for 2 hrs, the reaction mixture was diluted with ethyl acetate and worked up as usual. The residue obtained after concentration was chromatographed over silica gel to give a powder solid(135 mg, 65% yield). $^1$H NMR(300 MHz, CDCl$_3$) δ2.38(s, 3H), 3.20(m, 1H), 3.36(s, 3H), 3.40(m, 1H), 4.00(m, 3H), 7.40(m, 2H), 7.52(m, 3H), 8.02(d, J=8, 2H), 8.08(d, J=8, 2H), 8.14(s, 1H), 8.42(d, J=8, 1H), 8.60(t, J=5, 1H); MS(ESI) Calc. for (M+1)$^+$: 518. Found: 518.

EXAMPLE 171

N$^3$-[2-{2-(4-Amidophenyl)-1,3,4-thiadiazol-5-yl}-acetyl]-N$^2$-(3-methylphenylsulfonyl)-2,3-(S)-diaminopropionic acid This material was prepared analogously to Example 2. MS(ESI) Calc. for (M+1)$^+$: 504. Found: 504.

EXAMPLE 192

Methyl N$^3$-[2-{2-(4-amidinophenyl)-1,3,4-thiadiazol-5-ylthio}acetyl]-N$^2$-(n-butoxycarbonyl)-2,3-(S)-diaminopropionate HCl salt Part A. Benzyldithiocarbhydrazide This compound was prepared according to the procedure of Busch and Starke (J. Prakt. Chem. 1916, 93, 49). $^1$H NMR(300 MHz, CDCl$_3$) δ4.10(s, 1H), 4.54(s, 1H), 4.70(s, 1H), 4.20–4.50(m, 5H).

Part B. Benzyl 3-(4-cyanobenzoyl)dithiocarbazinate

A mixture of 4-cyanobenzoyl chloride(3.31 g, 20 mmol) and benzyldithiocarbhydride(3.96 g, 20 mmol) in pyridine (20 ml) was heated at 80–90 C. for 1 hr, and then poured into ice water(140 ml) containing 15 ml of conc. H2SO4, extracted with ethyl acetate. The extract was washed with water (20 ml×2) and dried. After evaporation of the solvent, the solid was triturated with anhydrous ether and pumped to give the product as a white powder(4 g, 61% yield). $^1$H NMR(300 MHz, CDCl$_3$) δ4.58(s, 2H), 7.30–7.40(m, 5H), 7.80(d, J=8, 2H), 7.98(d, J=8, 2-H), 10.60(s, 2H); MS(NH$_3$-DCI) Calc for (M+NH$_4$)$^+$: 345. Found: 345.

Part C. 2-(4-Cyanophenyl)-5-benzylthio-1,3,4-thiadiazole

A mixture of benzyl 3-(4-cyanobenzoyl)dithiocarbazinate(1 g, 3.1 mmol) and 4-methylbenzenesulfonyl chloride(100 mg) in 25 ml of benzene was refluxed for 3 hrs. The solvent was removed under reduced pressure and the residue was recrystallized from ethyl acetate to afford a white solid(800 mg, 85% yield). $^1$H NMR(300 MHz, CDCl$_3$) δ4.62(s, 2H), 7.34(m, 3H), 7.48(d, J=6, 2H), 7.76(d, J=8, 2H), 8.00(d, J=8, 2H); MS(NH$_3$-CI) Calc. for (M+1)$^+$: 310. Found: 310.

Part D. 2-(4-Cyanophenyl)-5-benzylsulfonyl-1,3,4-thiadiazole

To a solution of 2-(4-Cyanophenyl)-5-benzylthio-1,3,4-thiadiazole(560 mg, 1.81 mmol) in acetic acid (7 ml) was slowly added an aqueous solution of KMnO$_4$(3%, 40 ml). After addition, the resulting mixture was heated at 60 C. for 2 hrs, and then poured into water. After decolorization with Na$_2$S$_2$O$_3$, the aqueous solution was filtered and the solid portion was recrystallized from ethanol to give a white solid(510 mg, 83% yield). $^1$H NMR(300 MHz, CDCl$_3$) δ4.84(s, 2H), 7.36(m, 5H), 7.82(d, J=8, 2H), 8.08(d, J=8, 2H); MS(NH$_3$-CI) Calc. for (M+1)$^+$: 342. Found: 342.

Part E. 2-{2-(4-Cyanophenyl)-1,3,4-thiadiazol-5-ylthio}acetic acid

A mixture of 2-(4-cyanophenyl)-5-benzylsulfonyl-1,3,4-thiadiazole(407 mg, 1.2 mmol), mercaptoacetic acid(110 mg, 1.2 mmol) and triethylamine(120 mg, 1.2 mmol) in ethanol(20 ml) was stirred at rt overnight. The solvent was evaporated and the residue was triturated with water, dried to afforded 290 mg of the product (88% yield). $^1$H NMR(300 MHz, CDCl$_3$) δ4.02(s, 2H), 8.00(d, J=8, 2H), 8.10(d, J=8, 2H); MS(NH$_3$-DCI) Calc. for (M+NH$_4$)$^+$: 295. Found: 295.

Part F. Methyl N$^3$-[2-{2-(4-cyanophenyl)-1,3,4-thiadiazol-5-ylthio}acetyl]-N$^2$-(n-butoxycarbonyl)-2,3-(S)-diaminopropionate A similar procedure to Part J in Example 1 was adopted to prepare this compound from 2-{2-(4-Cyanophenyl)-1,3,4-thiadiazol-5-ylthio}acetic acid and methyl N$^2$-butyloxycarbonyl-(S)-2,3-diaminopropionate TFA salt. $^1$H NMR(300 MHz, CDCl$_3$) δ0.90(t, J=7, 3H), 1.36(m, 2H), 1.58(m, 2H), 3.54(m, 1H), 3.74(s, 3H), 3.76(m, 1H), 3.90–4.10(m, 3H), 4.42(s, broad, 1H), 5.60(d, J=6, 1H), 7.78(d, J=8, 2H), 8.00(d, J=8, 2H); MS(NH$_3$-CI) Calc. for (M+1)$^+$: 478. Found: 478.

Part G. Methyl N$^3$-[2-{2-(4-amidinophenyl)-1,3,4-thiadiazol-5-ylthio}acetyl]-N$^2$-(n-butoxycarbonyl)-2,3-(S)-diaminopropionate HCl salt Dry HCl gas was bubled through a solution of Methyl N$^3$-[2-{2-(4-cyanophenyl)-1,3,4-thiadiazol-5-ylthio}acetyl]-N$^2$-(n-butoxycarbonyl)-2,3-(S)-diaminopropionate(260 mg, 0.55 mmol) in dry CHCl$_3$ containing anhydrous methanol(35 mg, 1.1 mmol), cooled with salt ice-water bath, at 0 C. for 5 hrs. The resulting solution was then kept at 0 C. for 6 hrs and at 15 C. for 12 hrs. The flammable portion was removed and the residue was dissolved in aqueous methanol(75%, 5 ml) containing ammonium chloride (110 mg, 2.2 mmol). After stirring at reflux for 2 hrs, the mixture was concentrated and purified by flush chromatography over silica gel using a mixture of methylene chloride and methanol to give an amorphous solid(180 mg, 62% yield). $^1$H NMR(300 MHz, CDCl$_3$) δ0.86(t, J=7, 3H), 1.30(m, 2H), 1.50(m, 2H), 3.50(m, 1H), 3.60(s, 3H), 3.90(t, J=8, 1H), 4.18(m, 3H), 8.04(d, J=8, 2H), 8.14(d, J=8, 2H), 8.66(t, J=5, 1H);MS(ESI) Calc. for (M+1)$^+$: 495. Found: 495(free base).

EXAMPLE 193

N$^3$-[2-{2-(4-Amidinophenyl)-1,3,4-thiadiazol-5-ylthio}acetyl]-N$^2$-(n-butoxycarbonyl)-2,3-(S)-diaminopropionic acid HCl salt A similar procedure to Example 134 was adopted to prepare this acid from Methyl N$^3$-[2-{2-(4-amidinophenyl)-1,3,4-thiadiazol-5-ylthio}acetyl]-N$^2$-(n-butoxycarbonyl)-2,3-(S)-diaminopropionate HCl salt. MS(ESI) Calc. for (M+1)$^+$: 481. Found: 481.

EXAMPLE 222

Methyl N$^3$-[2-{2-(4-aminophenyl)-1,3,4-oxadiazol-5-ylthio}acetyl]-N$^2$-(n-butoxycarbonyl)-2,3-(S)-diaminopropionate TFA salt Part A. Methyl 4-tert-butoxycarbonylaminobenzoate To a solution of methyl 4-aminobenzoate(5.2 g, 34 mmol) and (Boc)$_2$O(7.4 g 34 mmol) in methylene chloride(50 ml), cooled with ice water, was added one equivalent DMAP. After stirring overnight, the mixture was diluted with additional 50 ml of methylene chloride and washed with dilute citric acid, saturated NaHCO$_3$ and brine, dried. Removal of the solvent gave 4.5 g of the product. $^1$H NMR(300 MHz, CDCl$_3$) δ1.54(s, 9H), 3.88(s, 3H), 7.44(d, J=8, 2H), 7.98(d, J=8, 2H); MS(NH$_3$-CI) Calc. for (M+1)$^+$: 252. Found: 252.

Part B. 4-tert-Butoxycarbonylaminobenzoylhydrazine

A mixture of Methyl 4-tert-butoxycarbonylaminobenzoate (500 mg, 2 mmol) and hydrazine monohydrate(3 ml) was heated to reflux for 1 hr. The excess hydrazine was removed under reduced pressure and the residue was recrystallized from methanol to a solid(420 mg, 84% yield). $^1$H NMR(300 MHz, CDCl$_3$) δ1.56(s, 9H), 6.70(s, 2H), 7.35(s, 1H), 7.44(d, J=8, 2H), 7.70(d, J=8, 2H); MS(NH$_3$-CI) Calc. for (M+1)$^+$: 252. Found: 252.

Part C. 2-{2-(4-tert-butoxycarbonylaminophenyl)-1,3,4-oxadiazol-5-ylthio}acetic acid A mixture of 4-tert-Butoxycarbonylaminobenzoylhydrazine(820 mg, 3.3 mmol) and potassium hydroxide(217 mg, 3.3 mmol) in ethanol (95%, 20 ml) was stirred till all potassium hydroxide was dissolved. Carbon disulfide(280 mg, 3.6 mmol) was then introduced, and the solution gradually became pale yellow and some precipitate appeared. After stirring at reflux for 10 hrs, mercaptoacetic acid(460 mg, 3.3 mmol) was added and stirring was continued for 12 hrs at rt and 2 hrs at reflux. The solvent was removed and the residue was chromatographed over silica gel, affording 840 mg of the product(73% yield). $^1$H NMR(300 NHz, DMSO-d$_6$) δ1.50(s, 9H), 4.20(s, 2H), 7.68(d, J=8, 2H), 7.88(d, J=8, 2H), 9.82(s, 1H); MS(NH$_3$-DCI) Calc for (M+1)$^+$: 352. Found: 352.

Part D. Methyl N$^3$-[2-{2-(4-tert butoxycarbonylaminophenyl)-1,3,4-oxadiazol-5-ylthio}acetyl]-N$^2$-(n-butoxycarbonyl)-2,3-(S)-diaminopropionate A similar coupling reaction procedure to Part J in Example 1 was adopted to prepare this compound from 2-{2-(4-tert-butoxycarbonylaminophenyl)-1,3,4-oxadiazol-5-ylthio}acetic acid and methyl $N^2$-butyloxycarbonyl-(S)-2,3-diaminopropionate TFA salt. $^1$H NMR(300 MHz, CDCl$_3$) δ0.90(t, J=6, 3H), 1.38(m, 2H), 1.56(s, 9H), 1.58(m, 2H), 3.70(m, 2H), 3.74(s, 3H), 3.84(d, J=16, 1H), 3.92(d, J=16, 1H), 4.02(m, 3H), 4.42(s, broad, 1H), 5,62(s, broad, 1H), 6.68(s, s, 1H), 7.56(d, J=8, 2H), 7.94(d, J=8, 2H); MS(ESI) Calc. for (M+1)$^+$: 552. Found: 552.

Part E Methyl $N^3$-[2-{2-(4-aminophenyl)-1,3,4-oxadiazol-5-ylthio}acetyl]-$N^2$-(n-butoxycarbonyl)-2,3-(S)-diaminopropionate TFA salt A similar procedure to Part H in Example 145 was adopted to prepare this material from Methyl $N^3$-[2-{2-(4-tert-butoxycarbonylamino phenyl)-1,3,4-oxadiazol-5-ylthio}acetyl]-$N^2$-(n-butoxycarbonyl)-2,3-(S)-diaminopropionate. MS(ESI) Calc. for (M+1)$^+$: 452. Found: 452.

EXAMPLE 242

Methyl $N^3$-[2-{2-(4-guanidinophenyl)-1,3,4-oxadiazol-5-ylthio}acetyl]-$N^2$-(n-butoxycarbonyl)-2,3-(S)-diaminopropionate TFA salt Part A. Methyl N3-[2-{2-(4-N,N'-bis-tert-butoxycarbonylguanidinophenyl)-1,3,4-oxadiazol-5-ylthio}acetyl]-N2-(n-butoxycarbonyl)-2,3-(S)-diaminopropionate A mixture of N,N'-bis-tert-butoxycarbonylthiourea (85 mg, 0.31 mmol), HgCl$_2$(84 mg, 0.31 mmol) and prydine(25 mg, 0.31 mmol) in dry DMF(1 ml), cooled with ice-water, was stirred for 15 mins followed by addition of Methyl $N^3$-[2-{2-(4-aminophenyl)-1,3,4-oxadiazol-5-ylthio}acetyl]-$N^2$-(n-butoxycarbonyl)-2,3-(S)-diaminopropionate (70 mg, 0.16 mmol). Stirring was continued for 24 hrs. After filtration through Celite, the filtrate was diluted with ethyl acetate and washed with brine, and then dried. The residue obtained after concentration was chromatographed over silica gel to give an amorphous solid(87 mg, 81% yield). $^1$H NMR(300 MHz, CDCl$_3$) δ0.90(t, J=6,3H), 1.38(m, 2H), 1.54(s, 9H), 1.58(s, 9H), 1.60(m, 2H), 3.70(m, 2H), 3.72(s, 3H), 3.84(d, J=16, 1H), 3.92(d, J=16, 1H), 4.04(m, 3H), 4.44(s, broad 1H), 5.64(d, J=6, 1H), 7.46(t, J=4, 1H), 7.82(d, J=8, 2H), 7.96(d, J=8, 2H), 10.60(s, 1H), 11.65(s, 1H); MS(NH$_3$-CI) Calc. for (M+1)$^+$: 694. Found: 694.

Part B. Methyl $N^3$-[2-{2-(4-guanidinophenyl)-1,3,4-oxadiazol-5-ylthio}-acetyl]-$N^2$-(n-butoxycarbonyl)-2,3-(S)-diaminopropionate TFA salt A solution of Methyl $N^3$-[2-{2-(4-N,N'-bis-tert-butoxycarbonylguanidinophenyl)-1,3,4-oxadiazol-5-ylthio}acetyl]-$N^2$-(n-butoxycarbonyl)-2,3-(S)-diaminopropionate (70 mg, 0.10 mmol) in methylene chloride(3 ml) containing TFA(1 ml) was stirred at rt for 2 hrs. After evaporation, the residue was taken up in methanol(4 ml) and purified by HPLC to afford an oily product(45 mg, 90% yield). MS(ESI) Calc. for (M+1)$^+$: 494. Found: 494(free base).

EXAMPLE 258

Methyl $N^3$-[2-{2-(4-amidinophenyl)-1,3,4-oxadiazol-5-ylthio}-acetyl]-$N^2$-(n-butyloxycarbonyl)-2,3-(S)-diamino propionate HCl salt Part A. 2-{2-(4-cyanophenyl)-1,3,4-oxadiazol-5-ylthio}acetic acid A mixture of 4-cyanobenzoylhydrazine(3.22 g, 20 mmol) and potassium hydroxide(1.32 g, 20 mmol) in ethanol(95%, 100 ml) was stirred till all potassium hydroxide was dissolved. Carbon disulfide(1.67 g, 22 mmol) was then introduced. After stirring at reflux for 24 hrs, mercaptoacetic acid(2.78 g, 20 mmol) was added and stirring was continued for 16 hrs at rt. The solvent was removed and the residue was chromatographed over silica gel, affording 2.9 g of the product(56% yield). $^1$H NMR(300 NHz, DMSO-d$_6$) δ4.10 (s, 2H), 7.08(d, J=8, 2H), 7.16(d, J=8, 2H); MS(NH$_3$-DCI) Calc for (M+1)$^+$: 262. Found: 262.

Part B. Methyl $N^3$-[2-{2-(4-cyanophenyl)-1,3,4-oxadiazol-5-ylthio}acetyl]-$N^2$-(n-butoxycarbonyl)-2,3-(S)-diaminopropionate A similar coupling reaction procedure to Part J in Example 1 was adopted to prepare this compound from 2-{2-(4-cyanophenyl)-1,3,4-oxadiazol-5-ylthio}acetic acid and methyl $N^2$-butyloxycarbonyl-(S)-2,3-diaminopropionate TFA salt. $^1$H NMR(300 MHz, CDCl$_3$) δ0.90(t, J=6, 3H), 1.38(m, 2H), 1.58(m, 2H), 3.70(m,2H), 3.74(s, 3H), 3.90(d, J=16, 1H), 3.96(d, J=16, 1H), 4.02(m, 3H), 4.42(m, 1H), 5,60(d, J=5, 1H), 7.82(d, J=8, 2H), 7.16(d, J=8, 2H); MS(ESI) Calc. for (M+1)$^+$: 462. Found: 462.

Part C. Methyl $N^3$-[2-{2-(4-amidinophenyl)-1,3,4-oxadiazol-5-ylthio}-acetyl]-$N^2$-(n-butyloxycarbonyl-2,3-(S)-diaminopropionate HCl salt Dry HCl gas was bubled through a solution of Methyl $N^3$-[2-{2-(4-cyanophenyl)-1,3,4-oxadiazol-5-ylthio}acetyl]-$N^2$-(n-butoxycarbonyl)-2,3-(s)-diaminopropionate(250 mg, 0.54 mmol) in dry CHCl$_3$(8 ml) containing anhydrous methanol(21 mg, 0.65 mmol), cooled with salt ice-water bath, at 0 C. for 6 hrs. The resulting solution was then kept at 0 C. for 12 hrs and at 15 C. for 5 hrs. The flammable portion was removed and the residue was dissolved in aqueous methanol(75%, 5 ml) containing ammonium chloride(110 mg, 2.1 mmol). After stirring at reflux for 3 hrs, the mixture was concentrated and purified by flush chromatography over silica gel using a mixture of methylene chloride and methanol to give an amorphous solid(83 mg, 32% yield). $^1$H NMR(300 MHz, DMSO-d$_6$) δ0.90(t, J=7, 3H), 1.34(m, 2H), 1.52(m, 2H), 3.48(m, 2H), 3.60(s, 3H), 3.78(d, J=16, 1H), 3.92(d, J=16, 1H), 4.18(m, 3H), 7.98(d, J=8, 2H), 8.16(d, J=8, 2H); MS(ESI) Calc. for (M+1)$^+$: 478. Found: 478(free base).

EXAMPLE 290

Methyl $N^3$-[2-{2-(4-aminophenyl)-1,3,4-oxadiazol-5-yl}-acetyl]-$N^2$-(n-butyloxycarbonyl)-2,3-(S)-diaminopropionate Part A. Methyl 2-{2-(4-nitrophenyl)-1,3,4-oxadiazol-5-yl}acetate A mixture of N-(4-nitrobenzoyl)-N'-methoxycarbonylacetylhydrazine(the product of part B in Example 145)(1 g, 3.6 mmol) and phosphorus oxychloride (3.3 ml) in dry acetonitrile was heated to reflux for 2 hrs. The solvent was evaporated and the oily residue was taken up in ethyl acetate and worked up as usual. Chromatography afforded 950 mg of the product(930 mg, 100% yield). $^1$H NMR(300 MHz, CDCl$_3$) δ3.80(s, 3H), 4.10(s, 2H), 8.26(d, J=8, 2H), 8.40(d, J=8, 2H); MS(NH$_3$-CI) Calc. for (M+1)$^+$: 264. Found: 264.

Part B. 2-{2-(4-nitrophenyl)-1,3,4-oxadiazol-5-yl}acetic acid

A similar procedure to Part D of Example 1 was applied to prepare this acid. $^1$H NMR(300 MHz, DMSO-d$_6$) δ4.10(s, 2H), 8.26(d, J=8, 2H), 8.44(d, J=8, 2H); MS(NH$_3$-CI) Calc. for (M+1)$^+$: 250. Found: 250.

Part C. Methyl $N^3$-[2-{2-(4-nitrophenyl)-1,3,4-oxadiazol-5-yl}acetyl]-$N^2$-(n-butoxycarbonyl)-2,3-(S)-diaminopropionate A similar coupling reaction procedure to Part J of Example 1 was applied to prepare this compound from the acid of Part B and methyl $N^2$-butyloxycarbonyl-(S)-2,3-diaminopropionate TFA salt. $^1$H NMR(300 MHz, CDCl$_3$) δ0.90(t, J=6, 3H), 1.36(m, 2H), 1.58(m, 2H), 3.70(m, 2H), 3.80(s, 3H), 4.00(s, 2H), 4.06(m, 3H), 4.90(s, broad, 1H), 5.74(d, J=6, 1H), 8.26(d, J=8, 2H), 8.40(d, J=8, 2H); MS(NH$_3$-CI) Calc. for (M+1)$^+$: 450. Found: 450.

Part D. Methyl $N^3$-[2-{2-(4-aminophenyl)-1,3,4-oxadiazol-5-yl}acetyl]-$N^2$-(n-butoxycarbonyl)-2,3-(S)-diaminopropionate The nitro compound obtained in Part C(85 mg, 0.19 mmol) dissolved in ethyl acetate(20 ml) containing 10% Pd/C(10 mg) was hydrogenated in a shaking bottle overnight under a hydrogen pressure of 50 psi. Filtration through Celite and concentration gave an oil(81 mg, 100% yield). $^1$H NMR(300 MHz, CDCl$_3$) δ0.90(t, J=6, 3H), 1.38(m, 2H), 1.60(m, 2H), 3.78(m, 2H), 3.80(s, 3H), 3.90(s, 2H), 4.06(m, 3H), 4.50(s,broad, 1H), 5.70(d, J=6, 1H), 6.76(d, J=8, 2H), 7.80(d, J=8, 2H); MS(NH$_3$-CI) Calc. for (M+1)$^+$: 430. Found: 430.

EXAMPLE 318

Methyl $N^3$-[2-{2-(4-amidinophenyl)-1,3,4-oxadiazol-5-yl}-acetyl]-$N^2$-(n-butyloxycarbonyl)-2,3-(S)-diaminopropionate TFA salt Part A. Methyl 2-{2-(4-cyanophenyl)-1,3,4-oxadiazol-5-yl}acetate This material was anologously prepared to the product of Part A of Example 290 from 4-cyanobenzoylhydrazine(the product of Part A of Example 1). $^1$H NMR(300 MHz, CDCl$_3$) δ3.80(s, 3H), 4.10(s, 2H), 7.80(d, J=8, 2H), 8.20(d, J=8, 2H); MS(NH$_3$-CI) Calc. for (M+1)$^+$: 244. Found: 244.

Part B. 2-{2-(4-cyanophenyl)-1,3,4-oxadiazol-5-yl}acetic acid

A similar procedure to Part D of Example 1 was applied to prepare this acid. $^1$H NMR(300 MHz, DMSO-d$_6$) δ4.20 (s, 2H), 8.08(d, J=8, 2H), 8.18(d, J=8, 2H); MS(NH$_3$-DCI) Calc. for (M+1)$^+$: 230. Found: 230.

Part C. Methyl $N^3$-[2-{2-(4-cyanophenyl)-1,3,4-oxadiazol-5-yl}acetyl]-$N^2$-(n-butoxycarbonyl)-2,3-(S)-diaminopropionate A similar coupling reaction procedure to Part J of Example 1 was applied to prepare this compound from the acid obtained from Part B and methyl $N^2$-butyloxycarbonyl-(S)-2,3-diaminopropionate TFA salt. $^1$H NMR(300 MHz, CDCl$_3$) δ0.94(t, J=6, 3H), 1.36(m, 2H), 1.58(m, 2H), 3.68 (m, 2H), 3.80(s, 3H), 3.98(s, 2H), 4.06(m, 3H). 4.46(s, broad, 1H), 5.68(d, J=6, 1H), 7.80(d, J=8, 2H), 8.20(d, J=8, 2H); MS(NH$_3$-CI) Calc. for (M+1)$^+$: 430. Found: 430.

Part D. Methyl $N^3$-[2-{2-(4-amidinophenyl)-1,3,4-oxadiazol-5-yl}acetyl]-$N^2$-(n-butoxycarbonyl)-2,3-(S)-diaminopropionate TFA salt Dry HCl gas was bubled through a solution of Methyl $N^3$-[2-{2-(4-cyanophenyl)-1,3,4-oxadiazol-5-yl}acetyl]-$N^2$-(n-butyloxycarbonyl)-2,3-(S)-diaminopropionate(750 mg, 1.75 mmol) in dry CHCl$_3$(15 ml) containing anhydrous methanol (76 mg, 2.1 mmol), cooled with salt ice-water bath, at 0 C. for 5 hrs. The resulting solution was then kept at 0 C. for 12 hrs and at 15 C. for 5 hrs. The flammable portion was removed and the residue was dissolved in anhydrous methanol(12 ml) followed by addition of ammonium bicarbonate(504 mg, 5.25 mmol). After stirring at rt for 4 hrs, the mixture was concentrated and purified by flush chromatography over silica gel using a mixture of methylene chloride and methanol to give an amorphous solid(273 mg, 35% yield). Further purification gave the TFA salt. $^1$H NMR(300 MHz, DMSO-d$_6$) δ0.90(t, J=6, 3H), 1.32(m, 2H), 1.58(m, 2H), 3.40(m, 2H), 3.60(s, 3H), 3.94(t, J=6, 2H), 4.01(m, 1H), 4.20(s, 2H), 7.56(s, broad, 1H), 7.60(d,J=8, 2H), 8.08(d, J=8, 2H), 8.70(m, 1H), 9.40(s, 1H), 9.60(s, 2H); MS(ESI) Calc. for (M+1)$^+$: 447. Found: 447.

EXAMPLE 335

Methyl $N^3$-[2-{2-(4-guanidinophenyl)-1,3,4-oxadiazol-5-yl}-acetyl]-N2-(n-butyloxycarbonyl)-2,3-(S)-diaminopropionate TFA salt Part A. Methyl $N^3$-[2-{2-(4-N,N'-bis-tert-butoxycarbonylguanidinophenyl)-1,3,4-oxadiazol-5-yl}acetyl]-$N^2$-(n-butoxycarbonyl)-2,3-(S)-diaminopropionate A mixture of N,N'-bis-tert-butoxycarbonylthiourea(92 mg, 0.33 mmol), HgCl$_2$(91 mg, 0.33 mmol) and prydine(26 mg, 0.33 mmol) in dry DMF(1 ml), cooled with ice-water, was stirred for 15 mins followed by addition of Methyl $N^3$-[2-{2-(4-aminophenyl)-1,3,4-oxadiazol-5-yl}acetyl]-$N^2$-(n-butoxycarbonyl)-2,3-(S)-diaminopropionate(70 mg, 0.17 mmol). Stirring was continued for 24 hrs. After filtration through Celite, the filtrate was diluted with ethyl acetate and washed with brine, and then dried. The residue obtained after concentration was chromatographed over silica gel to give an amorphous solid(95 mg, 86% yield). $^1$H NMR(300 MHz, CDCl$_3$) δ0.90(t, J=6.3H), 1.38(m, 2H), 1.54(s, 9H), 1.58(s, 9H), 1.60(m, 2H), 3.74(m, 2H), 3.78(s, 3H), 3.94(s, 2H), 4.04(m, 3H), 4.44(s, broad, 1H), 5.68(d, J=6, 1H), 7.52(t, J=4, 1H), 7.82(d, J=8, 2H), 7.02(d, J=8, 2H), 10.65(s, 1H), 11.65(s, 1H); MS(NH$_3$-CI) Calc. for (M+1)$^+$: 662. Found:662.

Part B. Methyl $N^3$-[2-{2-(4-guanidinophenyl)-1,3,4-oxadiazol-5-yl}-acetyl]-$N^2$-(n-butoxycarbonyl)-2,3-(S)-diaminopropionate TFA salt A solution of Methyl $N^3$-[2-{2-(4-N,N'-bis-tert-butoxycarbonylguanidinophenyl)-1,3,4-oxadiazol-5-yl}acetyl]-$N^2$-(n-butoxycarbonyl)-2,3-(S)-diaminopropionate(70 mg, 0.10 mmol) in methylene chloride(3 ml) containing TFA(1 ml) was stirred at rt for 2 hrs. After evaporation, the residue was taken up in methanol(4 ml) and purified by HPLC to afford an oily product(46 mg, 95% yield). MS(ESI) Calc. for (M+1)$^+$: 462. Found: 462(free base).

EXAMPLE 353

Methyl N-[2-{2-(4-aminophenyl)-1,3,4-oxadiazol-5-ylthio}-acetyl]glycine

Part A. Methyl N-(2-chloroacetyl)glycine

This material was prepared according to the procedure of Birnbaum et al (J. Bio. Chem. 1952, 194, 455) from glycine hydrogen chloride and chloroacetyl anhydride. $^1$H NMR (300 MHz, CDCl$_3$) δ3.80(s, 3H), 4.08(d, J=8, 2H), 4.12(s, 2H), 7.06(s broad, 1H); MS(NH$_3$-CI) Calc. for (M+1)$^+$: 167. Found: 167.

Part B. Methyl N-[2-{2-(4-tert-butoxycarbonylaminophenyl)-1,3,4-oxadiazol-5-ylthio}acetyl]glycine A mixture of 4-tert-Butoxycarbonylaminobenzoylhydrazine(820 mg. 3.3 mmol) and potassium hydroxide(217 mg, 3.3 mmol) in ethanol (95%, 20 ml) was stirred till all potassium hydroxide was dissolved. Carbon disulfide(280 mg, 3.6 mmol) was then introduced, and the solution gradually became pale yellow and some precipitate appeared. After stirring at reflux for 10 hrs, Methyl N-(2-chloroacetyl)glycine (4601 mg, 3.6 mmol) was added and stirring was continued for 20 hrs at reflux. The solvent was removed and the residue was worked up as usual, followed by chromatography over silica gel, affording 900 mg of the product(67% yield). $^1$H NMR(300 NHz, DMSO-d$_6$) δ1.56(s, 9H), 3.74(s, 3H), 3.96(s, 2H), 4.08(d, J=6, 2H), 6.68(s, 1H), 7.52(d, J=8, 2H), 7.96(d, J=8, 2H); MS(NH$_3$-CI) Calc for (M+1)$^+$: 423. Found:423.

Part C Methyl N-[2-{2-(4-aminophenyl)-1,3,4-oxadiazol-5-ylthio}acetyl]glycine

A solution of Methyl N-[2-{2-(4-tert-butoxycarbonylaminophenyl)-1,3,4-oxadiazol-5-ylthio}acetyl]glycine(200 mg, 0.47 mmol) in methylene chloride(5 ml) containing TFA(1.5 ml) was stirred at rt for 2 hrs. After evaporation, the residue was taken up in CH$_2$Cl$_2$ and washed with saturated NaHCO$_3$ and brine, dried. Removal of the solvent gave a solid which was recrystallized from ethanol to afford 100 mg of the product(66%). $^1$H NMR(300 MHz, CDCl$_3$) δ3.74(s, 3H), 3.94(s, 2H), 4.08(d, J=6, 3H), 6.74(d, J=8, 2H), 7.60(s, broad, 1H), 7.80(J=8, 2H); MS(NH$_3$-CI) Calc. for (M+1)$^+$: 323. Found: 323.

EXAMPLE 385

Methyl N-[2-{2-(4-guanidinophenyl)-1,3,4-oxadiazol-5-ylthio}-acetyl]glycine TFA salt The same procedures as in Example 242 were adopted to prepare this material.

Part A. Methyl N-[2-{2-(4-N,N'-bis-tert-butoxycarbonylguanidinophenyl)-1,3,4-oxadiazol-5-ylthio}acetyl]glycine $^1$H NMR(300 MHz, CDCl$_3$) δ1.54(s, 9H), 1.58(s, 9H), 3.76(s, 3H), 3.98(s, 2H), 4.06(d, J=6, 2H), 7.34(t, J=5, 1H), 7.82(d, J=8, 2H), 7.98(d, J=8, 2H), 10.65(s, 1H), 11.65(s, 1H); MS(NH$_3$-CI) Calc. for (M+1)$^+$: 565. Found: 565.

Part B. Methyl N-[2-{2-(4-guanidinophenyl)-1,3,4-oxadiazol-5-yl}-acetyl]-glycine TFA salt MS(ESI) Calc. for (M+1)$^+$: 365. Found: 365(free base).

EXAMPLE 392

Methyl N-[2-{2-(4-guanidinophenyl)-1,3,4-oxadiazol-5-ylthio}-acetyl]-(S)-phenylalanine TFA salt Part A. Methyl N-2-chloroacetyl-(S)-phenylalanine To a mixture of (s)-phenylalanine methyl ester hydrogen chloride(2.15 g, 10 mmol) and triethylamine(2.22 g, 22 mmol) in methylene chloride cooled at −10 C. with dry ice was added chloroacetic chloride(1.15 g, 10 mmol) at such a rate that the inner temperature of the mixture was kept below −5 C. After addition, the mixture was stirred at 10 C. for additional 30 mins and then at rt for 2 hrs. Work-up as usual followed by chromatography gave 2.4 g of the product (94% yield). $^1$H NMR(300 MHz, CDCl$_3$) δ3.14(dd, J=16 and 4, 1H), 3.18(dd, J=16 and 4, 1H), 3.76(s, 3H), 4.04(s, 2H), 4.88(m, 1H), 6.98(s, broad, 1H), 7.10– 7.30(m, 5H); MS(NH$_3$-CI) Calc. for (M+1)$^+$: 256. Found: 256.

Part B. Methyl N-[2-{2-(4-tert-butoxycarbonylaminophenyl)-1,3,4-oxadiazol-5-ylthio}acetyl]-(S)-phenylalanine A similar procedure to Part B of Example 30 was adopted to prepare this material from 4-tert-butoxycarbonylaminobenzoylhydrazine and methyl N-(2-chloroacetyl)-(s)-phenylalanine. $^1$H NMR (300 NHz, CDCl$_3$) δ1.56(s, 9H), 3.06(dd, J=16 and 4, 1H), 3.20(dd, J=16 and 4, 1H), 3.74(s, 3H), 3.82(d, J=16, 1H), 3.94(d, J=16, 1H), 4.88(m, 1H), 6.78(s, 1H), 7.02–7.18(m, 5H), 7.40(d, J=6, 1H), 7.54(d, J=8, 2H), 7.92(d, J=8, 2H); MS(NH$_3$-CI) Calc for (M+1)$^+$: 513. Found:513.

Part C Methyl N-[2-{2-(4-aminophenyl)-1,3,4-oxadiazol-5-ylthio}acetyl]-(S)-phenylanaline A similar procedure to Part C of Example 30 was adopted to prepare this material. $^1$H NMR(300 MHz, CDCl$_3$) δ3.04 (dd, J=16 and 4, 1H), 3.20(dd, J=16 and 4, 1H), 3.70(s, 3H), 3.80(d, J=16, 1H), 3.94(d, J=16, 1H), 4.86(m, 1H), 6.76(d, J=8, 2H), 7.04–7.20(m, 5H), 7.44(d, J=6, 1H), 7.78(d, J=8, 2H); MS(NH$_3$-CI) Calc. for (M+1)$^+$: 413. Found: 413.

Part D. Methyl N-[2-{2-(4-N,N'-bis-tert-butoxycarbonylguanidinophenyl)-1,3,4-oxadiazol-5-ylthio}acetyl]-(S)-phenylalanine A similar procedure to Part A of Example 25 was adopted to prepare this compound. $^1$H NMR(300 MHz, CDCl$_3$) δ1.54(s, 9H), 1.58(s, 9H), 3.04(dd, J=16 and 4, 1H), 3.20(dd, J=16 and 4, 1H), 3.70(s, 3H), 3.80(d, J=16, 1H), 3.94(d, J=16, 1H), 4.86(m, 1H), 7.04–7.20(m, 5H), 7.40(d, J=6, 1H), 7.84(d, J=8, 2H), 7.96(d, J=8, 2H), 10.65(s, 1H), 11.65(s, 1H); MS(NH$_3$-CI) Calc. for (M+1)$^+$: 655. Found: 655.

Part E. Methyl N-[2-{2-(4-guanidinophenyl)-1,3,4-oxadiazol-5-yl}-acetyl]-(S)-phenylalanine TFA salt A similar procedure to Part B of Example 242 was adopted to prepare this compound.

MS(ESI) Calc. for (M+1)$^+$: 455. Found: 455(free base).

EXAMPLE 399

Ethyl N-[2-{2-(4-amidinophenyl)-1,3,4-oxadiazol-5-ylthio}-acetyl]-(S)-phenylalanine HCl salt Part A. Methyl N-[2-{2-(4-cyanophenyl)-1,3,4-oxadiazol-5-ylthio}-acetyl]-(S)-phenylalanine HCl salt A similar procedure to Part B of Example 353 was adopted to prepare this compound from 4-cyanobenzoylhydrazine and methyl N-(2-chloroacetyl)-(s)-phenylalanine. $^1$H NMR(300 MHz, CDCl$_3$) δ1.2(t, J=8, 3H), 3.04(dd, J=16 and 6, 1H), 3.20(dd, J=16 and 6, 1H), 3.88(d, J=16, 1H), 4.00(d, J=16, 1H), 4.18(q, J=8, 2H), 4.86(m, 1H), 7.04–7.24(m, 5H), 7.82(d, J=8, 2H), 8.14(d, J=8, 2H); MS(NH$_3$-CI) Calc. for (M+1)$^+$: 423. Found: 423.

Part B. Ethyl N-[2-{2-(4-amidinophenyl)-1,3,4-oxadiazol-5-ylthio}-acetyl]-(S)-phenylalanine HCl salt A similar procedure to Part C of Example 258 was adopted to prepare this material. $^1$H NMR(300 MHz, DMSO-d$_6$) δ1.24(t, J=8, 3H), 3.06(dd, J=16 and 6, 1H), 3.22(dd, J=16 and 6, 1H), 3.88(d, J=16, 1H), 4.00(d, J=16, 1H), 4.18(q, J=8, 2H), 4.86(m, 1H), 7.02–7.18(m, 5H), 7.90(d, J=8, 2H), 8.20(d, J=8, 2H); MS(ESI) Calc. for (M+1)$^+$: 454. Found: 454.

EXAMPLE 404

Methyl N2-[2-{2-(4-aminophenyl)-1,3,4-oxadiazol-5-ylthio}-acetyl]-N3-(n-butyloxycarbonyl)-2,3-(S)-diaminopropionate TFA salt Part A. Methyl N$^2$-Cbz-N$^3$-n-butyloxycarbonyl-(S)-2,3-diaminopropionate.

To a mixture of methyl N$^2$-Cbz-(S)-2,3-diaminopropionate HCl salt (1 g, 3.5 mmol) and NaHCO$_3$ (700 mg, 8.4 mmol) in 6 mL water and 6 mL THF cooled in an ice bath was added slowly butyl chloroformate (4.2 mmol, 0.53 mL) over 15 min. After stirring for 1 hour, ethyl acetate was added and the solution was washed with dilute citric acid, brine, NaHCO$_3$ and brine, dried (MgSO$_4$), and concentrated to give 1.2 g (100%) oily product. $^1$H NMR (300 MHz, CDCl$_3$) δ0.90(t, J=8, 3H), 1.38(m, 2H), 1.58(m, 2H), 3.60(m, 2H), 3.78(s, 3H), 4.04(t, J=8, 2H), 4.42(m, 1H), 4.98(s, broad, 1H), 5.14(s, 2H), 5.80(d, J=6, 1H), 7.38(m, 5H); MS(NH$_3$-CI) Calc. for (M+1)$^+$: 353. Found: 353.

Part B. Methyl N$^3$-n-butyloxycarbonyl-(S)-2,3-diaminopropionate HCO$_2$H salt.

A mixture of methyl N$^2$-Cbz-N$^3$-n-butoxycarbonyl-(S)-2,3-diaminopropionate. (3.4 mmol, 1.3 g), formic acid (10.2 mmol, 0.38 mL) and 10% Pd/C (130 mg) in 20 mL methanol was stirred at room temperature for 1 hour and filtered through a celite. The filtrate was concentrated to give 0.75 g (100%) oily product. $^1$H NMR (300 MHz, DMSO-$d_6$) δ0.86(t, J=8, 3H), 1.32(m, 2H), 1.50(m, 2H), 3.19(m, 2H), 3.44(t, J=6, 1H), 3.60(s, 3H), 3.92(t, J=8, 2H), 7.18(t, J=4, 1H), 8.20(s, 2H).

Part C. Methyl N$^2$-[2-{2-(4-tert-butoxycarbonylaminophenyl)-1,3,4-oxadiazol-5-ylthio}-acetyl]-N$^3$-(n-butyloxycarbonyl)-2,3-(S)-diaminopropionate The same coupling reaction conditions as Part J of Example 1 were adopted to prepare the compound from 2-{2-(4-tert-butoxycarbonylaminophenyl)-1,3,4-oxadiazol-5-ylthio}acetic acid and Methyl N$^3$-n-butyloxycarbonyl-(S) -2,3-diaminopropionate HCO2H salt. $^1$H NMR(300 MHz, CDCl$_3$) δ0.92(t, J=8, 3H), 1.38(m, 2H), 1.58(m, 2H), 1.60(s, 9H), 3.64(m, 2H), 3.80(s, 3H), 4.08(t, J=8, 2H), 4.62(m, 1H), 5.20(t, J=6, 1H), 7.50(d, J=8, 2H), 7.70(d, J=6, 1H), 7.96(d, J=8, 2H), 8.24(s, 1H); MS(NH$_3$-CI) Calc. for (M+1)$^+$: 552. Found: 552.

Part D. Methyl N$^2$-[2-{2-(4-aminophenyl)-1,3,4-oxadiazol-5-ylthio}-acetyl]-N$^3$-(n-butyloxycarbonyl)-2,3-(S)-diaminopropionate TFA salt A similar procedure to Part C of Example 353 was adopted to prepare this material. MS(ESI) Calc. for (M+1)$^+$: 452. Found: 452.

EXAMPLE 422

Methyl N$^2$-[2-{2-(4-N,N'-bis-tert-butoxycarbonylguanidinophenyl)-1,3,4-oxadiazol-5-ylthio}-acetyl]-N$^3$-(n-butyloxycarbonyl)-2,3-(S)-diaminopropionate The same procedures as in Example 242 were adopted to prepare this material from Methyl N$^2$-[2-{2-(4-aminophenyl)-1,3,4-oxadiazol-5-ylthio}-acetyl]-N$^3$-(n-butyloxycarbonyl)-2,3-(S)-diaminopropionate.

Part A. Methyl N$^2$-[2-{2-(4-N,N'-bis-tert-butoxycarbonylguanidinophenyl)-1,3,4-oxadiazol-5-ylthio}-acetyl]-N$^3$-(n-butyloxycarbonyl)-2,3-(S)-diaminopropionate $^1$H NMR(300 MHz, CDCl$_3$) δ0.90(t, J=8, 3H), 1.32(m, 2H), 1.54(s, 9H), 1.58(s, 9H), 1.60(m, 2H), 3.64(m, 2H), 3.78(s, 3H), 3.98(t,J=8, 2H), 4.62(s, 1H), 5.20(t, J=6, 1H), 7.70(d, J=6, 1H), 7.82(d, J=8, 2H), 7.98(d, J=8, 2H), 10.62(s, 1H), 11.65(s, 1H); MS(NH$_3$-CI) Calc. for (M+1)$^+$: 694. Found: 694.

Part B. Methyl N$^2$-[2-{2-(4-guanidinophenyl)-1,3,4-oxadiazol-5-ylthio}-acetyl]-N$^3$-(n-butyloxycarbonyl)-2,3-(S)-diaminopropionate MS(ESI) Calc. for (M+1)$^+$: 494. Found: 494.

EXAMPLE 440

Methyl N$^2$-[2-{2-(4-amidinophenyl)-1,3,4-thiodiazol-5-ylthio}-acetyl]-N$^3$-(n-butyloxycarbonyl)-2,3-(S)-diaminopropionate HCl salt Part A. Methyl N$^2$-[2-{2-(4-cyanophenyl)-1,3,4-thiodiazol-5-ylthio}-acetyl]-N$^3$-(n-butyloxycarbonyl)-(S)-diaminopropionate The same coupling reaction conditions as Part J of Example 1 were adopted to prepare this compound from 2-{2-(4-cyanophenyl)-1,3,4-thiodiazol-5-ylthio}acetic acid and Methyl N$^3$-n-butyloxycarbonyl-(S)- 2,3-diaminopropionate HCO2H salt. $^1$H NMR(300 MHz, CDCl$_3$) δ0.92(t, J=8, 3H), 1.32(m, 2H), 1.56(m, 2H), 3.60 (m, 2H), 3.80(s, 3H), 4.04(t, J=8, 2H), 4.58(m, 1H), 5.40(t, J=6, 1H), 7.50(d, J=6, 1H), 7.94(d, J=8, 2H), 8.10(d, J=8, 2H); MS(NH$_3$-CI) Calc. for (M+1)$^+$: 478. Found: 478.

Part B. Methyl N$^2$-[2-{2-(4-amidinophenyl)-1,3,4-thiodiazol-5-ylthio}-acetyl]-N$^3$-(n-butyloxycarbonyl)-2,3-(S)-diaminopropionate HCl salt A similar procedure to Part C of Example 258 was adopted to prepare this material. $^1$H NMR(300 MHz, CDCl$_3$) δ0.88(t, J=8, 3H), 1.30(m, 2H), 1.50(m, 2H), 3.50 (m, 2H), 3.88(s, 3H), 4.10(t, J=8, 2H), 4.50(m, 1H), 7.98(d, J=8, 2H), 8.12(d, J=8, 2H); MS(ESI) Calc. for (M+1)$^+$: 495. Found: 495(free base).

The previous working examples are shown in Table 1 and additional examples of compounds of the invention are shown in Table 1 and table 2 which can be prepared by the schemes and procedure discussed above or variations thereof obvious to those skilled in the art using appropriate starting materials.

TABLE 1

| Ex No. | R$^1$—Ar | m | A | W | R$^5$ | R | Y [(M + 1)$^+$] | MS |
|---|---|---|---|---|---|---|---|---|
| 1 | 4-amidinophenyl | 0 | S | CH$_2$ | H | n-butyloxycarbonyl | OMe | 463 |
| 2 | 4-amidinophenyl | 0 | S | CH$_2$ | H | n-butyloxycarbonyl | OH | 449 |
| 4 | 4-amidinophenyl | 0 | S | (CH$_2$)$_2$ | H | n-butyloxycarbonyl | OH | |
| 5 | 4-amidinophenyl | 0 | S | (CH$_2$)$_3$ | H | n-butyloxycarbonyl | OH | |
| 6 | 4-amidinophenyl | 1 | S | CH$_2$ | H | n-butyloxycarbonyl | OH | |
| 7 | 4-amidinophenyl | 0 | S | CH$_2$ | Me | n-butyloxycarbonyl | OH | |
| 8 | 4-amidinophenyl | 2 | S | CH$_2$ | H | n-butyloxycarbonyl | OH | |
| 9 | 4-amidinophenyl | 0 | S | CH$_2$ | H | H | OH | |
| 10 | 4-amidinophenyl | 0 | S | CH$_2$ | H | benzyloxycarbonyl | OH | |
| 11 | 4-amidinophenyl | 0 | S | CH$_2$ | H | t-butyloxycarbonyl | OH | |
| 12 | 4-amidinophenyl | 0 | S | CH$_2$ | H | ethyloxycarbonyl | OH | |
| 13 | 4-amidinophenyl | 0 | S | CH$_2$ | H | methyloxycarbonyl | OH | |
| 14 | 4-amidinophenyl | 0 | S | CH$_2$ | H | n-pentyloxycarbonyl | OH | |
| 15 | 4-amidinophenyl | 0 | S | CH$_2$ | H | n-hexyloxycarbonyl | OH | |
| 16 | 4-amidinophenyl | 0 | S | CH$_2$ | H | phenylethylcarbonyl | | |
| 17 | 4-amidinophenyl | 0 | S | CH$_2$ | H | 2,2-dimethylpropylcarbonyl | OH | |
| 18 | 4-amidinophenyl | 0 | S | CH$_2$ | H | n-pentylcarbonyl | OH | |
| 19 | 4-amidinophenyl | 0 | S | CH$_2$ | H | n-butylcarbonyl | OH | |

TABLE 1-continued

| Ex No. | R¹—Ar | m | A | W | R⁵ | R | Y | [(M + 1)⁺] MS |
|---|---|---|---|---|---|---|---|---|
| 20 | 4-amidinophenyl | 0 | S | $CH_2$ | H | propionyl | OH | |
| 21 | 4-amidinophenyl | 0 | S | $CH_2$ | H | acetyl | OH | |
| 22 | 4-amidinophenyl | 0 | S | $CH_2$ | H | methylsulfonyl | OH | |
| 23 | 4-amidinophenyl | 0 | S | $CH_2$ | H | ethylsulfonyl | OH | |
| 24 | 4-amidinophenyl | 0 | S | $CH_2$ | H | n-butylsulfonyl | OH | |
| 25 | 4-amidinophenyl | 0 | S | $CH_2$ | H | 3-methylphenylsulfonyl | OMe | 517 |
| 26 | 4-amidinophenyl | 0 | S | $CH_2$ | H | 3-methylphenylsulfonyl | OH | 503 |
| 27 | 4-amidinophenyl | 0 | S | $CH_2$ | Me | 3-methylphenylsulfonyl | OH | |
| 28 | 4-amidinophenyl | 0 | S | $CH_2$ | Et | 3-methylphenylsulfonyl | OH | |
| 29 | 4-amidinophenyl | 0 | S | $(CH_2)_2$ | H | 3-methylphenylsulfonyl | OH | |
| 30 | 4-amidinophenyl | 1 | S | $CH_2$ | H | 3-methylphenylsulfonyl | OH | |
| 31 | 4-amidinophenyl | 2 | S | $CH_2$ | H | 3-methylphenylsulfonyl | OH | |
| 32 | 4-amidinophenyl | 0 | S | $CH_2$ | H | phenylsulfonyl | OH | |
| 33 | 4-amidinophenyl | 0 | S | $CH_2$ | H | 4-methylsulfonyl | OH | |
| 34 | 4-amidinophenyl | 0 | S | $CH_2$ | H | benzylsulfonyl | OH | |
| 35 | 4-amidinophenyl | 0 | S | $CH_2$ | H | 2-pyridylcarbonyl | OH | |
| 36 | 4-amidinophenyl | 0 | S | $CH_2$ | H | 3-pyridylcarbonyl | OH | |
| 37 | 4-amidinophenyl | 0 | S | $CH_2$ | H | 4-pyridylcarbonyl | OH | |
| 38 | 4-amidinophenyl | 0 | S | $CH_2$ | H | 2-pyridylmethylcarbonyl | OH | |
| 39 | 4-amidinophenyl | 0 | S | $CH_2$ | H | 3-pyridylmethylcarbonyl | OH | |
| 40 | 4-amidinophenyl | 0 | S | $CH_2$ | H | 4-pyridylmethylcarbonyl | OH | |
| 41 | 4-amidinophenyl | 0 | S | $CH_2$ | H | 2-pyridylmethoxycarbonyl | OH | |
| 42 | 4-amidinophenyl | 0 | S | $CH_2$ | H | 3-pyridylmethoxycarbonyl | OH | |
| 43 | 4-amidinophenyl | 0 | S | $CH_2$ | H | 4-pyridylmethoxycarbonyl | OH | |
| 44 | 4-(N-methylamidino)phenyl | 0 | S | $CH_2$ | H | 3-methylphenylsulfonyl | OMe | 531 |
| 45 | 4-(N-methylamidino)phenyl | 0 | S | $CH_2$ | H | n-butyloxycarbonyl | OH | |
| 46 | 4-(N-methylamidino)phenyl | 0 | S | $CH_2$ | H | n-hexyloxycarbonyl | OH | |
| 47 | 4-(N-methylamidino)phenyl | 0 | S | $CH_2$ | H | styrylsulfonyl | OH | |
| 48 | 4-(N-methylamidino)phenyl | 1 | S | $CH_2$ | H | n-butyloxycarbonyl | OH | |
| 49 | 4-(N-methylamidino)phenyl | 2 | S | $CH_2$ | H | n-butyloxycarbonyl | OH | |
| 50 | 4-(N-methylamidino)phenyl | 1 | S | $CH_2$ | H | 3-methylphenylsufonyl | OH | |
| 51 | 4-(N-methylamidino)phenyl | 0 | S | $(CH_2)_2$ | H | 2-methylphenylsufonyl | OH | |
| 52 | 4-(N-methylamidino)phenyl | 0 | S | $CH_2$ | Et | 3-methylphenylsulfonyl | OH | |
| 53 | 4-(N-methylamidino)phenyl | 0 | S | $CH_2$ | Me | n-butyloxycarbonyl | OH | |
| 54 | 4-(N-methylamidino)phenyl | 0 | S | $CH_2$ | H | 4-methylphenylsulfonyl | OH | |
| 55 | 4-(N-methylamidino)phenyl | 0 | S | $CH_2$ | H | phenylsufonyl | OH | |
| 56 | 4-(N-methylamidino)phenyl | 0 | S | $CH_2$ | H | benzylsufonyl | OH | |
| 57 | 4-(N-methylamidino)phenyl | 0 | S | $CH_2$ | H | 2-pyridylcarbonyl | OH | |
| 58 | 4-(N-methylamidino)phenyl | 0 | S | $CH_2$ | H | 3-pyridylcarbonyl | OH | |
| 59 | 4-(N-methylamidino)phenyl | 0 | S | $CH_2$ | H | 4-pyridylcarbonyl | OH | |
| 60 | 4-(N-methylamidino)phenyl | 0 | S | $CH_2$ | H | 2-pyridylmethylcarbonyl | OH | |
| 61 | 4-(N-methylamidino)phenyl | 0 | S | $CH_2$ | H | 3-pyridylmethylcarbonyl | OH | |
| 62 | 4-(N-methylamidino)phenyl | 0 | S | $CH_2$ | H | 4-pyridylmethylcarbonyl | OH | |
| 63 | 4-(N-methylamidino)-phenyl | 0 | S | $CH_2$ | H | 3-methylphenylsulfonyl | OH | 517 |
| 64 | 4-(N-n-butylamidino)-phenyl | 0 | S | $CH_2$ | H | 3-methylphenylsulfonyl | OMe | 573 |
| 65 | 4-(N-n-butylamidino)-phenyl | 0 | S | $CH_2$ | H | 3-methylphenylsulfonyl | OH | 559 |
| 67 | 4-(N-n-butylamidino)- | 1 | S | $CH_2$ | H | 3-methylphenylsulfonyl | OH | |

TABLE 1-continued

| Ex No. | R¹—Ar | m | A | W | R⁵ | R | Y | [(M + 1)⁺] MS |
|---|---|---|---|---|---|---|---|---|
| | phenyl | | | | | | | |
| 68 | 4-(N-n-butylamidino)-phenyl | 2 | S | CH₂ | H | 3-methylphenylsulfonyl | OH | |
| 69 | 4-(N-n-butylamidino)-phenyl | 0 | S | (CH₂)₂ | H | 3-methylphenylsulfonyl | OH | |
| 70 | 4-(N-n-butylamidino)-phenyl | | S | CH₂ | Me | 3-methylphenylsulfonyl | OH | |
| 71 | 4-(N-n-butylamidino)-phenyl | 1 | S | CH₂ | Et | 3-methylphenylsulfonyl | OH | |
| 72 | 4-(N-ethylamidino)-phenyl | 1 | S | CH₂ | H | 3-methylphenylsulfonyl | OH | |
| 73 | 4-(N-ethylamidino)-phenyl | 0 | S | CH₂ | H | 3-methylphenylsulfonyl | OH | |
| 74 | 4-(N-ethylamidino)-phenyl | 2 | S | CH₂ | H | 3-methylphenylsulfonyl | OH | |
| 75 | 4-(N-ethylamidino)-phenyl | 0 | S | CH₂ | Me | 3-methylphenylsulfonyl | OH | |
| 76 | 4-(N-ethylamidino)-phenyl | 0 | S | CH₂ | Et | 3-methylphenylsulfonyl | OH | |
| 77 | 4-(N-ethylamidino)-phenyl | 0 | S | (CH₂)₂ | H | 3-methylphenylsulfonyl | OH | |
| 78 | 4-(N-ethylamidino)-phenyl | 0 | S | CH₂ | H | 2-methylphenylsulfonyl | OH | |
| 79 | 4-(N-ethylamidino)-phenyl | 0 | S | CH₂ | H | 4-methylphenylsulfonyl | OH | |
| 80 | 4-(N-ethylamidino)-phenyl | 0 | S | CH₂ | H | phenylsulfonyl | OH | |
| 81 | 4-(N-ethylamidino)-phenyl | 0 | S | CH₂ | H | 2-pyridylsulfonyl | OH | |
| 82 | 4-(N-ethylamidino)-phenyl | 0 | S | CH₂ | H | 3-pyridylsulfonyl | OH | |
| 83 | 4-(N-ethylamidino)-phenyl | 0 | S | CH₂ | H | 4-pyridylsulfonyl | OH | |
| 84 | 4-(N-ethylamidino)-phenyl | 0 | S | CH₂ | H | 2-pyridylcarbonyl | OH | |
| 85 | 4-(N-ethylamidino)-phenyl | 0 | S | CH₂ | H | 3-pyridylcarbonyl | OH | |
| 87 | 4-(N-ethylamidino)-phenyl | 0 | S | CH₂ | H | 4-pyridylcarbonyl | OH | |
| 88 | 4-amidinophenyl | 0 | S | CH₂ | H | 2-methylphenylsulfonyl | OMe | 517 |
| 89 | 4-amidinophenyl | 0 | S | CH₂ | H | 2-methylphenylsulfonyl | OH | 503 |
| 90 | 4-amidinophenyl | 1 | S | CH₂ | H | 2-methylphenylsulfonyl | OH | |
| 91 | 4-amidinophenyl | 2 | S | CH₂ | H | 2-methylphenylsulfonyl | OH | |
| 92 | 4-amidinophenyl | 0 | S | (CH₂)₂ | H | 2-methylphenylsulfonyl | OH | |
| 93 | 4-amidinophenyl | 0 | S | (CH₂)₃ | H | 2-methylphenylsulfonyl | OH | |
| 94 | 4-amidinophenyl | 0 | S | CH₂ | Me | 2-methylphenylsulfonyl | OH | |
| 95 | 4-amidinophenyl | 0 | S | CH₂ | Et | 2-methylphenylsulfonyl | OH | |
| 96 | 4-amidinophenyl | 0 | S | CH₂ | H | 3,5-dimethylisoxazol-4-yl-sulfonyl | OMe | 522 |
| 97 | 4-amidinophenyl | 0 | S | CH₂ | H | 3,5-dimethylisoxazol-4-yl-sulfonyl | OH | 508 |
| 98 | 4-amidinophenyl | 1 | S | CH₂ | H | 3,5-dimethylisoxazol-4-yl-sulfonyl | OH | |
| 99 | 4-amidinophenyl | 2 | S | CH₂ | H | 3,5-dimethylisoxazol-4-yl-sulfonyl | OH | |
| 100 | 4-amidinophenyl | 0 | S | (CH₂)₂ | H | 3,5-dimethylisoxazol-4-yl-sulfonyl | OH | |
| 101 | 4-amidinophenyl | 0 | S | (CH₂)₃ | H | 3,5-dimethylisoxazol-4-yl-sulfonyl | OH | |
| 102 | 4-amidinophenyl | 0 | S | CH₂ | Me | 3,5-dimethylisoxazol-4-yl-sulfonyl | OH | |
| 103 | 4-amidinophenyl | 0 | S | CH₂ | Et | 3,5-dimethylisoxazol-4-yl-sulfonyl | OH | |
| 104 | 4-piperidinyl | 0 | S | CH₂ | H | 3-methylphenylsulfonyl | OMe | 482 |
| 105 | 4-piperidinyl | 0 | S | CH₂ | H | 3-methylphenylsulfonyl | OH | |
| 106 | 4-piperidinyl | 1 | S | CH₂ | H | 3-methylphenylsulfonyl | OH | |
| 107 | 4-piperidinyl | 2 | S | CH₂ | H | 3-methylphenylsulfonyl | OH | |
| 108 | 4-piperidinyl | 2 | S | CH₂ | H | 2-methylphenylsulfonyl | OH | |
| 109 | 4-piperidinyl | 2 | S | CH₂ | H | 4-methylphenylsulfonyl | OH | |

TABLE 1-continued $$R^1\text{-}Ar\text{-}(CH_2)_m\text{-}\underset{N-N}{\overset{A}{\diagup\!\!\diagdown}}\text{-}W\text{-}\underset{O}{\overset{R^5}{N}}\text{-}\underset{O}{\overset{NHR}{\diagup}}\text{-}Y$$

| Ex No. | R¹—Ar | m | A | W | R⁵ | R | Y | [(M + 1)⁺] MS |
|---|---|---|---|---|---|---|---|---|
| 110 | 4-piperidinyl | 2 | S | CH₂ | Me | 3-methylphenylsulfonyl | OH | |
| 111 | 4-piperidinyl | 2 | S | CH₂ | Et | 3-methylphenylsulfonyl | OH | |
| 112 | 4-piperidinyl | 1 | S | (CH₂)₂ | H | 3-methylphenylsulfonyl | OH | |
| 113 | 4-piperidinyl | 2 | S | (CH₂)₂ | H | 3-methylphenylsulfonyl | OH | |
| 114 | 4-piperidinyl | 2 | S | CH₂ | H | phenylsulfonyl | OH | |
| 115 | 4-piperidinyl | 2 | S | CH₂ | H | 3,5-dimethylisoxazol-4-ylsulfonyl | OH | |
| 116 | 4-piperidinyl | 2 | S | CH₂ | H | benzylsulfonyl | OH | |
| 117 | 4-piperidinyl | 2 | S | CH₂ | H | 2-pyridylsulfonyl | OH | |
| 118 | 4-piperidinyl | 2 | S | CH₂ | H | 3-pyridylsulfonyl | OH | |
| 119 | 4-piperidinyl | 2 | S | CH₂ | H | 4-pyridylsulfonyl | OH | |
| 120 | 4-piperidinyl | 2 | S | CH₂ | H | 2-pyridylmethylsulfonyl | OH | |
| 121 | 4-piperidinyl | 2 | S | CH₂ | H | 3-pyridylmethylsulfonyl | OH | |
| 122 | 4-piperidinyl | 2 | S | CH₂ | H | 4-pyridylmethylsulfonyl | OH | |
| 123 | 4-piperidinyl | 2 | S | CH₂ | H | 2-pyridylcarbonyl | OH | |
| 124 | 4-piperidinyl | 2 | S | CH₂ | H | 3-pyridylcarbonyl | OH | |
| 125 | 4-piperidinyl | 2 | S | CH₂ | H | 4-pyridylcarbonyl | OH | |
| 126 | 4-piperidinyl | 2 | S | CH₂ | H | 2-pyridylsulfonyl | OH | |
| 127 | 4-piperidinyl | 2 | S | CH₂ | H | benzyloxycarbonyl | OH | |
| 128 | 4-piperidinyl | 2 | S | CH₂ | H | n-butyloxycarbonyl | OH | |
| 129 | 4-piperidinyl | 2 | S | CH₂ | H | ethyloxycarbonyl | OH | |
| 130 | 4-piperidinyl | 2 | S | CH₂ | H | n-hexyloxycarbonyl | OH | |
| 131 | 4-piperidinyl | 2 | S | CH₂ | H | methyloxycarbonyl | OH | |
| 132 | 4-piperidinyl | 2 | S | CH₂ | H | n-propyloxycarbonyl | OH | |
| 133 | 4-piperidinyl | 0 | S | (CH₂)₃ | H | 3-methylphenylsulfonyl | OMe | 510 |
| 134 | 4-piperidinyl | 0 | S | (CH₂)₃ | H | 3-methylphenylsulfonyl | OH | 496 |
| 135 | 4-piperidinyl | 1 | S | (CH₂)₃ | H | 3-methylphenylsulfonyl | OH | |
| 136 | 4-piperidinyl | 2 | S | (CH₂)₃ | H | 3-methylphenylsulfonyl | OH | |
| 137 | 4-piperidinyl | 0 | S | (CH₂)₃ | Et | 3-methylphenylsulfonyl | OH | |
| 138 | 4-piperidinyl | 0 | S | (CH₂)₃ | Me | 3-methylphenylsulfonyl | OH | |
| 139 | 4-piperidinyl | 0 | S | (CH₂)₃ | H | 2-methylphenylsulfonyl | OH | |
| 140 | 4-piperidinyl | 0 | S | (CH₂)₃ | H | 4-methylphenylsulfonyl | OH | |
| 141 | 4-piperidinyl | 0 | S | (CH₂)₃ | H | phenylsulfonyl | OH | |
| 142 | 4-piperidinyl | 0 | S | (CH₂)₃ | H | benzyloxycarbonyl | OH | |
| 143 | 4-piperidinyl | 0 | S | (CH₂)₃ | H | n-butyloxycarbonyl | OH | |
| 144 | 4-[N,N'-di(trifluoro-ethyl)amindino]phenyl | 0 | S | CH₂ | H | 3-methylphenylsulfonyl | OMe | 681 |
| 145 | 4-guanidinophenyl | 0 | S | CH₂ | H | 3-methylphenylsulfonyl | OMe | 532 |
| 146 | 4-guanidinophenyl | 0 | S | CH₂ | H | 3-methylphenylsulfonyl | OH | 518 |
| 147 | 4-guanidinophenyl | 1 | S | CH₂ | H | 3-methylphenylsulfonyl | OH | |
| 148 | 4-guanidinophenyl | 0 | S | (CH₂)₂ | H | 3-methylphenylsulfonyl | OH | |
| 149 | 4-guanidinophenyl | 0 | S | CH₂ | Me | 3-methylphenylsulfonyl | OH | |
| 150 | 4-guanidinophenyl | 0 | S | CH₂ | Et | 3-methylphenylsulfonyl | OH | |
| 151 | 4-guanidinophenyl | 0 | S | CH₂ | H | 2-methylphenylsulfonyl | OH | |
| 152 | 4-guanidinophenyl | 0 | S | CH₂ | H | 4-methylphenylsulfonyl | OH | |
| 153 | 4-guanidinophenyl | 0 | S | CH₂ | H | benzyloxycarbonyl | OH | |
| 154 | 4-guanidinophenyl | 0 | S | CH₂ | H | 3,5-dimethylisoxazol-4-ylsulfonyl | OH | |
| 155 | 4-guanidinophenyl | 0 | S | CH₂ | H | n-butyloxycarbonyl | OH | |
| 156 | 4-guanidinophenyl | 0 | S | CH₂ | H | phenylsulfonyl | OH | |
| 157 | 4-(N-hydroxylami-dino)phenyl | 0 | S | CH₂ | H | 3-methylphenylsulfonyl | OMe | 533 |
| 158 | 4-(N-hydroxylami-dino)phenyl | 0 | S | CH₂ | H | 3-methylphenylsulfonyl | OH | |
| 159 | 4-(N-hydroxylami-dino)phenyl | 0 | S | CH₂ | Me | 3-methylphenylsulfonyl | OH | |
| 160 | 4-(N-hydroxylami-dino)phenyl | 0 | S | CH₂ | Et | 3-methylphenylsulfonyl | OH | |
| 161 | 4-(N-hydroxylami-dino)phenyl | 0 | S | CH₂ | H | 2-methylphenylsulfonyl | OH | |
| 162 | 4-(N-hydroxylami-dino)phenyl | 0 | S | CH₂ | H | 4-methylphenylsulfonyl | OH | |
| 163 | 4-(N-hydroxylami-dino)phenyl | 0 | S | CH₂ | H | phenylsulfonyl | OH | |
| 164 | 4-(N-hydroxylami-dino)phenyl | 0 | S | CH₂ | H | benzylsulfonyl | OH | |
| 165 | 4-(N-hydroxylami-dino)phenyl | 1 | S | CH₂ | H | 3-methylphenylsulfonyl | OH | |
| 166 | 4-(N-hydroxylami- | 0 | S | (CH₂)₂ | H | 3-methylphenylsulfonyl | OH | |

TABLE 1-continued

| Ex No. | R¹—Ar | m | A | W | R⁵ | R | Y | [(M + 1)⁺] MS |
|---|---|---|---|---|---|---|---|---|
| 167 | 4-(N-hydroxylami-dino)phenyl | 0 | S | CH₂ | H | 3,5-dimthylisoxazol-4-ylsulfonyl | OH | |
| 168 | 4-(N-hydroxylami-dino)phenyl | 0 | S | CH₂ | H | benzyloxycarbonyl | OH | |
| 169 | 4-(N-hydroxylami-dino)phenyl | 0 | S | CH₂ | H | n-butyloxycarbonyl | OH | |
| 170 | 4-amidophenyl | 0 | S | CH₂ | H | 3-methylphenylsulfonyl | OMe | 518 |
| 171 | 4-amidophenyl | 0 | S | CH₂ | H | 3-methylphenylsulfonyl | OH | 504 |
| 172 | 4-amidophenyl | 1 | S | CH₂ | H | 3-methylphenylsulfonyl | OH | |
| 173 | 4-amidophenyl | 2 | S | CH₂ | H | 3-methylphenylsulfonyl | OH | |
| 174 | 4-amidophenyl | 0 | S | (CH₂)₂ | H | 3-methylphenylsulfonyl | OH | |
| 175 | 4-amidophenyl | 0 | S | CH₂ | Me | 3-methylphenylsulfonyl | OH | |
| 176 | 4-amidophenyl | 0 | S | CH₂ | Et | 3-methylphenylsulfonyl | OH | |
| 177 | 4-amidophenyl | 0 | S | CH₂ | H | 2-methylphenylsulfonyl | OH | |
| 178 | 4-amidophenyl | 0 | S | CH₂ | H | 4-methylphenylsulfonyl | OH | |
| 179 | 4-amidophenyl | 0 | S | CH₂ | H | phenylsulfonyl | OH | |
| 180 | 4-amidophenyl | 0 | S | CH₂ | H | 3,5-dimethylisoxazol-4-ylsulfonyl | OH | |
| 181 | 4-amidophenyl | 0 | S | CH₂ | H | benzyloxycarbonyl | OH | |
| 182 | 4-amidophenyl | 0 | S | CH₂ | H | n-butyloxycarbonyl | OH | |
| 183 | 4-amidophenyl | 0 | S | CH₂ | H | 2-pyridylcarbonyl | OH | |
| 184 | 4-(N-methylamido)-phenyl | 0 | S | CH₂ | H | 2-methylphenylsulfonyl | OH | |
| 185 | 4-(N-methylamido)-phenyl | 0 | S | CH₂ | H | 3-methylphenylsulfonyl | OH | |
| 186 | 4-(N-methylamido)-phenyl | 0 | S | CH₂ | H | phenylsulfonyl | OH | |
| 187 | 4-(N-methylamido)-phenyl | 0 | S | CH₂ | H | benzyloxycarbonyl | OH | |
| 188 | 4-(N-methylamido)-phenyl | 0 | S | CH₂ | H | n-butyloxycarbonyl | OH | |
| 189 | 4-(N-methylamido)-phenyl | 0 | S | CH₂ | H | 2-pyridylcarbonyl | OH | |
| 190 | 4-(N,N-dimethyl-amido)phenyl | 0 | S | CH₂ | H | 2-methylphenylsulfonyl | OH | |
| 191 | 4-(N-methyl-N-ethyl)-amidophenyl | 0 | S | CH₂ | H | 2-methylphenylsulfonyl | OH | |
| 192 | 4-amidinophenyl | 0 | S | SCH₂ | H | n-butyloxycarbonyl | OMe | 495 |
| 193 | 4-amidinophenyl | 0 | S | SCH₂ | H | n-butyloxycarbonyl | OH | 481 |
| 194 | 4-amidinophenyl | 0 | S | S(CH₂)₂ | H | n-butyloxycarbonyl | OH | |
| 195 | 4-amidinophenyl | 0 | S | SCH₂ | Me | n-butyloxycarbonyl | OH | |
| 196 | 4-amidinophenyl | 0 | S | SCH₂ | Et | n-butyloxycarbonyl | OH | |
| 197 | 4-amidinophenyl | 0 | S | SCH₂ | H | benzylcarbonyl | OH | |
| 198 | 4-amidinophenyl | 0 | S | SCH₂ | H | methyloxycarbonyl | OH | |
| 199 | 4-amidinophenyl | 0 | S | SCH₂ | H | ethyloxycarbonyl | OH | |
| 200 | 4-amidinophenyl | 0 | S | SCH₂ | H | phenylsulfonyl | OH | |
| 201 | 4-amidinophenyl | 0 | S | SCH₂ | H | 2-methylphenylsulfonyl | OH | |
| 202 | 4-amidinophenyl | 0 | S | SCH₂ | H | 3-methylphenylsulfonyl | OH | |
| 203 | 4-amidinophenyl | 0 | S | SCH₂ | H | 4-methylphenylsulfonyl | OH | |
| 204 | 4-amidinophenyl | 0 | S | SCH₂ | H | benzylsulfonyl | OH | |
| 205 | 4-pyperidinyl | 0 | S | SCH₂ | H | 2-methylphenylsulfonyl | OH | |
| 206 | 4-pyperidinyl | 1 | S | SCH₂ | H | 2-methylphenylsulfonyl | OH | |
| 207 | 4-pyperidinyl | 2 | S | SCH₂ | H | 2-methylphenylsulfonyl | OH | |
| 208 | 4-pyperidinyl | 2 | S | SCH₂ | H | 3-methylphenylsulfonyl | OH | |
| 209 | 4-pyperidinyl | 2 | S | SCH₂ | H | 4-methylphenylsulfonyl | OH | |
| 210 | 4-pyperidinyl | 0 | S | SCH₂ | H | 3-methylphenylsulfonyl | OH | |
| 211 | 4-pyperidinyl | 0 | S | SCH₂ | H | 4-methylphenylsulfonyl | OH | |
| 212 | 4-pyperidinyl | 0 | S | SCH₂ | H | benzylsulfonyl | OH | |
| 213 | 4-pyperidinyl | 0 | S | SCH₂ | H | n-butylsulfonyl | OH | |
| 214 | 4-pyperidinyl | 0 | S | SCH₂ | H | phenylsulfonyl | OH | |
| 215 | 4-pyperidinyl | 0 | S | SCH₂ | H | benzyloxycarbonyl | OH | |
| 216 | 4-pyperidinyl | 0 | S | SCH₂ | H | n-butylcarbonyl | OH | |
| 217 | 4-pyperidinyl | 0 | S | SCH₂ | H | methlcarbonyl | OH | |
| 218 | 4-pyperidinyl | 0 | S | SCH₂ | H | ethylcarbonyl | OH | |
| 219 | 4-pyperidinyl | 0 | S | SCH₂ | Me | n-butylcarbonyl | OH | |
| 220 | 4-pyperidinyl | 0 | S | SCH₂ | Et | n-butylcarbonyl | OH | |
| 221 | 4-pyperidinyl | 0 | S | S(CH₂)₂ | H | n-butylcarbonyl | OH | |
| 222 | 4-aminophenyl | 0 | O | SCH₂ | H | n-butyloxycarbonyl | OMe | 452 |

TABLE 1-continued

| Ex No. | R¹—Ar | m | A | W | R⁵ | R | Y | [(M + 1)⁺] MS |
|---|---|---|---|---|---|---|---|---|
| 223 | 4-aminophenyl | 0 | O | SCH₂ | H | n-butyloxycarbonyl | OH | |
| 224 | 4-aminophenyl | 0 | S | SCH₂ | Me | n-butyloxycarbonyl | OH | |
| 225 | 4-aminophenyl | 0 | O | SCH₂ | Et | n-butyloxycarbonyl | OH | |
| 226 | 4-aminophenyl | 1 | O | SCH₂ | H | n-butyloxycarbonyl | OH | |
| 227 | 4-aminophenyl | 2 | O | SCH₂ | H | n-butyloxycarbonyl | OH | |
| 228 | 4-aminophenyl | 0 | O | S(CH₂)₂ | H | n-butyloxycarbonyl | OH | |
| 229 | 4-aminophenyl | 0 | O | SCH₂ | H | benzylloxycarbonyl | OH | |
| 230 | 4-aminophenyl | 0 | O | SCH₂ | H | methyloxycarbonyl | OH | |
| 231 | 4-aminophenyl | 0 | O | SCH₂ | H | phenylsulfonyl | OH | |
| 232 | 4-aminophenyl | 0 | O | SCH₂ | H | 3-methylsulfonyl | OH | |
| 233 | 4-aminophenyl | 0 | O | SCH₂ | H | 2-methylsulfonyl | OH | |
| 234 | 4-aminophenyl | 0 | O | SCH₂ | H | 4-methylsulfonyl | OH | |
| 235 | 4-aminophenyl | 0 | O | SCH₂ | H | benzylsulfonyl | OH | |
| 236 | 4-aminophenyl | 0 | O | SCH₂ | H | n-butylsulfonyl | OH | |
| 237 | 4-aminophenyl | 0 | O | SCH₂ | H | 3,5-dimethylisoxazol-4-ylsulfonyl | OH | |
| 238 | 4-aminophenyl | 0 | O | SCH₂ | H | 2-pyridylcarbonyl | OH | |
| 239 | 4-aminophenyl | 0 | O | SCH₂ | H | 3-pyridylsulfonyl | OH | |
| 240 | 4-(dimethyl)amino-phenyl | 0 | O | SCH₂ | H | 3-methylsulfonyl | OH | |
| 241 | 4-methylamino-phenyl | 0 | O | SCH₂ | H | 3-methylsulfonyl | OH | |
| 242 | 4-guanidinophenyl | 0 | O | SCH₂ | H | n-butyloxycarbonyl | OMe | 494 |
| 243 | 4-guanidinophenyl | 0 | O | SCH₂ | H | n-butyloxycarbonyl | OH | |
| 244 | 4-guanidinophenyl | 1 | O | SCH₂ | H | n-butyloxycarbonyl | OH | |
| 245 | 4-guanidinophenyl | 2 | O | SCH₂ | H | n-butyloxycarbonyl | OH | |
| 246 | 4-guanidinophenyl | 0 | O | SCH₂ | H | n-butyloxycarbonyl | OH | |
| 247 | 4-guanidinophenyl | 0 | O | S(CH₂)₂ | H | n-butyloxycarbonyl | OH | |
| 248 | 4-guanidinophenyl | 0 | O | SCH₂ | Me | n-butyloxycarbonyl | OH | |
| 249 | 4-guanidinophenyl | 0 | O | SCH₂ | Et | n-butyloxycarbonyl | OH | |
| 250 | 4-guanidinophenyl | 0 | O | SCH₂ | H | benzylloxycarbonyl | OH | |
| 251 | 4-guanidinophenyl | 0 | O | SCH₂ | H | ethyloxycarbonyl | OH | |
| 252 | 4-guanidinophenyl | 0 | O | SCH₂ | H | n-butylsulfonyl | OH | |
| 253 | 4-guanidinophenyl | 0 | O | SCH₂ | H | phenylsulfonyl | OH | |
| 254 | 4-guanidinophenyl | 0 | O | SCH₂ | H | 2-methylphenylsulfonyl | OH | |
| 255 | 4-guanidinophenyl | 0 | O | SCH₂ | H | 3-methylphenylsulfonyl | OH | |
| 256 | 4-guanidinophenyl | 0 | O | SCH₂ | H | 4-methylphenylsulfonyl | OH | |
| 257 | 4-guanidinophenyl | 0 | O | SCH₂ | H | benzylsulfonyl | OH | |
| 258 | 4-amidinophenyl | 0 | O | SCH₂ | H | n-butyloxycarbonyl | OMe | 479 |
| 259 | 4-amidinophenyl | 0 | O | SCH₂ | H | n-butyloxycarbonyl | OH | |
| 260 | 4-amidinophenyl | 1 | O | SCH₂ | H | n-butyloxycarbonyl | OH | |
| 261 | 4-amidinophenyl | 2 | O | SCH₂ | H | n-butyloxycarbonyl | OH | |
| 262 | 4-amidinophenyl | 0 | O | S(CH₂)₂ | H | n-butyloxycarbonyl | OH | |
| 263 | 4-amidinophenyl | 0 | O | SCH₂ | Me | n-butyloxycarbonyl | OH | |
| 264 | 4-amidinophenyl | 0 | O | SCH₂ | Et | n-butyloxycarbonyl | OH | |
| 265 | 4-amidinophenyl | 0 | O | SCH₂ | H | benzyloxycarbonyl | OH | |
| 267 | 4-amidinophenyl | 0 | O | SCH₂ | H | methyloxycarbonyl | OH | |
| 268 | 4-amidinophenyl | 0 | O | SCH₂ | H | ethyloxycarbonyl | OH | |
| 269 | 4-amidinophenyl | 0 | O | SCH₂ | H | n-butylsulfonyl | OH | |
| 270 | 4-amidinophenyl | 0 | O | SCH₂ | H | benzylsulfonyl | OH | |
| 271 | 4-amidinophenyl | 0 | O | SCH₂ | H | 2-methylphenylsulfonyl | OH | |
| 272 | 4-amidinophenyl | 0 | O | SCH₂ | H | phenylsulfonyl | OH | |
| 273 | 4-amidinophenyl | 0 | O | SCH₂ | H | 3-methylphenylsulfonyl | OH | |
| 274 | 4-amidinophenyl | 0 | O | SCH₂ | H | 4-methylphenylsulfonyl | OH | |
| 275 | 4-amidinophenyl | 0 | O | SCH₂ | H | 3,5-dimethylisoxazol-4-ylsulfonyl | OH | |
| 276 | 4-pyperidinyl | 0 | O | SCH₂ | H | 2-methylphenylsulfonyl | OH | |
| 277 | 4-pyperidinyl | 1 | O | SCH₂ | H | 2-methylphenylsulfonyl | OH | |
| 278 | 4-pyperidinyl | 2 | O | SCH₂ | H | 2-methylphenylsulfonyl | OH | |
| 279 | 4-pyperidinyl | 0 | O | S(CH₂)₂ | H | 2-methylphenylsulfonyl | OH | |
| 280 | 4-pyperidinyl | 1 | O | SCH₂ | Me | 2-methylphenylsulfonyl | OH | |
| 281 | 4-pyperidinyl | 1 | O | SCH₂ | Et | 2-methylphenylsulfonyl | OH | |
| 281 | 4-pyperidinyl | 1 | O | SCH₂ | H | 3-methylphenylsulfonyl | OH | |
| 282 | 4-pyperidinyl | 1 | O | SCH₂ | H | 4-methylphenylsulfonyl | OH | |
| 283 | 4-pyperidinyl | 1 | O | SCH₂ | H | phenylsulfonyl | OH | |
| 284 | 4-pyperidinyl | 1 | O | SCH₂ | H | n-butylsulfonyl | OH | |
| 285 | 4-pyperidinyl | 1 | O | SCH₂ | H | 3,5-dimethylisoxazol-4-ylsulfonyl | OH | |
| 286 | 4-pyperidinyl | 1 | O | SCH₂ | H | benzyloxycarbonyl | OH | |

TABLE 1-continued

| Ex No. | R¹—Ar | m | A | W | R⁵ | R | Y | [(M + 1)⁺] MS |
|---|---|---|---|---|---|---|---|---|
| 287 | 4-pyperidinyl | 1 | O | SCH$_2$ | H | n-butyloxycarbonyl | OH | |
| 288 | 4-pyperidinyl | 1 | O | SCH$_2$ | H | methyloxycarbonyl | OH | |
| 289 | 4-pyperidinyl | 1 | O | SCH$_2$ | H | ethylyloxycarbonyl | OH | |
| 290 | 4-aminophenyl | 0 | O | CH$_2$ | H | n-butyloxycarbonyl | OMe | 420 |
| 291 | 4-aminophenyl | 0 | O | CH$_2$ | H | n-butyloxycarbonyl | OH | |
| 292 | 4-aminophenyl | 1 | O | CH$_2$ | H | n-butyloxycarbonyl | OH | |
| 293 | 4-aminophenyl | 2 | O | CH$_2$ | H | n-butyloxycarbonyl | OH | |
| 294 | 4-aminophenyl | 0 | O | (CH$_2$)$_2$ | H | n-butyloxycarbonyl | OH | |
| 295 | 4-aminophenyl | 0 | O | CH$_2$ | H | benzyloxycarbonyl | OH | |
| 296 | 4-aminophenyl | 0 | O | CH$_2$ | H | methyloxycarbonyl | OH | |
| 297 | 4-aminophenyl | 0 | O | CH$_2$ | H | ethyloxycarbonyl | OH | |
| 298 | 4-aminophenyl | 0 | O | CH$_2$ | H | phenylsulfonyl | OH | |
| 299 | 4-aminophenyl | 0 | O | CH$_2$ | H | 2-methylphenylsulfonyl | OH | |
| 300 | 4-aminophenyl | 0 | O | CH$_2$ | H | 3-methylphenylsulfonyl | OH | |
| 301 | 4-aminophenyl | 0 | O | CH$_2$ | H | 4-methylphenylsulfonyl | OH | |
| 302 | 4-aminophenyl | 0 | O | CH$_2$ | H | 3,5-dimethylisoxazol-4-ylsulfonyl | OH | |
| 303 | 4-aminophenyl | 0 | O | CH$_2$ | H | benzylsulfonyl | OH | |
| 304 | 4-pyperidinyl | 0 | O | CH$_2$ | H | 2-methylphenylsulfonyl | OH | |
| 305 | 4-pyperidinyl | 1 | O | CH$_2$ | H | 2-methylphenylsulfonyl | OH | |
| 306 | 4-pyperidinyl | 2 | O | CH$_2$ | H | 2-methylphenylsulfonyl | OH | |
| 307 | 4-pyperidinyl | 0 | O | (CH$_2$)$_2$ | H | 2-methylphenylsulfonyl | OH | |
| 308 | 4-pyperidinyl | 0 | O | (CH$_2$)$_2$ | H | 3-methylphenylsulfonyl | OH | |
| 309 | 4-pyperidinyl | 0 | O | (CH$_2$)$_2$ | H | 4-methylphenylsulfonyl | OH | |
| 310 | 4-pyperidinyl | 0 | O | (CH$_2$)$_2$ | H | phenylsulfonyl | OH | |
| 312 | 4-pyperidinyl | 0 | O | (CH$_2$)$_2$ | H | benzyloxysulfonyl | OH | |
| 313 | 4-pyperidinyl | 0 | O | (CH$_2$)$_2$ | H | n-butylsulfonyl | OH | |
| 314 | 4-pyperidinyl | 2 | O | CH$_2$ | H | 3-methylphenylsulfonyl | OH | |
| 315 | 4-pyperidinyl | 2 | O | CH$_2$ | H | 4-methylphenylsulfonyl | OH | |
| 316 | 4-pyperidinyl | 2 | O | CH$_2$ | H | benzyloxycarbonyl | OH | |
| 317 | 4-pyperidinyl | 2 | O | CH$_2$ | H | n-butyloxycarbonyl | OH | |
| 318 | 4-amidinophenyl | 0 | O | CH$_2$ | H | n-butyloxycarbonyl | OMe | 447 |
| 319 | 4-amidinophenyl | 0 | O | CH$_2$ | H | n-butyloxycarbonyl | OH | |
| 320 | 4-amidinophenyl | 1 | O | CH$_2$ | H | n-butyloxycarbonyl | OH | |
| 321 | 4-amidinophenyl | 2 | O | CH$_2$ | H | n-butyloxycarbonyl | OH | |
| 322 | 4-amidinophenyl | 0 | O | (CH$_2$)$_2$ | H | n-butyloxycarbonyl | OH | |
| 323 | 4-amidinophenyl | 0 | O | CH$_2$ | Me | n-butyloxycarbonyl | OH | |
| 324 | 4-amidinophenyl | 0 | O | CH$_2$ | Et | n-butyloxycarbonyl | OH | |
| 325 | 4-amidinophenyl | 0 | O | CH$_2$ | H | phenylsulfonyl | OH | |
| 326 | 4-amidinophenyl | 0 | O | CH$_2$ | H | 2-methylphenylsulfonyl | OH | |
| 327 | 4-amidinophenyl | 0 | O | CH$_2$ | H | 3-methylphenylsulfonyl | OH | |
| 328 | 4-amidinophenyl | 0 | O | CH$_2$ | H | 4-methylphenylsulfonyl | OH | |
| 329 | 4-amidinophenyl | 0 | O | CH$_2$ | H | benzylsulfonyl | OH | |
| 330 | 4-amidinophenyl | 0 | O | CH$_2$ | H | n-butylsulfonyl | OH | |
| 331 | 4-amidinophenyl | 0 | O | CH$_2$ | H | ethylsulfonyl | OH | |
| 332 | 4-amidinophenyl | 0 | O | CH$_2$ | H | benzyloxycarbonyl | OH | |
| 333 | 4-amidinophenyl | 0 | O | CH$_2$ | H | methyloxycarbonyl | OH | |
| 334 | 4-amidinophenyl | 0 | O | CH$_2$ | H | ethyloxycarbonyl | OH | |
| 335 | 4-guanidinophenyl | 0 | O | CH$_2$ | H | n-butyloxycarbonyl | OMe | 462 |
| 336 | 4-guanidinophenyl | 0 | O | CH$_2$ | H | n-butyloxycarbonyl | OH | |
| 337 | 4-guanidinophenyl | 0 | O | CH$_2$ | Me | n-butyloxycarbonyl | OH | |
| 338 | 4-guanidinophenyl | 0 | O | CH$_2$ | Et | n-butyloxycarbonyl | OH | |
| 339 | 4-guanidinophenyl | 1 | O | CH$_2$ | H | n-butyloxycarbonyl | OH | |
| 340 | 4-guanidinophenyl | 2 | O | CH$_2$ | H | n-butyloxycarbonyl | OH | |
| 341 | 4-guanidinophenyl | 0 | O | (CH$_2$)$_2$ | H | n-butyloxycarbonyl | OH | |
| 342 | 4-guanidinophenyl | 0 | O | CH$_2$ | H | benzyloxycarbonyl | OH | |
| 343 | 4-guanidinophenyl | 0 | O | CH$_2$ | H | methyloxycarbonyl | OH | |
| 344 | 4-guanidinophenyl | 0 | O | CH$_2$ | H | ethyloxycarbonyl | OH | |
| 345 | 4-guanidinophenyl | 0 | O | CH$_2$ | H | n-butylsulfonyl | OH | |
| 346 | 4-guanidinophenyl | 0 | O | CH$_2$ | H | benzylsulfonyl | OH | |
| 347 | 4-guanidinophenyl | 0 | O | CH$_2$ | H | phenylsulfonyl | OH | |
| 348 | 4-guanidinophenyl | 0 | O | CH$_2$ | H | 2-methylphenylsulfonyl | OH | |
| 349 | 4-guanidinophenyl | 0 | O | CH$_2$ | H | 3-methylphenylsulfonyl | OH | |
| 350 | 4-guanidinophenyl | 0 | O | CH$_2$ | H | 4-methylphenylsulfonyl | OH | |
| 351 | 4-guanidinophenyl | 0 | O | CH$_2$ | Me | 2-methylphenylsulfonyl | OH | |
| 352 | 4-guanidinophenyl | 0 | O | CH$_2$ | H | 3,5-dimethylisoxazol-4-ylsulfonyl | OH | |

TABLE 2

| Ex No. | R¹—Ar | m | A | W | R⁵ | X | Y | [(M + 1)⁺] MS |
|---|---|---|---|---|---|---|---|---|
| 353 | 4-aminophenyl 323 | 0 | O | SCH$_2$ | H | CH$_2$ | OMe | |
| 354 | 4-aminophenyl | 0 | O | SCH$_2$ | H | CH$_2$ | OH | |
| 355 | 4-aminophenyl | 1 | O | SCH$_2$ | H | CH$_2$ | OH | |
| 356 | 4-aminophenyl | 2 | O | SCH$_2$ | H | CH$_2$ | OH | |
| 357 | 4-aminophenyl | 0 | O | SCH$_2$ | Me | CH$_2$ | OH | |
| 358 | 4-aminophenyl | 0 | O | SCH$_2$ | Et | CH$_2$ | OH | |
| 359 | 4-aminophenyl | 0 | O | S(CH$_2$)$_2$ | H | CH$_2$ | OH | |
| 360 | 4-aminophenyl | 0 | O | S(CH$_2$)$_3$ | H | CH$_2$ | OH | |
| 361 | 4-aminophenyl | 1 | O | S(CH$_2$)$_2$ | H | CH$_2$ | OH | |
| 363 | 4-aminophenyl | 1 | O | SCH$_2$ | Et | CH$_2$ | OH | |
| 363 | 4-(N-methylamino)-phenyl | 1 | O | SCH$_2$ | H | CH$_2$ | OH | |
| 364 | 4-(N-methylamino)-phenyl | 1 | O | SCH$_2$ | Et | CH$_2$ | OH | |
| 365 | 4-(N-methylamino)-phenyl | 0 | O | SCH$_2$ | H | CH$_2$ | OH | |
| 366 | 4-(N,N-dimethylamino)-phenyl | 1 | O | SCH$_2$ | H | CH$_2$ | OH | |
| 367 | 4-(N,N-dimethylamino)-phenyl | 0 | O | SCH$_2$ | H | CH$_2$ | OH | |
| 368 | 4-(N,N-dimethylamino)-phenyl | 1 | O | SCH$_2$ | Et | CH$_2$ | OH | |
| 369 | 4-(N,N-dimethylamino)-phenyl | 1 | O | S(CH$_2$)$_2$ | H | CH$_2$ | OH | |
| 370 | 4-amino-2-fluorophenyl | 0 | O | SCH$_2$ | H | CH$_2$ | OH | |
| 371 | 4-amino-2-fluorophenyl | 1 | O | SCH$_2$ | H | CH$_2$ | OH | |
| 372 | 4-amino-2-fluorophenyl | 0 | O | SCH$_2$ | Me | CH$_2$ | OH | |
| 373 | 4-amino-2-fluorophenyl | 0 | O | SCH$_2$ | Et | CH$_2$ | OH | |
| 374 | 4-amino-2-fluorophenyl | 0 | O | S(CH$_2$)$_2$ | H | CH$_2$ | OH | |
| 375 | 4-amino-2-fluorophenyl | 1 | O | S(CH$_2$)$_2$ | H | CH$_2$ | OH | |
| 376 | 4-amino-3-fluorophenyl | 0 | O | S(CH$_2$)$_2$ | H | CH$_2$ | OH | |
| 377 | 4-amino-3-fluorophenyl | 1 | O | S(CH$_2$)$_2$ | H | CH$_2$ | OH | |
| 378 | 4-pyperidinyl | 0 | O | SCH$_2$ | H | CH$_2$ | OH | |
| 379 | 4-pyperidinyl | 1 | O | SCH$_2$ | H | CH$_2$ | OH | |
| 380 | 4-pyperidinyl | 2 | O | SCH$_2$ | H | CH$_2$ | OH | |
| 381 | 4-pyperidinyl | 3 | O | SCH$_2$ | H | CH$_2$ | OH | |
| 382 | 4-pyperidinyl | 0 | O | S(CH$_2$)$_2$ | H | CH$_2$ | OH | |
| 383 | 4-pyperidinyl | 0 | O | S(CH$_2$)$_3$ | H | CH$_2$ | OH | |
| 384 | 4-pyperidinyl | 1 | O | S(CH$_2$)$_2$ | H | CH$_2$ | OH | |
| 385 | 4-guanidinophenyl 365 | 0 | O | SCH$_2$ | H | CH$_2$ | OMe | |
| 386 | 4-guanidinophenyl | 0 | O | SCH$_2$ | H | CH$_2$ | OH | |
| 387 | 4-guanidinophenyl | 1 | O | SCH$_2$ | H | CH$_2$ | OH | |
| 388 | 4-guanidinophenyl | 1 | O | S(CH$_2$)$_2$ | H | CH$_2$ | OH | |
| 389 | 4-guanidinophenyl | 1 | O | SCH$_2$ | Et | CH$_2$ | OH | |
| 390 | 4-guanidinophenyl | 2 | O | SCH$_2$ | H | CH$_2$ | OH | |
| 391 | 4-guanidinophenyl | 0 | O | S(CH$_2$)$_2$ | H | CH$_2$ | OH | |
| 392 | 4-guanidinophenyl 455 | 0 | O | SCH$_2$ | H |  | OMe | |
| 393 | 4-guanidinophenyl | 0 | O | SCH$_2$ | H | 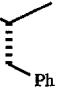 | OH | |
| 394 | 4-guanidinophenyl | 1 | O | SCH$_2$ | H | 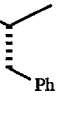 | OH | |
| 395 | 4-guanidinophenyl | 2 | O | SCH$_2$ | H |  | OH | |

TABLE 2-continued

| Ex No. | R¹—Ar | m | A | W | R⁵ | X | Y | [(M+1)⁺] MS |
|---|---|---|---|---|---|---|---|---|
| 396 | 4-guanidinophenyl | 0 | O | S(CH₂)₂ | H | CH(Ph) | OH | |
| 397 | 4-guanidinophenyl | 1 | O | SCH₂ | Et | CH(Ph) | OH | |
| 398 | 4-guanidinophenyl | 1 | O | S(CH₂)₂ | H | CH(Ph) | OH | |
| 399 | 4-amidinophenyl 454 | 0 | O | SCH₂ | H | CH(Ph) | OEt | |
| 400 | 4-amidinophenyl | 0 | O | SCH₂ | H | CH(Ph) | OH | |
| 401 | 4-amidinophenyl | 1 | O | SCH₂ | H | CH(Ph) | OH | |
| 402 | 4-amidinophenyl | 2 | O | SCH₂ | H | CH(Ph) | OH | |
| 403 | 4-amidinophenyl | 0 | O | S(CH₂)₂ | H | CH(Ph) | OH | |
| 404 | 4-aminophenyl | 0 | O | SCH₂ | H | CH(NHCO₂n-Bu) | OMe | 452 |
| 405 | 4-aminophenyl | 0 | O | SCH₂ | H | CH(NHCO₂n-Bu) | OH | |
| 406 | 4-aminophenyl | 1 | O | SCH₂ | H | CH(NHCO₂n-Bu) | OH | |
| 407 | 4-aminophenyl | 2 | O | SCH₂ | H | CH(NHCO₂n-Bu) | OH | |
| 408 | 4-aminophenyl | 1 | O | S(CH₂)₂ | H | CH(NHCO₂n-Bu) | OH | |

TABLE 2-continued

| Ex No. | R¹—Ar | m | A | W | R⁵ | X | Y | [(M + 1)⁺] MS |
|---|---|---|---|---|---|---|---|---|
| 409 | 4-aminophenyl | 1 | O | SCH$_2$ | Et | –CH(CH$_3$)CH$_2$NHCO$_2$n-Bu | OH | |
| 410 | 4-aminophenyl | 0 | O | SCH$_2$ | H | –CH(CH$_3$)CH$_2$NHCBz | OH | |
| 411 | 4-aminophenyl | 1 | O | SCH$_2$ | H | –CH(CH$_3$)CH$_2$NHCBz | OH | |
| 412 | 4-aminophenyl | 2 | O | SCH$_2$ | H | –CH(CH$_3$)CH$_2$NHCBz | OH | |
| 413 | 4-aminophenyl | 0 | O | SCH$_2$ | Me | –CH(CH$_3$)CH$_2$NHCBz | OH | |
| 414 | 4-aminophenyl | 1 | O | S(CH$_2$)$_2$ | H | –CH(CH$_3$)CH$_2$NHCBz | OH | |
| 415 | 4-aminophenyl | 0 | O | SCH$_2$ | H | –CH(CH$_3$)CH$_2$NHSO$_2$Ph | OH | |
| 416 | 4-aminophenyl | 1 | O | SCH$_2$ | H | –CH(CH$_3$)CH$_2$NHSO$_2$Ph | OH | |
| 417 | 4-aminophenyl | 1 | O | S(CH$_2$)$_2$ | H | –CH(CH$_3$)CH$_2$NHSO$_2$Ph | OH | |
| 418 | 4-aminophenyl | 0 | O | SCH$_2$ | Et | –CH(CH$_3$)CH$_2$NHSO$_2$Ph | OH | |
| 419 | 4-aminophenyl | 0 | O | SCH$_2$ | H | –CH(CH$_3$)CH$_2$NHSO$_2$-m-Ph | OH | |
| 420 | 4-aminophenyl | 0 | O | SCH$_2$ | H | –CH(CH$_3$)CH$_2$NHSO$_2$-o-Ph | OH | |
| 421 | 4-aminophenyl | 0 | O | SCH$_2$ | H | –CH(CH$_3$)CH$_2$NHSO$_2$-p-Ph | OH | |

TABLE 2-continued

| Ex No. | R¹—Ar | m | A | W | R⁵ | X | Y | Y [(M+1)⁺] MS |
|---|---|---|---|---|---|---|---|---|
| 422 | 4-guanidinophenyl | 0 | O | $SCH_2$ | H | CH(NHCO₂n-Bu)— | OMe | 494 |
| 423 | 4-guanidinophenyl | 0 | O | $SCH_2$ | H | CH(NHCO₂n-Bu)— | OH | |
| 424 | 4-guanidinophenyl | 1 | O | $SCH_2$ | H | CH(NHCO₂n-Bu)— | OH | |
| 425 | 4-guanidinophenyl | 2 | O | $SCH_2$ | H | CH(NHCO₂n-Bu)— | OH | |
| 426 | 4-guanidinophenyl | 1 | O | $S(CH_2)_2$ | H | CH(NHCO₂n-Bu)— | OH | |
| 427 | 4-guanidinophenyl | 1 | O | $SCH_2$ | Et | CH(NHCO₂n-Bu)— | OH | |
| 428 | 4-guanidinophenyl | 0 | O | $SCH_2$ | H | CH(NHCBz)— | OH | |
| 429 | 4-guanidinophenyl | 1 | O | $SCH_2$ | H | CH(NHCBz)— | OH | |
| 430 | 4-guanidinophenyl | 2 | O | $SCH_2$ | H | CH(NHCBz)— | OH | |
| 431 | 4-guanidinophenyl | 0 | O | $SCH_2$ | Me | CH(NHCBz)— | OH | |
| 432 | 4-guanidinophenyl | 1 | O | $S(CH_2)_2$ | H | CH(NHCBz)— | OH | |
| 433 | 4-aguanidinophenyl | 0 | O | $SCH_2$ | H | CH(NHSO₂Ph)— | OH | |
| 434 | 4-guanidinophenyl | 1 | O | $SCH_2$ | H | CH(NHSO₂Ph)— | OH | |

TABLE 2-continued

| Ex No. | R¹—Ar | m | A | W | R⁵ | X | Y | [(M + 1)⁺] MS |
|---|---|---|---|---|---|---|---|---|
| 435 | 4-guanidinophenyl | 1 | O | S(CH₂)₂ | H | NHSO₂Ph | OH | |
| 436 | 4-guanidinophenyl | 0 | O | SCH₂ | Et | NHSO₂Ph | OH | |
| 437 | 4-guanidinophenyl | 0 | O | SCH₂ | H | NHSO₂-m-Ph | OH | |
| 438 | 4-guanidinophenyl | 0 | O | SCH₂ | H | NHSO₂-o-Ph | OH | |
| 439 | 4-guanidinophenyl | 0 | O | SCH₂ | H | NHSO₂-p-Ph | OH | |
| 440 | 4-amidinophenyl | 0 | O | SCH₂ | H | NHCO₂n-Bu | OMe | 495 |
| 441 | 4-amidinophenyl | 0 | O | SCH₂ | H | NHCO₂n-Bu | OH | |
| 442 | 4-amidinophenyl | 1 | O | SCH₂ | H | NHCO₂n-Bu | OH | |
| 443 | 4-amidinophenyl | 2 | O | SCH₂ | H | NHCO₂n-Bu | OH | |
| 444 | 4-amidinophenyl | 1 | O | S(CH₂)₂ | H | NHCO₂n-Bu | OH | |
| 445 | 4-amidinophenyl | 1 | O | SCH₂ | Et | NHCO₂n-Bu | OH | |
| 446 | 4-amidinophenyl | 0 | O | SCH₂ | H | NHCBz | OH | |
| 447 | 4-amidinophenyl | 1 | O | SCH₂ | H | NHCBz | OH | |

TABLE 2-continued $$R^1-Ar-(\ )_m-A-W-\underset{N-N}{\diagup\diagdown}-C(O)-N(R^5)-X-C(O)-Y$$

| Ex No. | R¹—Ar | m | A | W | R⁵ | X | Y | [(M + 1)⁺] MS |
|---|---|---|---|---|---|---|---|---|
| 448 | 4-amidinophenyl | 2 | O | SCH₂ | H | CH(NHCBz)— | OH | |
| 449 | 4-amidinophenyl | 0 | O | SCH₂ | Me | CH(NHCBz)— | OH | |
| 450 | 4-amidinophenyl | 1 | O | S(CH₂)₂ | H | CH(NHCBz)— | OH | |
| 451 | 4-amidinophenyl | 0 | O | SCH₂ | H | CH(NHSO₂Ph)— | OH | |
| 452 | 4-amidinophenyl | 1 | O | SCH₂ | H | CH(NHSO₂Ph)— | OH | |
| 453 | 4-amidinophenyl | 1 | O | S(CH₂)₂ | H | CH(NHSO₂Ph)— | OH | |
| 454 | 4-amidinophenyl | 0 | O | SCH₂ | Et | CH(NHSO₂Ph)— | OH | |
| 455 | 4-amidinophenyl | 0 | O | SCH₂ | H | CH(NHSO₂-m-Ph)— | OH | |
| 456 | 4-amidinophenyl | 0 | O | SCH₂ | H | CH(NHSO₂-o-Ph)— | OH | |
| 457 | 4-amidinophenyl | 0 | O | SCH₂ | H | CH(NHSO₂-p-Ph)— | OH | |

Utility

The compounds of this invention possess antiplatelet efficacy, as evidenced by their activity in standard platelet aggregation assays or platelet fibrinogen binding assays, as described below. A compound is considered to be active in these assays if it has an $IC_{50}$ value of less than about 1 mM. Platelet aggregation and fibrinogen binding assays which may be used to demonstrate the antiplatelet activity of the compounds of the invention are described below.

Platelet Aggregation Assay: Venous blood was obtained from the arm of a healthy human donor who was drug-free and aspirin-free for at least two weeks prior to blood collection. Blood was collected into 10 mL citrated Vacutainer tubes. The blood was centrifuged for 15 minutes at 150× g at room temperature, and platelet-rich plasma (PRP) was removed. The remaining blood was centrifuged for 15 minutes at 1500× g at room temperature, and platelet-poor plasma (PPP) was removed. Samples were assayed on a aggregometer (PAP-4 Platelet Aggregation Profiler), using PPP as the blank (100% transmittance). 200 μL of PRP was added to each micro test tube, and transmittance was set to 0%. 20 μL of various agonists (ADP, collagen, arachidonate, epinephrine, thrombin) were added to each tube, and the aggregation profiles were plotted (% transmittance versus time). The results are expressed as % inhibition of agonistinduced platelet aggregation. For the $IC_{50}$ evaluation, the test compounds were added at various concentrations prior to the activation of the platelets.

Ester prodrugs were preincubated ($10^{-3}$M F.C.) with 100 IU/mL Porcine liver esterase (Sigma Chemical Co., St. Louis, Mo., #E-3128) for 2 hours at 37° C. Aliquots are then diluted in 0.1M Tris, p H 7.4, to the desired concentrations. Aliquots of 20 µl of the esterase pretreated prodrugs are added to 200 µl of human platelet rich plasma. Samples were placed in platelet profiler (aggregometer) for 8 minutes at 37° C., followed by the addition of 100 µM Adenosine Diphosphate, (Sigma Chemical Co., St. Louis, Mo., #A-6521), to induce platelet aggregation. Platelet aggregation was allowed to proceed for 5 minutes. Percent inhibition is calculated using percent aggregation in the presence of the test compound divided by percent aggregation of control, times 100. This value is subtracted from 100, yielding percent inhibition. Calculation of $IC_{50}$ is performed on a Texas Instruments TI59 with an $IC_{50}$ program.

Purified GPIIb/IIIa-Fibrinogen Binding ELISA

The following reagents are used in the GPIIb/IIIa-fibrinogen binding ELISA:

purified GPIIb/IIIa (148.8 µg/mL);

biotinylated fibrinogen (~1 mg/mL or 3000 nM);

anti-biotin alkaline phosphatase conjugate (Sigma no. A7418);

flat-bottom, high binding, 96-well plates (Costar Cat. no. 3590);

phosphatase substrate (Sigma 104) (40 mg capsules);

bovine serum albumin (BSA) (Sigma no. A3294);

Alkaline Phosphatase buffer −0.1M glycine-HCl, 1 mM $MgCl_2.6H_2O$, 1 mM $ZnCl_2$, pH 10.4;

Binding buffer −20 mM Tris-HCl, 150 mM NaCl, 1 mM $CaCl_2.2H_2O$, 0.02% $NAN_3$, pH 7.0;

Buffer A −50 mM Tris-HCl, 100 mM NaCl, 2 mM $CaCl_2.2H_2O$, 0.02% $NAN_3$, pH 7.4;

Buffer A+3.5% BSA (Blocking buffer);

Buffer A+0.1% BSA (Dilution buffer);

2N NaOH.

The following method steps are used in the GPIIb/IIIa-fibrinogen binding ELISA:

Coat plates with GPIIb/IIIa in Binding buffer (125 ng/100 µL/well) overnight at 4° C. (Leave first column uncoated for non-specific binding). Cover and freeze plates at −70° C. until used. Thaw plate 1 hour at room temperature or overnight at 4° C. Discard coating solution and wash once with 200 µL Binding buffer per well. Block plate 2 hours at room temperature on shaker with 200 µL Buffer A+3.5% BSA (Blocking buffer) per well. Discard Blocking buffer and wash once with 200 µL Buffer A+0.1% BSA (Dilution buffer) per well. Pipet 11 µL of test compound (10× the concentration to be tested in Dilution buffer) into duplicate wells. Pipet 11 µL Dilution buffer into non-specific and total binding wells. Add 100 µL Biotinylated fibrinogen (1/133 in Dilution buffer, final concentration=20 nM) to each well. Incubate plates for 3 hours at room temperature on a plate shaker. Discard assay solution and wash twice with 300 µL Binding buffer per well. Add 100 µL Anti-biotin alkaline phosphatase conjugate (1/1500 in Dilution buffer) to each well. Incubate plates for 1 hour at room temperature on plate shaker. Discard conjugate and wash twice with 300 5l Binding buffer per well. Add 100 µL Phosphatase substrate (1.5 mg/mL in Alkaline phosphatase buffer) to each well. Incubate plate at room temperature on shaker until color develops. Stop color development by adding 25 µL 2N NaOH per well. Read plate at 405 nm. Blank against non-specific binding (NSB) well. % Inhibition is calculated as 100−(Test Compound Abs/Total Abs)×100.

Platelet-Fibrinogen Binding Assay: Binding of $^{125}$I-fibrinogen to platelets was performed as described by Bennett et al. (1983) Proc. Natl. Acad. Sci. USA 80: 2417–2422, with some modifications as described below. Human PRP (h-PRP) was applied to a Sepharose column for the purification of platelet fractions. Aliquots of platelets ($5 \times 10^8$ cells) along with 1 mM calcium chloride were added to removable 96 well plates prior to the activation of the human gel purified platelets (h-GPP). Activation of the human gel purified platelets was achieved using ADP, collagen, arachidonate, epinephrine, and/or thrombin in the presence of the ligand, $^{125}$I-fibrinogen. The $^{125}$I-fibrinogen bound to the activated platelets was separated from the free form by centrifugation and then counted on a gamma counter. For an $IC_{50}$ evaluation, the test compounds were added at various concentrations prior to the activation of the platelets.

The compounds of Formula I of the present invention may also possess thrombolytic efficacy, that is, they are capable of lysing (breaking up) already formed platelet-rich fibrin blood clots, and thus are useful in treating a thrombus formation, as evidenced by their activity in the tests described below. Preferred compounds of the present invention for use in thrombolysis include those compounds having an $IC_{50}$ value (that is, the molar concentration of the compound capable of achieving 50% clot lysis) of less than about 1 µM, more preferably an $IC_{50}$ value of less than about 0.1 µM.

Thrombolytic Assay: Venous blood was obtained from the arm of a healthy human donor who was drug-free and aspirin free for at least two weeks prior to blood collection, and placed into 10 ml citrated Vacutainer tubes. The blood was centrifuged for 15 minutes at 1500× g at room temperature, and platelet rich plasma (PRP) was removed. To the PRP was then added $1 \times 10^{-3}$M of the agonist ADP, epinephrine, collagen, arachidonate, serotonin or thrombin, or a mixture thereof, and the PRP incubated for 30 minutes. The PRP was centrifuged for 12 minutes at 2500× g at room temperature. The supernatant was then poured off, and the platelets remaining in the test tube were resuspended in platelet poor plasma (PPP), which served as a plasminogen source. The suspension was then assayed on a Coulter Counter (Coulter Electronics, Inc., Hialeah, Fla.), to determine the platelet count at the zero time point. After obtaining the zero time point, test compounds were added at various concentrations. Test samples were taken at various time points and the platelets were counted using the Coulter Counter. To determine the percent of lysis, the platelet count at a time point subsequent to the addition of the test compound was subtracted from the platelet count at the zero time point, and the resulting number divided by the platelet count at the zero time point. Multiplying this result by 100 yielded the percentage of clot lysis achieved by the test compound. For the $IC_{50}$ evaluation, the test compounds were added at various concentrations, and the percentage of lysis caused by the test compounds was calculated.

The compounds of Formula I of the present invention are also useful for administration in combination with anticoagulant agents such as warfarin or heparin, or antiplatelet agents such as aspirin, piroxicam or ticlopidine, or thrombin inhibitors such as boropeptides, hirudin or argatroban, or thrombolytic agents such as tissue plasminogen activator, anistreplase, urokinase or streptokinase, or combinations thereof.

The compounds of Formula I of the present invention may also be useful as antagonists of other integrins such as for example, the $\alpha_v/\beta_3$ or vitronectin receptor, $\alpha_4/\beta_1$ or $\alpha_5/\beta_1$ and as such may also have utility in the treatment and diagnosis of osteoporosis, cancer metastasis, diabetic retinopathy, rheumatoid arthritis, inflammation, and autoimmune disorders. The compounds of Formula I of the present invention may be useful for the treatment or prevention of other diseases which involve cell adhesion processes, including, but not limited to, inflammation, bone degradation, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, inflammatory bowel disease and other autoimmune diseases.

Table A below sets forth the antiplatelet activity of representative compounds of the present invention. The indicated compounds were tested for their ability to inhibit platelet aggregation (using platelet rich plasma (PRP)). The $IC_{50}$ value (the concentration of antagonist which inhibits platelet aggregation by 50% relative to a control lacking the antagonist) is shown. In Table A the $IC_{50}$ values are expressed as: +++=$IC_{50}$ of <10 µM; ++=$IC_{50}$ of 10–50M; +=$IC_{50}$ of 50–100 µM (µM=micromolar).

TABLE A

| Example Number | Platelet Aggregation Assay $IC_{50}$ (without esterase) | Platelet Aggregation Assay $IC_{50}$ (with esterase) |
|---|---|---|
| 1 | | +++ |
| 2 | +++ | |
| 25 | | +++ |
| 26 | +++ | |
| 44 | | +++ |
| 63 | +++ | |
| 64 | | +++ |
| 65 | +++ | |
| 88 | | +++ |
| 89 | +++ | |
| 96 | | +++ |
| 97 | +++ | |
| 133 | | +++ |
| 134 | +++ | |
| 145 | | +++ |
| 146 | | +++ |
| 170 | | + |
| 171 | +++ | |
| 192 | | +++ |
| 193 | +++ | |
| 242 | | ++ |
| 258 | | +++ |
| 318 | | + |
| 335 | | +++ |
| 392 | | ++ |
| 399 | | ++ |
| 440 | | +++ |

Dosage and Formulation

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an anti-aggregation agent. Finally, the compounds of the invention may also be administered intranasally.

The compounds of this invention can be administered by any means that produces contact of the active agent with the agent's site of action, glycoprotein IIb/IIIa (GPIIb/IIIa), in the body of a mammal. They can be administered by any conventional means available for use in conjunction with pharmaceuticals, either as individual therapeutic agents or in a combination of therapeutic agents, such as a second antiplatelet agent such as aspirin or ticlopidine which are agonist-specific. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules are prepared by filling standard two-piece hard gelatin capsules each with 1–20 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 1–20 milligrams of the active ingredient. The capsules are washed and dried.

Tablets

A large number of tablets are prepared by conventional procedures so that the dosage unit was 1–20 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 1–20 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent selected from: an anti-coagulant agent such as warfarin or heparin; an anti-platelet agent such as aspirin, piroxicam or ticlopidine; a thrombin inhibitor such as a boropeptide thrombin inhibitor, or hirudin; or a thrombolytic agent such as plasminogen activators, such as tissue plasminogen activator, anistreplase, urokinase or streptokinase. The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent (anti-coagulant agent, anti-platelet agent, thrombin inhibitor, and/or thrombolytic agent) may be administered essentially at the same time, or in any order; for example the compound of Formula I may be administered first, followed by administration of the second agent (anti-coagulant agent, anti-platelet agent, thrombin inhibitor, and/or thrombolytic agent). When not administered at the same time, preferably the administration of the compound of Formula I and the second therapeutic agent occurs less than about one hour apart.

A preferable route of administration of the compound of Formula I is oral. Although it is preferable that the compound of Formula I and the second therapeutic agent (anti-coagulant agent, anti-platelet agent, thrombin inhibitor, and/or thrombolytic agent) are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Although the proper dosage of the compound of Formula I when administered in combination with the second therapeutic agent will be readily ascertainable by a medical practitioner skilled in the art, once armed with the present disclosure, by way of general guidance, where the compounds of this invention are combined with anti-coagulant agents, for example, a daily dosage may be about 0.1 to 100 milligrams of the compound of Formula I and about 1 to 7.5 milligrams of the anti-coagulant, per kilogram of patient body weight. For a tablet dosage form, the novel compounds of this invention generally may be present in an amount of about 1 to 10 milligrams per dosage unit, and the anti-coagulant in an amount of about 1 to 5 milligrams per dosage unit.

Where the compounds of Formula I are administered in combination with a second anti-platelet agent, by way of general guidance, typically a daily dosage may be about 0.01 to 25 milligrams of the compound of Formula I and about 50 to 150 milligrams of the additional anti-platelet agent, preferably about 0.1 to 1 milligrams of the compound of Formula I and about 1 to 3 milligrams of antiplatelet agents, per kilogram of patient body weight.

Further, by way of general guidance, where the compounds of Formula I are administered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the inhibition of platelet aggregation, the treatment of blood clots, and/or the treatment of thromboembolic disorders, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

What is claimed is:

1. A compound of the formula

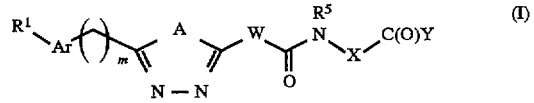

or a pharmaceutically acceptable salt thereof wherein:

$R^1$ is selected from $R^2HN-$, $R^2HN(R^2N=)C-$, $R^2HN(CH_2)_qZ-$, $R^2HN(R^2N=)C(CH_2)_qZ-$, $R^2HN(R^2N=)CN(R^2)-$, $R^2HNC(O)-$, $R^2(R^5O)N(R^2N=)C-$, or $R^2HN(R^5ON=)C-$;

alternatively, $R^1$ is H when Ar is -(piperidinyl)-;

q is 1–3;

Z is selected from a bond (i.e. is absent), O, S, or S(=O), S(=O)$_2$;

$R^2$ is selected from H, aryl ($C_1$–$C_{10}$ alkoxy)carbonyl, or $C_1$–$C_{10}$ alkoxycarbonyl, $C_1$–$C_4$ alkyl, $C_3$–$C_6$ alkenyl;

$R^5$ is selected from H or $C_1$–$C_{10}$ alkyl substituted with 0–1 $R^{4b}$;

$R^{4b}$ is selected from $C_1$–$C_6$ alkyl, $C_2$–$C_6$ alkenyl, $C_2$–$C_6$ alkynyl, $C_3$–$C_7$ cycloalkyl, $C_7$–$C_{14}$ bicycloalkyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, $C_1$–$C_6$ alkylcarbonyl, $C_6$–$C_{10}$ aryl, —N($R^{12}$)$R^{13}$; halo, $CF_3$, CN, $C_1$–$C_6$ alkoxycarbonyl, carboxy, piperidinyl, morpholinyl or pyridinyl;

Ar is selected from:
-(piperidinyl)- substituted with 0–2 $R^{6a}$,
-(phenyl)- substituted with 0–2 $R^{6a}$, or
-(pyridyl)- substituted with 0–2 $R^{6a}$;

$R^{6a}$ is selected from $C_1$–$C_4$ alkyl, $C_1$–$C_4$ alkoxy, halo, $CF_3$, $NO_2$, or $NR^{12}R^{13}$;

A is selected from O or S;

W is selected from —$(CH_2)_n$— or —$S(CH_2)_{n-1}$—;

X is selected from —$C(CH_2$—Ph$)H$—, —$CH_2$—, —$CH_2C(NHR^{12})H$— or —$C(CH_2NHR^{12})H$—;

Y is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, $C_{10}$ to $C_{14}$ (5-aryl-1,3-dioxa-cyclopenten-2-one-yl)methyloxy, $(R^2)HN$—$(C_1$–$C_{10}$ alkoxy)—;

m is 0–2;

n is 1–4; and $R^{12}$ and $R^{13}$ are each independently selected from H; $C_1$–$C_{10}$ alkyl; $C_1$–$C_{10}$ alkoxycarbonyl; $C_1$–$C_{10}$ alkylcarbonyl; $C_1$–$C_{10}$ alkylsulfonyl; aryl, aryl($C_1$–$C_{10}$ alkyl)sulfonyl, and arylsulfonyl wherein said aryls and heteroaryls are substituted with 0–3 substituents selected from the group consisting of: $C_1$–$C_4$ alkyl, $C_1$–$C_4$ alkoxy, halo, $CF_3$, and $NO_2$; and heteroaryl ($C_1$–$C_4$ alkyl)sulfonyl, heteroarylcarbonyl, heteroarylsulfonyl, and heteroarylalkylcarbonyl wherein said heteroaryls are substituted with 0–3 substituents selected from the group consisting of: $C_1$–$C_4$ alkyl, $C_1$–$C_4$ alkoxy, halo, $CF_3$, and $NO_2$;

provided that m and n are chosen such that the number of atoms connecting $R^1$ and y is in the range of 10–18.

2. A compound of the formula

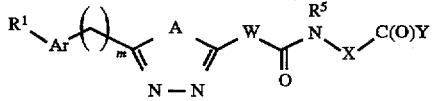

wherein
$R^1$ is selected from $R^2NHC(\!=\!NR^2)$— or $R^2NHC(\!=\!NR^2)NH$—;

$R^2$ is selected from H, $C_1$–$C_{10}$ alkoxycarbonyl, or $C_1$–$C_4$ alkyl;

$R^5$ is selected from H or $C_1$–$C_4$ alkyl

Ar is selected from -(phenyl)- substituted with 0–2 $R^{6a}$, or -(piperidinyl)- substituted with 0–2 $R^{6a}$;

$R^{6a}$ is selected from $C_1$–$C_4$ alkyl, $C_1$–$C_4$ alkoxy, halo, $CF_3$, $NO_2$, or $NR^{12}R^{13}$;

A is selected from O or S;

W is selected from —$(CH_2)_n$— or —$S(CH_2)_{n-1}$—;

X is selected from —$CH_2C(NHR^{12})H$— or —$C(CH_2NHR^{12})H$—;

Y is selected from:
hydroxy;
$C_1$ to $C_{10}$ alkoxy;
methylcarbonyloxymethoxy-;
ethylcarbonyloxymethoxy-;
t-butylcarbonyloxymethoxy-;
cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl) methoxy-;
(1,3-dioxa-5-phenyl-cyclopenten-2-on-4-yl)methoxy-;
1-(2-(2-methoxypropyl)carbonyloxy)ethoxy-;

m is 1 or 2;

n is 1 or 2;

$R^{12}$ is selected from H; $C_1$–$C_6$ alkyl; $C_1$–$C_4$ alkoxycarbonyl; $C_1$–$C_6$ alkylcarbonyl; $C_1$–$C_6$ alkylsulfonyl; aryl, aryl($C_1$–$C_4$ alkyl)sulfonyl, and arylsulfonyl wherein said aryls are substituted with 0–3 substituents selected from the group consisting of: $C_1$–$C_4$ alkyl, $C_1$–$C_4$ alkoxy, halo, $CF_3$, and $NO_2$; and heteroaryl($C_1$–$C_4$ alkyl)sulfonyl, heteroarylsulfonyl, heteroarylcarbonyl or heteroarylmethylcarbonyl wherein said heteroaryls are substituted with 0–3 substituents selected from the group consisting of: $C_1$–$C_4$ alkyl, $C_1$–$C_4$ alkoxy, halo, $CF_3$, and $NO_2$; and $R^{13}$ is H; or a pharmaceutically acceptable salt thereof.

3. A compound of claim 2 selected from the group consisting of:

Methyl $N^3$-[2-{2-(4-amidinophenyl)-1,3,4-thiadiazol-5-yl}-acetyl]-$N^2$-(n-butyloxycarbonyl)-2,3-(S)-diaminopropionate TFA salt $N^3$-[2-{2-(4-amidinophenyl)-1,3,4-thiadiazol-5-yl}-acetyl]-$N^2$-(n-butyloxycarbonyl)-2,3-(S)-diaminopropionic acid HCl salt Methyl $N^3$-[2-{2-(4-amidinophenyl)-1,3,4-thiadiazol-5-yl}-acetyl]-$N^2$-(3-methylphenylsulfonyl)-2,3-(S)-diaminopropionate TFA salt $N^3$-[2-{2-(4-amidinophenyl)-1,3,4-thiadiazol-5-yl}-acetyl]-$N^2$-(3-methylphenylsulfonyl)-2,3-(S)-diaminopropionic acid HCl salt Methyl $N^3$-[2-{2-(4-N-methylamidinophenyl)-1,3,4-thiadiazol-5-yl}-acetyl]-$N^2$-(3-methylphenylsulfonyl)-2,3-(S)-diaminopropionate TFA salt $N^3$-[2-{2-(4-N-methylamidinophenyl)-1,3,4-thiadiazol-5-yl}-acetyl]-$N^2$-(3-methylphenylsulfonyl)-2,3-(S)-diaminopropionic acid HCl salt Methyl $N^3$-[2-{2-(4-N-n-butylamidinophenyl)-1,3,4-thiadiazol-5-yl}-acetyl]-$N^2$-(3-methylphenylsulfonyl)-2,3-(S)-diaminopropionate TFA salt $N^3$-[2-{2-(4-N-n-butylamidinophenyl)-1,3,4-thiadiazol-5-yl}-acetyl]-$N^2$-(3-methylphenylsulfonyl)-2,3-(S)-diaminopropionic acid HCl salt Methyl $N^3$-[2-{2-(4-amidinophenyl)-1,3,4-thiadiazol-5-yl}-acetyl]-$N^2$-(2-methylphenylsulfonyl)-2,3-(S)-diaminopropionate TFA salt $N^3$-[2-{2-(4-amidinophenyl)-1,3,4-thiadiazol-5-yl}-acetyl]-$N^2$-(2-methylphenylsulfonyl)-2,3-(S)-diaminopropionic acid HCl salt Methyl $N^3$-[2-{2-(4-amidinophenyl)-1,3,4-thiadiazol-5-yl}-acetyl]-$N^2$-(3,5-dimethylisoxazol-4-ylsulfonyl)-2,3-(S)-diaminopropionate TFA salt $N^3$-[2-{2-(4-amidinophenyl)-1,3,4-thiadiazol-5-yl}-acetyl]-$N^2$-(3,5-dimethylisoxazol-4-ylsulfonyl)-2,3-(S)-diaminopropionic acid HCl salt Methyl $N^3$-[2-{2-(4-piperidinyl)-1,3,4-thiadiazol-5-yl}-acetyl]-$N^2$-(3-methylphenylsulfonyl)-2,3-(S)-diaminopropionate TFA salt Methyl $N^3$-[4-{2-(4-piperidinyl)-1,3,4-thiadiazol-5-yl}-butyryl]-$N^2$-(3-methylphenylsulfonyl)-2,3-(S)-diaminopropionate TFA salt $N^3$-[4-{2-(4-piperidinyl)-1,3,4-thiadiazol-5-yl}-butyryl]-$N^2$-(3-methylphenylsulfonyl)-2,3-(S)-diaminopropionic acid TFA salt Methyl $N^3$-[2-{2-(4-N,N'-di(trifluoroethyl)amidinophenyl)-1,3,4-thiadiazol-5-yl}-acetyl]-$N^2$-(3-methylphenylsulfonyl)-2,3-(S)-diaminopropionate Methyl $N^3$-[2-{2-(4-guanidinophenyl)-1,3,4-thiadiazol-5-yl}-acetyl]-$N^2$-(3-methylphenylsulfonyl)-2,3-(S)-diaminopropionate TFA salt $N^3$-[2-{2-(4-guanidinophenyl)-1,3,4-thiadiazol-5-yl}-acetyl]-$N^2$-(3-methylphenylsulfonyl)-2,3-(S)-diaminopropionic acid TFA salt Methyl $N^3$-[2-{2-(4-N-hydroxyamidinophenyl)-1,3,4-thiadiazol-5-yl}-acetyl]-$N^2$-(3-methylphenylsulfonyl)-2,3-(S)-diaminopropionate TFA salt Methyl $N^3$-[2-{2-(4-amidophenyl)-1,3,4-thiadiazol-5-yl}-acetyl]-$N^2$-(3-methylphenylsulfonyl)-2,3-(S)-diaminopropionate $N^3$-[2-{2-(4-Amidophenyl)-1,3,4-thiadiazol-5-yl}-acetyl]-$N^2$-(3-methylphenylsulfonyl)-2,3-(S)-diaminopropionic acid Methyl $N^3$-[2-{2-(4-amidinophenyl)-1,3,4-thiadiazol-5-ylthio}acetyl]-$N^2$-(n-butoxycarbonyl)-2,3-(S)-diaminopropionate HCl salt $N^3$-[2-{2-(4-Amidinophenyl)-1,3,4-thiadiazol-5-ylthio}acetyl]-$N^2$-(n-butoxycarbonyl)-2,3-(S)-diaminopropionic acid HCl salt Methyl $N^3$-[2-{2-(4-aminophenyl)-1,3,4-oxadiazol-5-ylthio}acetyl]-$N^2$-(n-butoxycarbonyl)-2,3-(S)-diaminopropionate TFA salt Methyl $N^3$-[2-{2-(4-guanidinophenyl)-1,3,4-oxadiazol-5-ylthio}acetyl]-$N^2$-(n-butoxycarbonyl)-2,3-(S)-diaminopropionate TFA salt Methyl $N^3$-[2-{2-(4-amidinophenyl)-1,3,4-oxadiazol-5-ylthio}-acetyl]-$N^2$-(n-butyloxycarbonyl)-2,3-(S)-diaminopropionate HCl salt Methyl $N^3$-[2-{2-(4-aminophenyl)-1,3,4-oxadiazol-5-yl}-acetyl]-$N^2$-(n-butyloxycarbonyl)-2,3-(S)-diaminopropionate Methyl $N^3$-[2-{2-(4-amidinophenyl)-1,3,4-oxadiazol-5-yl}-acetyl]-$N^2$-(n-butyloxycarbonyl)-2,3-(S)-diaminopropionate TFA salt Methyl N3-[2-{2-(4-guanidinophenyl)-1,3,4-oxadiazol-5-yl}-acetyl]-$N^2$-(n-butyloxycarbonyl)-2,3-(S)-diaminopropionate TFA salt Methyl N-[2-{2-(4-aminophenyl)-1,3,4-oxadiazol-5-ylthio}-acetyl]glycine Methyl N-[2-{2-(4-guanidinophenyl)-1,3,4-oxadiazol-5-ylthio}-acetyl]glycine TFA salt Methyl N-[2-{2-(4-guanidinophenyl)-1,3,4-oxadiazol-5-ylthio}-acetyl]-(S)-phenylalanine TFA salt Ethyl N-[2-{2-(4-amidinophenyl)-1,3,4-oxadiazol-5-ylthio}-acetyl]-(S)-phenylalanine HCl salt Methyl N2-[2-{2-(4-aminophenyl)-1,3,4-oxadiazol-5-ylthio}-acetyl]-N3-(n-butyloxycarbonyl)-2,3-(S)-diaminopropionate TFA salt Methyl $N^2$-[2-{2-(4-N,N'-bis-tert-butoxycarbonylguanidinophenyl)-1,3,4-oxadiazol-5-ylthio}-acetyl]-$N^3$-(n-butyloxycarbonyl)-2,3-(S)-diaminopropionate Methyl $N^2$-[2-{2-(4-amidinophenyl)-1,3,4-thiodiazol-5-ylthio}-acetyl]-$N^3$-(n-butyloxycarbonyl)-2,3-(S)-diaminopropionate HCl salt.

4. A pharmaceutical composition comprising a pharmaceutical carrier and a therapeutically effective amount of a compound of claim 1 or a pharmaceutically acceptable salt from thereof.

5. A pharmaceutical composition comprising a pharmaceutical carrier and a therapeutically effective amount of a compound of claim 2 or a pharmaceutically acceptable salt form thereof.

6. A pharmaceutical composition comprising a pharmaceutical carrier and a therapeutically effective amount of a compound of claim 3 or a pharmaceutically acceptable salt form thereof.

7. A method in inhibiting the aggregation of blood platelets which comprises administering to a host in need of such inhibition a therapeutically effective amount of a compound of claim 1.

8. A method of inhibiting the aggregation of blood platelets which comprises administering to a host in need of such inhibition a therapeutically effective amount of a compound of claim 2.

9. A method of inhibiting the aggregation of blood platelets which comprises administering to a host in need of such inhibition a therapeutically effective amount of a compound of claim 3.

10. A method of treating thromboembolic disorders selected from thrombus or embolus formation, harmful platelet aggregation, reocclusion following thrombolysis, reperfusion injury, restenosis, atherosclerosis, stroke, myocardial infarction, and unstable angina, which comprises administering to a host in need of such treatment a therapeutically effective amount of a compound of claim 1.

11. A method of treating thromboembolic disorders selected from thrombus or embolus formation, harmful platelet aggregation, reocclusion following thrombolysis, reperfusion injury, restenosis, atherosclerosis, stroke, myocardial infarction, and unstable angina, which comprises administering to a host in need of such treatment a therapeutically effective amount of a compound of claim 2.

12. A method of treating thromboembolic disorders selected from thrombus or embolus formation, harmful platelet aggregation, reocclusion following thrombolysis, reperfusion injury, restenosis, atherosclerosis, stroke myocardial infarction, and unstable angina, which comprises administering to a host in need of such treatment a therapeutically effective amount of a compound of claim 3.

* * * * *